United States Patent
Cerione et al.

(10) Patent No.: US 10,526,322 B2
(45) Date of Patent: Jan. 7, 2020

(54) INHIBITORS OF KIDNEY-TYPE GLUTAMINASE, GLS-1

(71) Applicants: CORNELL UNIVERSITY, Ithaca, NY (US); ITHACA COLLEGE, Ithaca, NY (US)

(72) Inventors: Richard Cerione, Ithaca, NY (US); Kristin Cerione, Ithaca, NY (US); Clint Stalnecker, Ithaca, NY (US); Scott Ulrich, Brooktondale, NY (US)

(73) Assignees: Cornell University, Ithaca, NY (US); Ithaca College, Ithaca, NY (US)

( * ) Notice: Subject to any disclaimer, the term of this patent is extended or adjusted under 35 U.S.C. 154(b) by 0 days.

(21) Appl. No.: 15/533,198

(22) PCT Filed: Dec. 5, 2015

(86) PCT No.: PCT/US2015/064152
§ 371 (c)(1),
(2) Date: Jun. 5, 2017

(87) PCT Pub. No.: WO2016/090350
PCT Pub. Date: Jun. 9, 2016

(65) Prior Publication Data
US 2017/0362221 A1   Dec. 21, 2017

Related U.S. Application Data

(60) Provisional application No. 62/102,163, filed on Jan. 12, 2015, provisional application No. 62/088,370, filed on Dec. 5, 2014.

(51) Int. Cl.
| | | |
|---|---|---|
| *C07D 471/04* | (2006.01) |
| *C07D 207/16* | (2006.01) |
| *C07D 221/04* | (2006.01) |
| *C07D 221/06* | (2006.01) |
| *C07D 221/12* | (2006.01) |
| *C07D 221/18* | (2006.01) |
| *C07D 233/61* | (2006.01) |
| *C07D 277/82* | (2006.01) |
| *C07D 295/135* | (2006.01) |
| *C07D 401/10* | (2006.01) |
| *C07C 211/49* | (2006.01) |
| *C07C 211/42* | (2006.01) |
| *C07C 211/58* | (2006.01) |
| *C07C 211/59* | (2006.01) |
| *C07C 237/40* | (2006.01) |
| *C07C 311/21* | (2006.01) |
| *C07C 311/37* | (2006.01) |
| *C12N 9/80* | (2006.01) |
| *C12N 9/96* | (2006.01) |
| *C12Q 1/34* | (2006.01) |
| *C07C 211/52* | (2006.01) |
| *C07C 217/90* | (2006.01) |

(52) U.S. Cl.
CPC .......... *C07D 471/04* (2013.01); *C07C 211/49* (2013.01); *C07C 211/52* (2013.01); *C07C 211/58* (2013.01); *C07C 211/59* (2013.01); *C07C 217/90* (2013.01); *C07C 237/40* (2013.01); *C07C 311/21* (2013.01); *C07C 311/37* (2013.01); *C07D 207/16* (2013.01); *C07D 221/04* (2013.01); *C07D 221/06* (2013.01); *C07D 221/12* (2013.01); *C07D 221/18* (2013.01); *C07D 233/61* (2013.01); *C07D 277/82* (2013.01); *C07D 295/135* (2013.01); *C07D 401/10* (2013.01); *C12N 9/80* (2013.01); *C12N 9/96* (2013.01); *C12Q 1/34* (2013.01); *C12Y 305/01002* (2013.01); *G01N 2333/98* (2013.01)

(58) Field of Classification Search
CPC .. C07D 471/04; C07D 207/16; C07D 221/04; C07D 221/06; C07D 221/12; C07D 221/18; C07D 233/61; C07D 277/82; C07D 295/135; C07D 401/10; C07C 211/49; C07C 211/52; C07C 211/58; C07C 211/59; C07C 237/40; C07C 311/21; C07C 311/37
See application file for complete search history.

(56) References Cited

U.S. PATENT DOCUMENTS

| | | | |
|---|---|---|---|
| 5,552,427 A | 9/1996 | Matsutani et al. |
| 6,451,828 B1 | 9/2002 | Newcomb et al. |
| 6,800,634 B2 | 10/2004 | Sun et al. |
| 2001/0025045 A1 | 9/2001 | Edwards et al. |
| 2012/0220610 A1 | 8/2012 | Cerione et al. |
| 2013/0252983 A1 | 9/2013 | Cerione et al. |

FOREIGN PATENT DOCUMENTS

| | | |
|---|---|---|
| WO | WO 2007/120842 | 10/2007 |
| WO | WO 2010/111504 A2 | 9/2010 |

OTHER PUBLICATIONS

Lielbriedis et al., (1) Latvijas PSR Zinatnu Akademijas Vestis, Kimijas Serija 39-41 (1971) (CAS Abstract) (Year: 1971).*
Lielbriedis et al., 2 Latvijas PSR Zinatnu Akademijas Vestis, Kimijas Serija 251 (1968) (CAS Abstract) (Year: 1968).*

(Continued)

*Primary Examiner* — Timothy R Rozof
(74) *Attorney, Agent, or Firm* — Pepper Hamilton LLP

(57) ABSTRACT

The present invention relates generally to glutaminase inhibitors of Formula I, Formula II, or Formula III, as well as pharmaceutical compounds containing them and methods of their use.

14 Claims, 29 Drawing Sheets

(56) References Cited

OTHER PUBLICATIONS

PCT/US2015/064152, International Search Report and Written Opinion (dated Apr. 8, 2016).
PubChem CID 15174102, "AKOS009869844" (Created Feb. 9, 2007; last accessed Jan. 19, 2016).
Stalnecker et al., "Mechanism by Which a Recently Discovered Allosteric Inhibitor Blocks Glutamine Metabolism in Transformed Cells," Proc. Nat'l Acad. Sci. USA 112(2):394-99 (2015) (E-pub. Dec. 29, 2014).
"The Regulatory Action of Dipeptide "Deglutam" on the Glutamine Metabolized Enzymes in the Carcinosarcoma SM-1 Cells," Biomed. Khim. 51(1):48-52 (2005) (abstract only).
ACS Registry No. 328084-72-6 (2001).
ACS Registry No. 367925-93-7 (2001).
ACS Registry No. 679822-57-2 (2004).
Aghaiypour et al., "Do Bacterial L-Asparaginases Utilize a Catalytic Triad Thr-Tyr-Glu?" Biochim. Biophys. Acta. 1550(2):117-128 (2001).
Aghaiypour et al., "Structural Basis for the Activity and Substrate Specificity of Erwinia chrysanthemi L-Asparaginase," Biochemistry 40(19):5655-5664 (2001).
Alonso et al., "Sensitisation of Ehrlich Ascitic Tumour Cells to Methotrexate by Inhibiting Glutaminase," Anticancer Res. 25(5):3315-3320 (2005).
Benavente & Jacobson, "Niacin Restriction Upregulates NADPH Oxidase and ROS in Human Keratinocytes," Free Radic. Biol. Med. 44(4):527-537 (2008).
Benlloch et al., "Bcl-2 and Mn-SOD Antisense Oligodeoxynucleotides and a Glutamine-Enriched Diet Facilitate Elimination of Highly Resistant B16 Melanoma Cells by Tumor Necrosis Factor-Alpha and Chemotherapy," J. Biol. Chem. 281(1):69-79 (2006).
Bhattacharya & Maity, "Localization of Phosphate Dependent Glutaminase in Ascites Fluid of Ovarian Cancer Patient," Pathol. Oncol. Res. 6(3):217-223 (2000).
Bhattacharya & Maity, "Effect of Purified Glutaminase From Human Ascites Fluid on Experimental Tumor Bearing Mice," J. Exp. Clin Cancer Res. 20(4):599-607 (2001).
Bieganowski et al., "Eukaryotic NAD+ Synthetase Qns1 Contains an Essential, Obligate Intramolecular Thiol Glutamine Amidotransferase Domain Related to Nitrilase," J. Biol. Chem. 278(35):33049-33055 (2003).
Bui et al., "Retinal Function Loss after Monocarboxylate Transport Inhibition," Invest. Ophthalmol. Vis. Sci. 45(2):584-593 (2004).
Burbelo et al., "Altered Rho GTPase Signaling Pathways in Breast Cancer Cells," Breast Cancer Res. Treat. 84:43-48 (2004).
Buschdorf et al., "Brain-Specific BNIP-2-Homology Protein Caytaxin Relocalises Glutaminase to Neurite Terminals and Reduces Glutamate Levels," J.Cell Sci. 119:3337-3350 (2006).
Cammarano & Minden, "Dbl and the Rho GTPases Activate NFκB by IκB kinase (IKK)-Dependent and IKK-Independent Pathways," J. Biol. Chem. 276:25876-25882 (2001).
Campos et al., "Expression of Recombinant Human L-Glutaminase in Escherichia coli: Polyclonal Antibodies Production and Immunological Analysis of Mouse Tissues," Biochim. Biophys. Acta. 1648(1-2):17-23 (2003).
Cappelletti et al., "Helicobacter Pyloril-Asparaginase: A Promising Chemotherapeutic Agent," Biochem. Biophys. Res. Commun. 377(4):1222-1226 (2008).
Carretero et al., "Mitochondrial Glutathione Depletion by Glutamine in Growing Tumor Cells," Free Radic. Biol. Med. 29(9):913-923 (2000).
Carey, FA. Organic Chemistry 6th Ed. McGraw Hill. 2006, chapter 1, p. 9.
CAS Registry No. 296792-93-3 (2000).
CAS Registry No. 309719-68-4 (2000).
CAS Registry No. 312632-81-8 (2001).
CAS Registry No. 385375-94-0 (2002).
CAS Registry No. 406173-09-9 (2002).

Chakrabandhu et al., "Distinctive Molecular Signaling in Triple-Negative Breast Cancer Cell Death Triggered by Flexadecylphosphocholine (Miltefosine)," FEBS Lett. 582:4176-84 (2008).
Chambers et al., "Glutamine Metabolism is Essential for Human Cytomegalovirus Infection," J. Virol. 84(4):1867-1873 (2010).
Chen & Cui, Int. J. Mol. Sci. 16:22830-55 (2015).
Chiarini et al., "Photoexcited Calphostin C Selectively Destroys Nuclear Lamin B1 in Neoplastic Human and Rat Cells—a Novel Mechanism of Action of a Photodynamic Tumor Therapy Agent," Biochim. Biophys. Acta. 1783(9):1642-1653 (2008).
Christofk et al., "Pyruvate Kinase M2 is a Phosphotyrosine-Binding Protein," Nature 452:181-186 (2008).
Clark et al., "Genomic Analysis of Metastasis Reveals an Essential Role for RhoC," Nature 406:532-535 (2000).
Conti et al., Abstract 491.3, "Phosphate-Activated Glutaminase Pag Inhibitors Abolish Glutamate-Immunoreactivity in the Rat Cerebral Cortex," Soc. Neurosci. Abstr. 16(2):1188 (1990).
Curthoys, "Regulation of Glutaminase Activity and Glutamine Metabolism," Annu. Rev. Nutr. 15:133-159 (1995).
Dang et al., "MYC-Induced Cancer Cell Energy Metabolism and Therapeutic Opportunities," Clin. Cancer Res. 15(21)6479-6483 (2009).
Dang, "MYC MicroRNAs and Glutamine Addiction in Cancers," Cell Cycle 8(20):3243-3245 (2009).
Delabarre et al., Biochemistry 50:10764-70 (2011).
De Melo et al., "Indole-3-Acetic Acid Increases Glutamine Utilization by High Peroxidase Activity-Presenting Leukocytes," Life Sci. 75(14):1713-1725 (2004).
Deberardinis et al., "Beyond Aerobic Glycolysis: Transformed Cells Can Engage in Glutamine Metabolism that Exceeds the Requirement for Protein and Nucleotide Synthesis," Proc. Nat'l. Acad. Sci. U.S.A. 104:19345-19350 (2007).
Deberardinis et al., "The Biology of Cancer: Metabolic Reprogramming Fuels Cell Growth and Proliferation," Cell Metab. 7:11-19 (2008).
Dhavala et al., "Expression, Purification and Crystallization of Helicobacter Pylori L-Asparaginase," Acta. Cyrstallogr. Sect. F Struct. Biol. Cryst Commun. 64(Pt 8):740-742 (2008).
Dias & Cerione, "X-Ray Crystal Structures Reveal Two Activated States for RhoC," Biochemistry 46:6547-58 (2007).
Donadio et al., "Antisense Glutaminse Inhibition Modifies the O-GlcNAc Pattern and Flux Through the Hexosamine Pathway in Breast Cancer Cells," J. Cell. Biochem. 103(3):800-811 (2008).
Dos Santos et al., "Metabolism of the Microregions of Human Breast Cancer," Cancer Lett. 216(2):243-248 (2004).
Elgadi et al., "Cloning and Analysis of Unique Human Glutaminase Isoforms Generated by Tissue-Specific Alternative Splicing," Physiol. Genomics 1(2):51-62 (1999).
Erdmannet al. "In Vitro Glutaminase Regulation and Mechanisms of Glutamate Generation in HIV-1-Infected Macrophage," J. Neurochem. 109:551-561 (2009).
Erickson & Cerione, "Structural Elements, Mechanism, and Evolutionary Convergence of Rho Protein-Guanine Nucleotide Exchange Factor Complexes," Biochemistry 43:837-842 (2004).
Estrada et al., "A Novel Approach for the Virtual Screening and Rational Design of Anticancer Compounds," J. Med. Chem. 43:1975-85 (2000).
Etienne-Manneville & Hall, "Rho GTPases in Cell Biology," Nature 420:629-635 (2002).
Ewart & Brosnan, "Rapid Activation of Hepatic Glutaminase in Rats Fed on a Single High-protein Meal," Biochem. J. 293:399-344 (1993).
Fiatte et al., "Expression of PPAR-gamma is Reduced by Medium Supplementation With L-Glutamine in Human Colorectal Caco-2 Cells," Int. J. Mol.Med. 22:825-832 (2008).
Finn et al., "Dasatinib, an Orally Active Small Molecule Inhibitor of Both the src and abl Kinases, Selectively Inhibits Growth of Basal-Type/Triple-Negative Breast Cancer Cell Lines Growing in Vitro," Breast Cancer Res. Treat. 105:319-26 (2007).
Fritz et al., "Rho GTPases are Over-Expressed in Human Tumors," Int. J. Cancer 81:682-687 (1999).

(56) References Cited

OTHER PUBLICATIONS

Fuji, "Biochemical Studies of DBL-Transformation," Dissertation, Cornell University (Aug. 2005).
Gallagher et al., "13C MR Spectroscopy Measurements of Glutaminase Activity in Human Hepatocellular Carcinoma Cells Using Hyperpolarized 13C-Labeled Glutamine," Magn. Reson. Med. 60(2):253-257 (2008).
Gao et al., "C-Myc Suppression of miR-23 Enhances Mitochondrial Glutaminase and Glutamine Metabolism," Nature 458(7239):762-765 (2009).
Georgopoulos et al., "Regulatory Sites and Effects of D-(3H)Aspartate Release From Rat Cerebral Cortex," Neurochem. Res. 20(1):45-49 (1995).
Gharbi et al., "Evaluation of Two-Dimensional Differential Gel Electrophoresis for Proteomic Expression Analysis of a Model Breast Cancer Cell System," Molecular and Cellular Proteomics, 1:91-98 (2002).
Ghosh et al., "Modulation of Tumor Induced Angiogenesis in Ehrlich Ascites Tumor," J. Exp. Clin. Cancer Res. 23(4):681-690 (2004).
Gladilina et al., "Cloning, Expression and Purification of Helicobacter pylori L-Asparaginase," Biomed. Khim. 54(4):482-486 (2008) (abstract only).
Gluck et al., "Implications for Altered Glutamate and GABA Metabolism in the Dorsolateral Prefrontal Cortex of Aged Schizophrenic Patients," Am. J. Psychiatry 159:1165-1173 (2002).
Gusak et al., "Synthesis of Fused Derivatives of 4,7-Phenanthroline by Condensation of 6-Aminoquinoline With Aromatic Aldehydes and Dimedone," Russian J. Org. Chem. 37(10):1495-1502 (2001) (abstract).
Hampson et al., "The PDZ Protein Tip-1 is a Gain of Function Target of the HPV16 E6 Oncoprotein," Int. J. Oncol. 25(5):1249-1256 (2004).
Hartwick & Curthoys, J. Enzyme Inhib. Med. Chem. 27(6):861-67 (2012).
Holten & Gundersen, "Glutamine as a Precursor for Transmitter Glutamate, Aspartate and GABA in the Cerebellum: A Role for Phosphate-Activated Glutaminase," J. Neurochem. 104(4):1032-1042 (2008).
Hunt et al., "Expression and Activity of pH-Regulatory Glutaminase in the Human Airway Epithelium," Am. J. Respir. Crit. Care Med. 165:101-107 (2002).
Joyce et al., "Integration of Rac-Dependent Regulation of cyclin D1 Transcription Through a Nuclear Factor-κb-Dependent Pathway," J. Biol. Chem. 274(36):25245-25249 (1999).
Jung et al., "2,3,7,8-Tetrachlorodibenzo-p-dioxin (TCDD) Inhibits Neurite Outgrowth in Differentiating Human SH-SY5Y Neuroblastoma Cells," Toxicol. Lett. 188(2):153-156 (2009).
Kanamori et al., "The PDZ Protein Tax-Interacting Protein-1 Inhibits Beta-Catenin Transcriptional Activity and Growth of Colorectal Cancer Cells," J. Biol. Chem. 278(40):38758-38764 (2003).
Katt et al., Mol. Cancer Ther. 11(6):1269-78 (2012).
Katt et al., Mol. Cancer Ther. 11(6):1269-78 (2012) (Suppl. Info).
Kaufmann et al., "Glutamine Affects Glutathione Recycling Enzymes in a DMBA-Induced Breast Cancer Model," Nutr. Cancer 60(4):518-525 (2008).
Kenny et al., "Bacterial Expression, Purification and Characterization of Rat Kidney-Type Mitochondrial Glutaminase," Protein Expr. Purif. 31:140-148 (2003).
Kita et al., "Down-Regulation of Glutaminase C in Human Hepatocarcinoma Cell by Diphenylarsinic Acid, a Degradation Product of Chemical Warfare Agents," Toxicol. Appl. Pharmacol. 220(3):262-270 (2007).
Kita et al., "Structure-Effect Relationship in the Down-Regulation of Glutaminase in Cultured Human Cells by Phenylarsenic Compounds," Toxicology 258(2-3):157-163 (2009).
Kobayashi & Millhorn, "Hypoxia Regulates Glutamate Metabolism and Membrane Transport in Rat PC12 Cells," J. Neurochem. 76:1935-1948 (2001).
Kvamme & Lenda, "Evidence for Compartmentalization of Glutamate in Rat Brain Synaptosomes Using the Glutamate Sensitivity of Phosphate-Activated Glutaminase as a Functional Test," Neurosci. Lett. 25(2):193-198 (1981).
Kvamme et al., "Evidence Indicating That Pig Renal Phosphate-Activated Glutaminase Has a Functionally Predominant External Localization in the Inner Mitochondrial Membrane," J. Biol. Chem. 266(20):13185-13192 (1991).
Kvamme et al., Kinetics and Localization of Brain Phosphate Activated Glutaminase, J. Neurosci. Res. 66(5):951-958 (2001).
Kvamme et al., "Novel Form of Phosphate Activated Glutaminase in Cultured Astrocytes and Human Neuroblastoma Cells, PAG in Brain Pathology and Localization in the Mitochondria," Neurochem. Res. 33(7):1341-1345 (2008).
Kvamme et al., "Properties of Phosphate Activated Glutaminase in Astrocytes Cultured From Mouse Brain," Neurochem. Res. 7(6):761-770 (1982).
Lima et al., "Walker 256 Tumour Growth Causes Marked Changes of Glutamine Metabolism in Rat Small Intestine," Cell Biochem. Funct. 20:107-113 (2002).
Lin et al., "Specific Contributions of the Small GTPases Rho, Rac and Cdc42 to Dbl Transformation," J. Biol. Chem. 274(33):23633-23641 (1999).
Lora et al., "Antisense Glutaminase Inhibition Decreases Glutathione Antioxidant Capacity and Increases Apoptosis in Ehrlich Ascitic Tumour Cells," Eur. J. Biochem. 271:4298-4306 (2004).
Magedov IV. et al., "Discovery and Investigation of Antiproliferative and Apoptosis-Inducing Properties of New Heterocyclic Podophyllotoxin Analogues Accessible by a One-Step Multicomponent Synthesis," J. Med. Chem. 50:5186_92 (2007).
Maity et al., "Neovascularisation Offers a New Perspective to Glutamine Related Therapy," Indian J. Exp. Biol. 38(1):88-90 (2000).
Martin-Rufian et al., "Identification of Genes Downregulated in Tumor Cells Expressing Antisense Glutaminase mRNA by Differential Display," Cancer Biol. Therapy 5(1):54-58 (2006).
Matés et al., "Glutamine Homeostasis and Mitochondrial Dynamics," Int. J. Biochem. Cell Biol. 41(10):2051-2061 (2009).
Medina et al., "Relevance of Glutamine Metabolism to Tumor Cell Growth," Mol. Cell. Biochem. 113:1-15 (1992).
Medina, "Glutamine Metabolism: Nutritional and Clinical Significance," J. Nutr. 131:2539S-2542S (2001).
Nag, "Effect of Organophosphate Pesticides on Glutaminase and Glutamine Synthetase Activity in Rat Brain," Indian J. Exp. Biol. 30(6):543-545 (1992).
Novak et al., "Androgen Secretion by Rcho-1 Cells is Independent of Extracellular Glutamate Concentration," Placenta 25(6):548-552 (2004).
Ochiai et al., "Characterization of Several Amino Acid Transports and Glutamine Metabolish in MOLT4 Human T4 Leukemia Cells," Clin. Lab Haematol. 28(6):399-404 (2006).
Osbakken et al., "Effect of Cyclocreatine Feeding on Levels of Amino Acids in Rat Hearts Before and After an Ischemic Episode," Am. J. Physiol. Heart Circ. Physiol. 261(6):H1919-26 (1991).
PCT/US10/28688, International Search Report and Written Opinion (dated Sep. 23, 2010).
Pérez-Gómez et al., "Co-Expression of Glutaminase K and L Isoenzymes in Human Tumour Cells," Biochem. J. 386(Pt. 3):535-542 (2005).
Perona et al., "Activation of the Nuclear Factor-κB by Rho, CDC42, and Rac-1 Proteins," Genes Dev. 11:463-475 (1997).
Pickering et al., "Pharmacological Inhibitors of NF-κB Accelerate Apoptosis in Chronic Lymphocytic Leukemia Cells," Oncogene 26:1166-1177 (2007).
Porter et al., "Complexity and Species Variation of the Kidney-type Glutaminase Gene," Physiol. Genomics 9:157-166 (2002).
Prakasham et al., "Evaluation of Antineoplastic Activity of Extracellular Asparaginase Produced by Isolated Bacillus Circulans," Appl. Biochem. Biotechnol. 160(1):72-80 (2010).
Preuss et al., "Effects of Glutamine Deamination on Glutamine Deamidation in Rat Kidney Slices," J. Clin. Invest. 52(4):755-764 (1973).

(56) References Cited

OTHER PUBLICATIONS

Reinert et al., "Role of Glutamine Depletion in Directing Tissue-Specific Nutrient Stress Responses to L-Asparaginase," *J. Biol. Chem.* 281(42):31222-31233 (2006).
Roberg et al., "Kinetics of a Novel Isoform of Phosphate Activated Glutaminase (PAG) in SH-SY5Y Neuroblastoma Cells," *Neurochem. Res.* 35(6):875-880 (2009).
Robinson et al., "Novel Mechanism of Inhibition of Rat Kidney-Type Glutaminase by Bis-2-(5-Phenylacetamido-1,2,4-Thiadiazol-2-yl)Ethly Sulfide (BPTES)," Biochem. J. 406:407-14 (2007).
Roy et al., "Acivicin With Glutaminase Regulates Proliferation and Invasion of Human MCF-7 and OAW-42 Cells—An in vitro Study," *Indian J. Exp. Biol.* 46(1):22-26 (2008).
Roy & Maity, "Modulation of Metastatic Potential of B16F10 Melanoma Cells by Acivicin: Synergistic Action of Glutaminase and Potentiation of Cisplatin Cytotoxicity," *Asian Pac. J. Cancer Prev.* 8(2):301-06 (2007).
Segura et al., "Ehrlich Ascites Tumor Cells Expressing Anit-Sense Glutaminase mRNA Lose Their Capacity to Evade the Mouse Immune System," *Int. J. Cancer* 91:379-384 (2001).
Segura et al., "Inhibition of Glutaminase Expression Increases Sp1 Phosphorylation and Sp1/Sp3 Transcriptional Activity in Ehrlich Tumor Cells," *Cancer Lett.* 218(1):91-98 (2005).
Shimizu et al., "Bcl-2 Family Proteins Regulate the Release of Apoptogenic Cytochrome c by the Mitochondrial Channel VDAC," *Nature* 399:483-487 (1999).
Snodgrass & Lund, "Allosteric Properties of Phosphate-Activated Glutaminase of Human Liver Mitochondria," *Biochim. Biophys. Acta* 798(1):21-27 (1984).
Sovak et al., "Aberrant Nuclear Factor-kB/Rel Expression and the Pathogenesis of Breast Cancer," *J. Clin. Invest.* 100(12):2952-2960 (1997).
Svoboda & Kerschbaum, "Glutamine-Induced Apoptosis in Microglia is Mediated by Mitochondrial Dysfunction," *Eur. J. Neurosci.* 30(2):196-206 (2009).
Szeliga & Obara-Michlewska, "Glutamine in Neoplastic Cells: Focus on the Expression and Roles of Glutaminases," *Neurochem. Int.* 55(1-3):71-75 (2009).
Szeliga et al., "Lack of Expression of the Liver-Type Glutaminase (LGA) mRNA in Human Malignant Gliomas," *Neurosci. Lett.* 374(3):171-173 (2005).
Szeliga et al., "Relative Expression of mRNAS Coding for Glutaminase Isoforms in CNS Tissues and CNS Tumors," *Neurochem. Res.* 33(5):808-813 (2008).
Szeliga et al., "Transfection With Liver-Type Glutaminase cDNA Alters Gene Expression and Reduces Survival, Migration and Proliferation of T98G Glioma Cells," *Glia* 57(9):1014-1023 (2009).
Thangavelu et al., *PNAS* 109(20):7705-10 (2012).
Taylor et al., "A Phase I and Pharmacodynamic Evaluation of Polyethylene Glycol-Conjugated L-Asparaginase in Patients with Advanced Solid Tumors," *Cancer Chemother. Pharmacol.* 47:83-88 (2001).
Turner & McGivan, "Glutaminase Isoform Expression in Cell Lines Derived from Human Colorectal Adenomas and Carcinomas," *Biochem. J.* 370:403-408 (2003).
Valastyan et al., "A Pleiotropically Acting microRNA, miR-31, Inhibits Breast Cancer Metastasis," *Cell* 137:1032-1046 (2009).
Wang et al., *Cancer Cell* 18:207-19 (2010).
Wheeler & Ridley, Review, "Why Three Rho Proteins? RhoA, RhoB, RhoC, and Cell Motility," Experimental Cell Res. 301:43-49 (2004).
Whitehead et al., "Dependence of Dbl and Dbs Transformation on MEK and NF-kappaB Activation," *Mol. Cell Biol.* 19:7759-7770 (1999).
Wiessner et al., "Localization and Possible Function of the Glutamate Transporter, EAAC1, in the Rat Retina," *Cell Tissue Res.* 310(1):31-40 (2002).
Wilson et al., *Trends Mol. Med.* 19(2):74-82 (2013).
Wojcik et al., "Glutamine-Dependent NAD+ Synthetase. How a Two-Domain, Three-Substrate Enzyme Avoids Waste," *J. Biol. Chem.* 281(44):33395-33402 (2006).
Yamaoka, "[GMP Synthetase]," *Nihon Rinsho* 61(Suppl 1):66-70 (2003).
Ye et al., "(1R,3S)-1-Aminocyclopentane-1,3-Dicarboxylic Acid (RS-ACPD) Reduces Intracellular Glutamate Levels in Astrocytes," *J. Neurochemistry* 79(4):756-766 (2001).
Zacharias et al., "Human Cutaneous Melanoma Expresses a Significant Phosphate-Dependent Glutaminase Activity: A Comparison With the Surrounding Skin of the Same Patient," *Cell Biochem. Funct.* 21(1):81-84 (2003).
Zielke et al., "Functional Intracellular Glutaminase Activity in Intact Astrocytes," *Neurochem. Res.* 14(4):327-332 (1989).
PCT/US2015/064152, International Preliminary Report on Patentability (dated Jun. 15, 2017).
Gross et al., "Antitumor Activity of the Glutaminase Inhibitor CB-839 in Triple-Neagtive Breast Cancer," Mol. Cancer Ther. 13(4):890-901 (2014).
PCT/US2010/028688, International Search Report and Written Opinion (dated Sep. 23, 2010).

\* cited by examiner

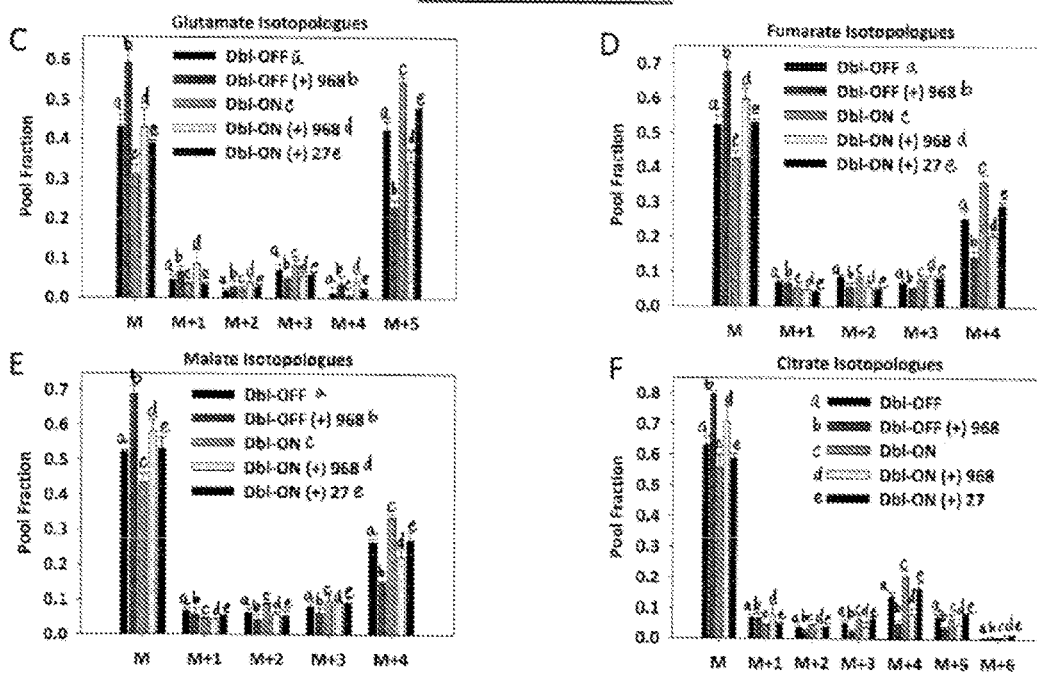
Figures 2C–F
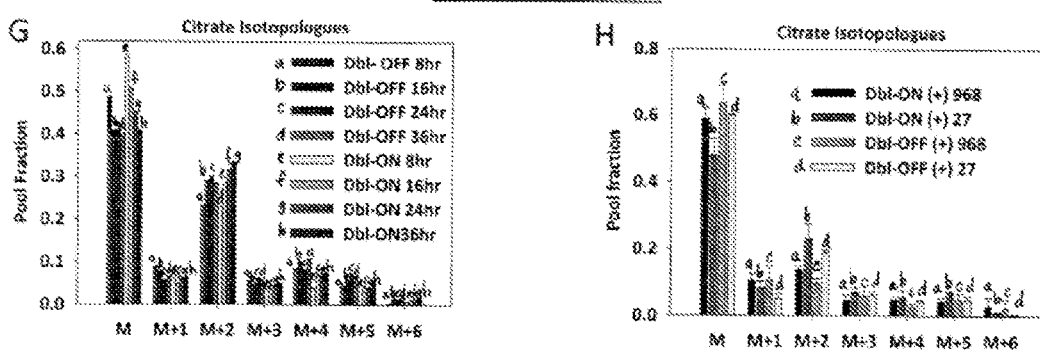
Figures 2G–H

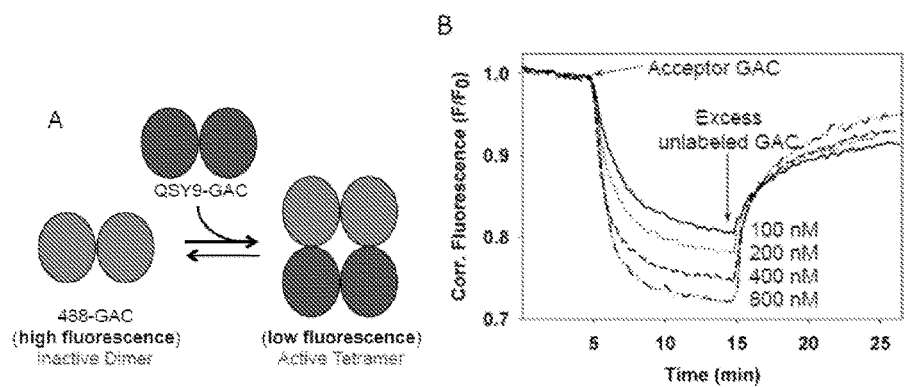
Figures 3A–B
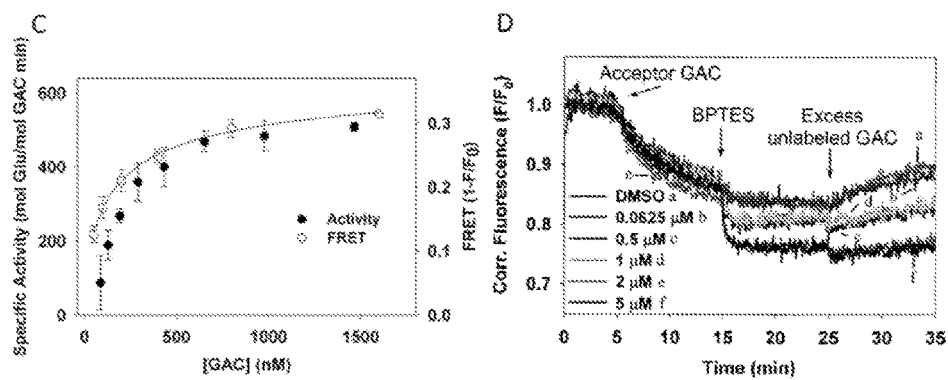
Figures 3C–D
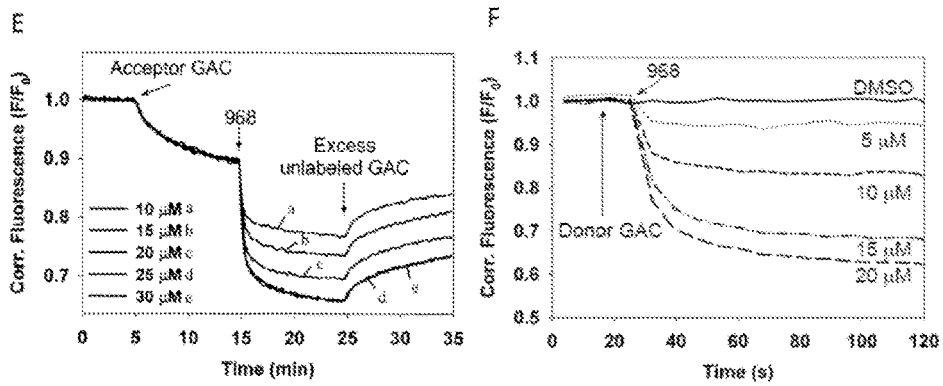
Figures 3E–F

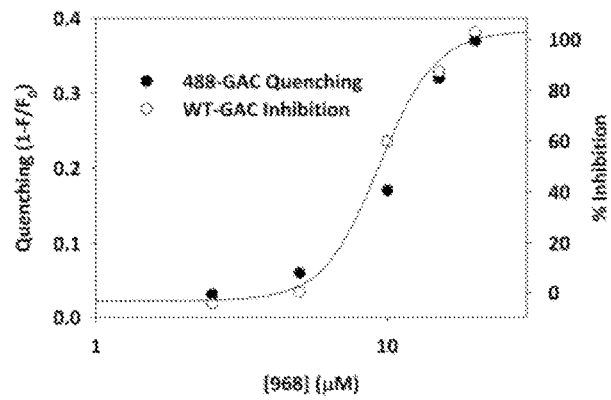
Figure 4
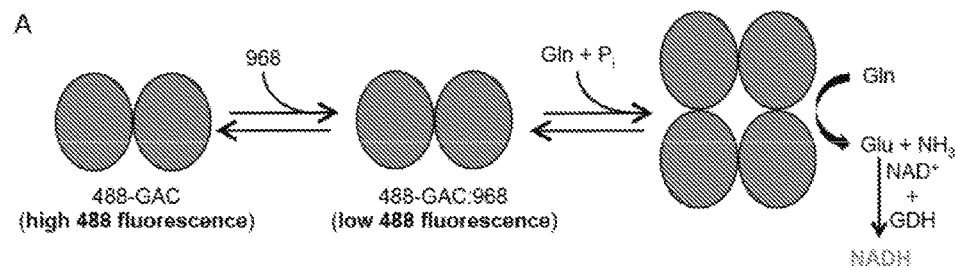
Figure 5A
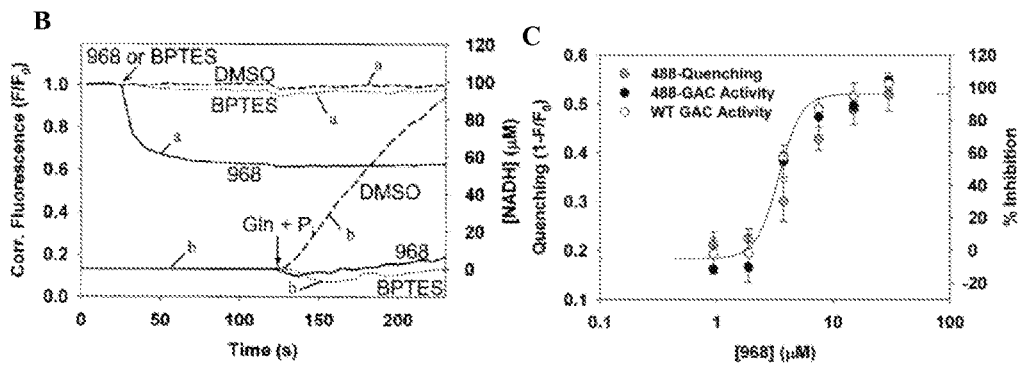
Figures 5B–C

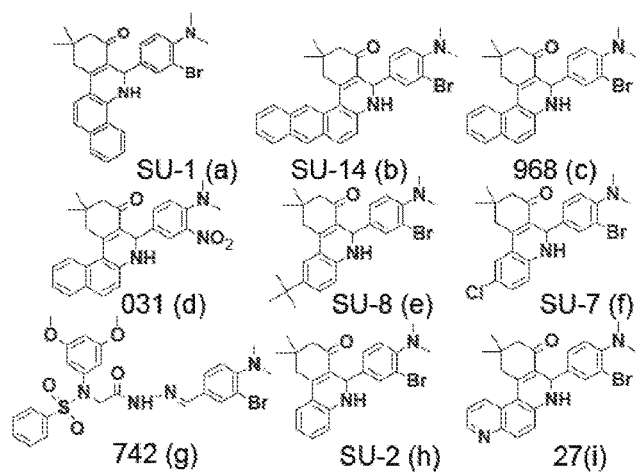
Figure 5D
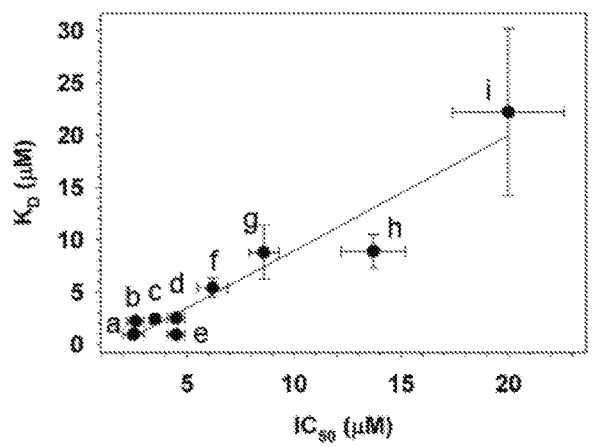
Figure 5E
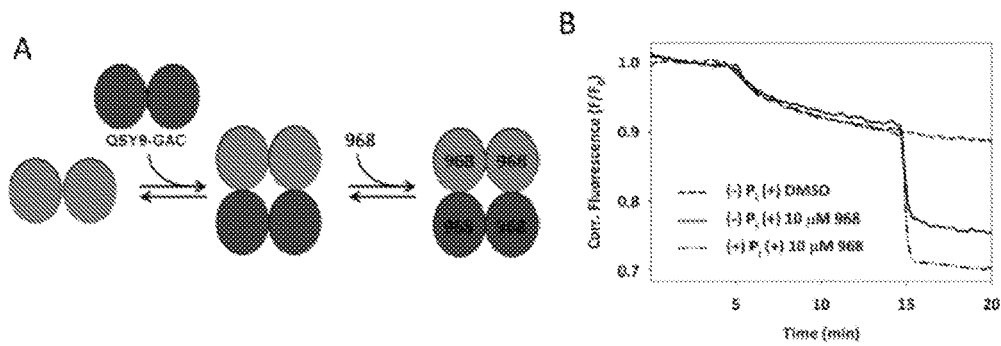
Figures 6A–B

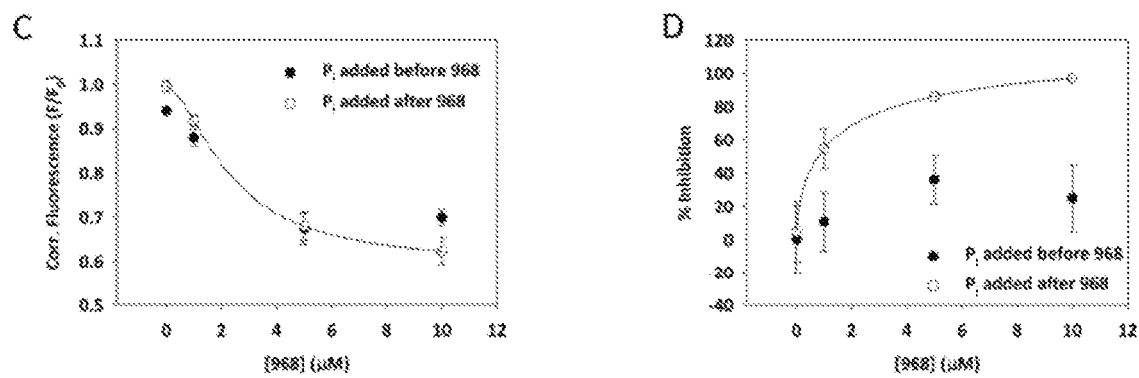
Figures 6C–D
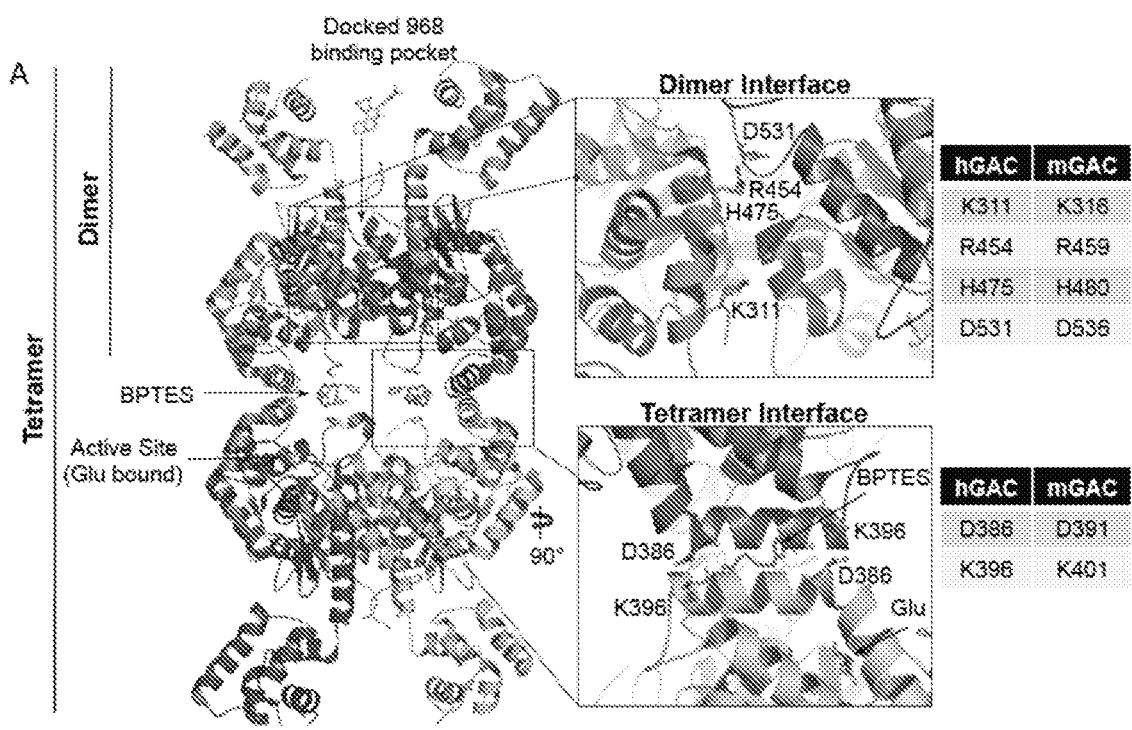
Figure 7A
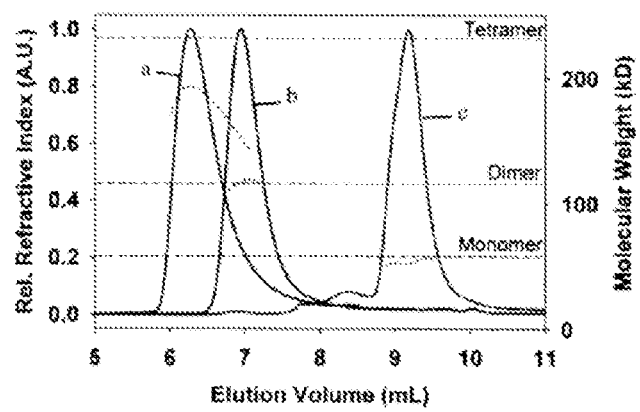
Figure 7B

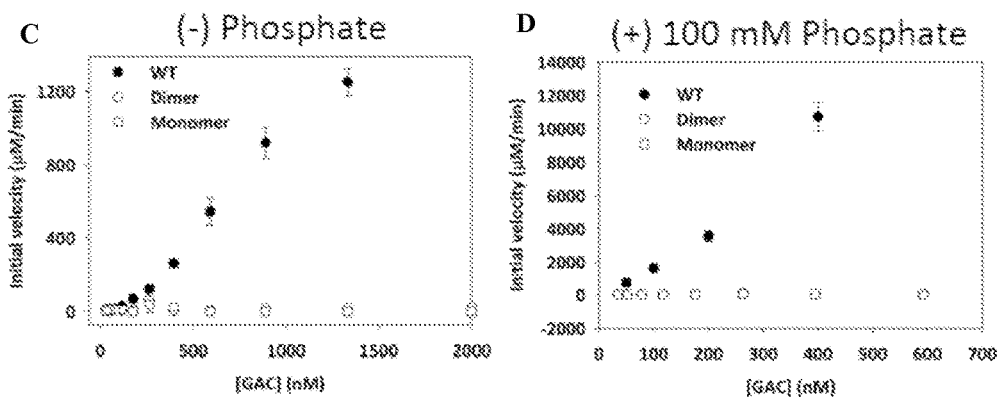
Figures 7C–D
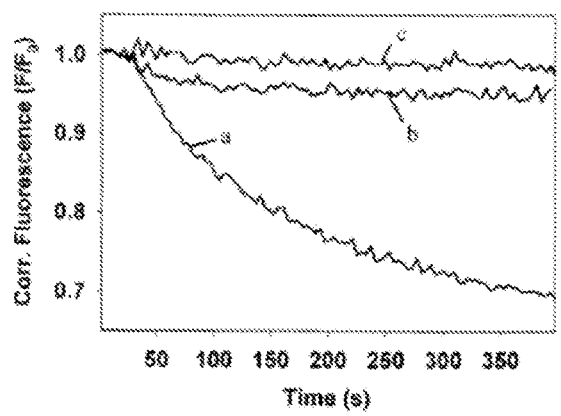
Figure 7E
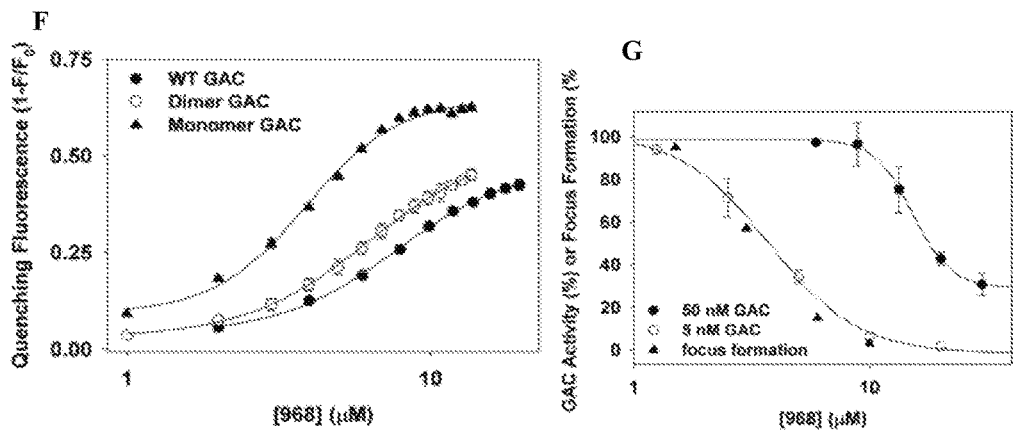
Figures 7F–G

SU-23 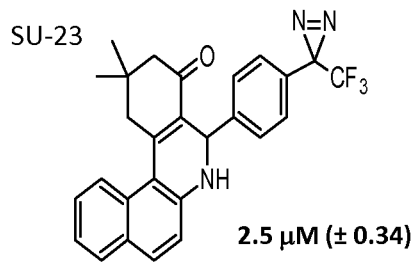
2.5 µM (± 0.34)
SU-24 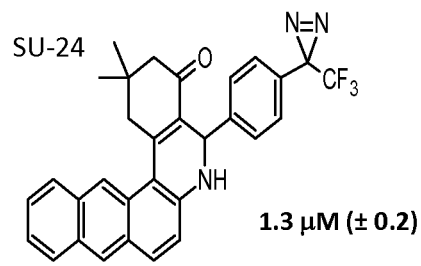
1.3 µM (± 0.2)
SU-25 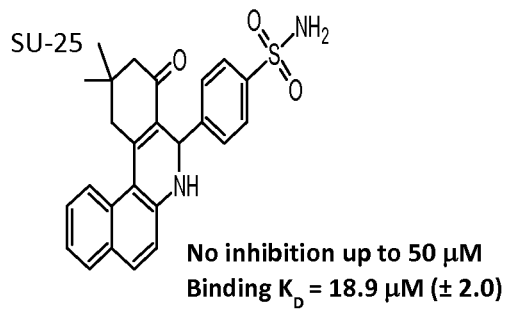
No inhibition up to 50 µM
Binding K$_D$ = 18.9 µM (± 2.0)
SU-26 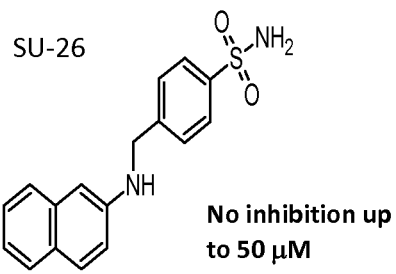
No inhibition up to 50 µM
SU-27 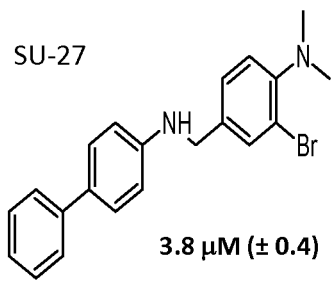
3.8 µM (± 0.4)
SU-28 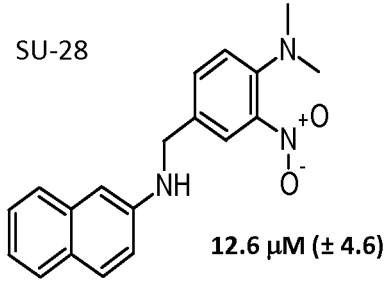
12.6 µM (± 4.6)
SU-29 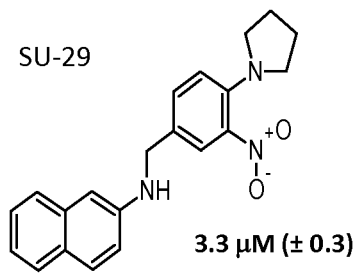
3.3 µM (± 0.3)
SU-30 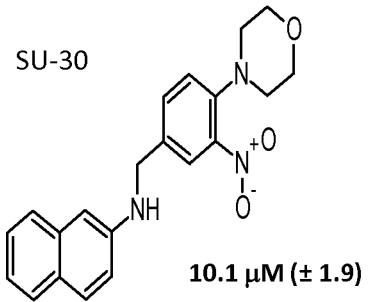
10.1 µM (± 1.9)
SU-31 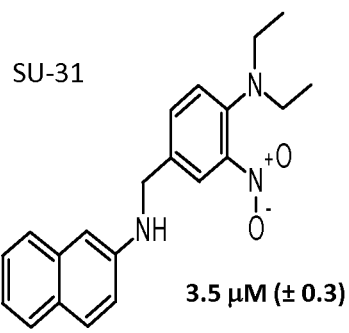
3.5 µM (± 0.3)
SU-32 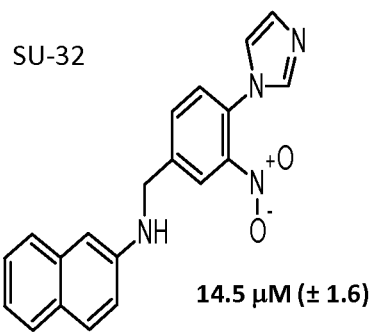
14.5 µM (± 1.6)
Figure 9 (cont.)

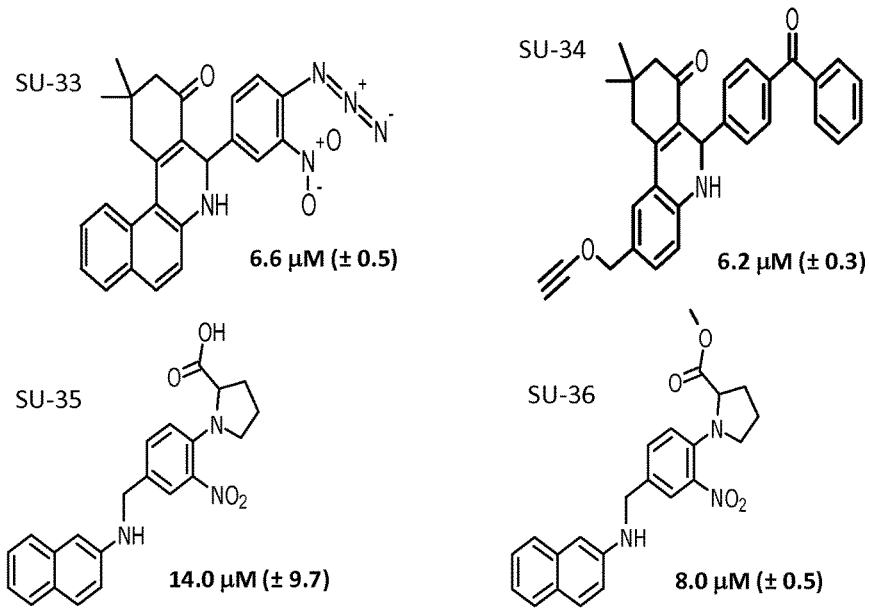
Figure 9 (cont.)
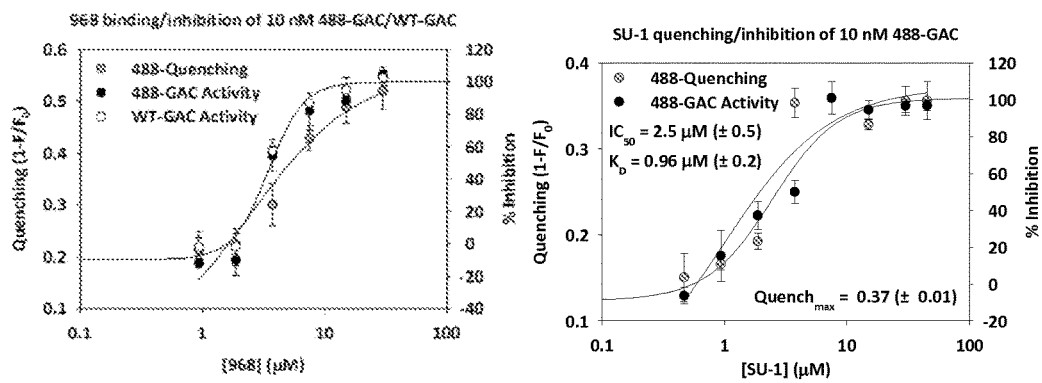
Figures 10A (left) and 10B (right)
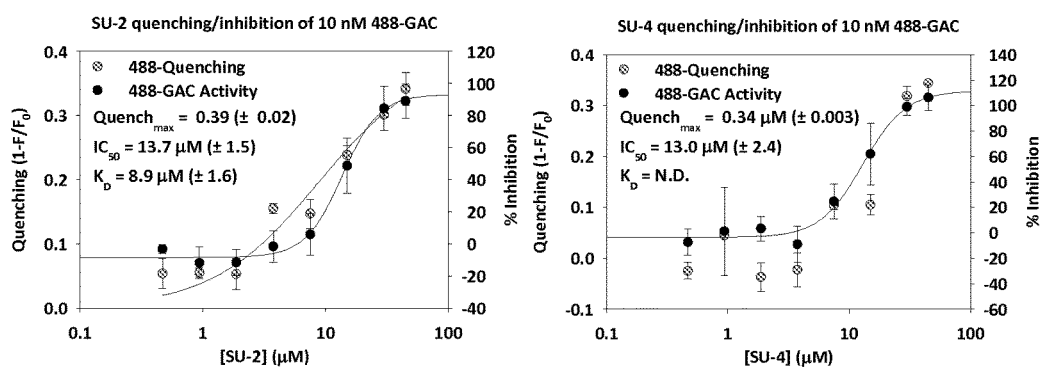
Figures 10C (left) and 10D (right)

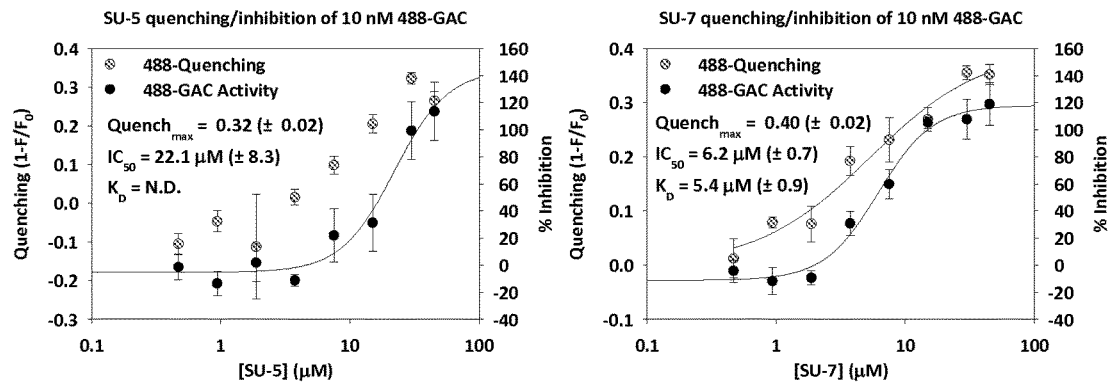
Figures 10E (left) and 10F (right)
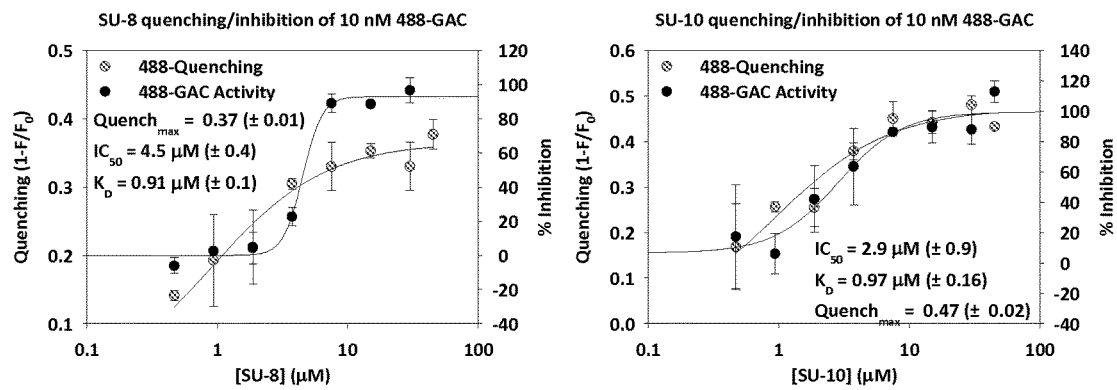
Figures 10G (left) and 10H (right)
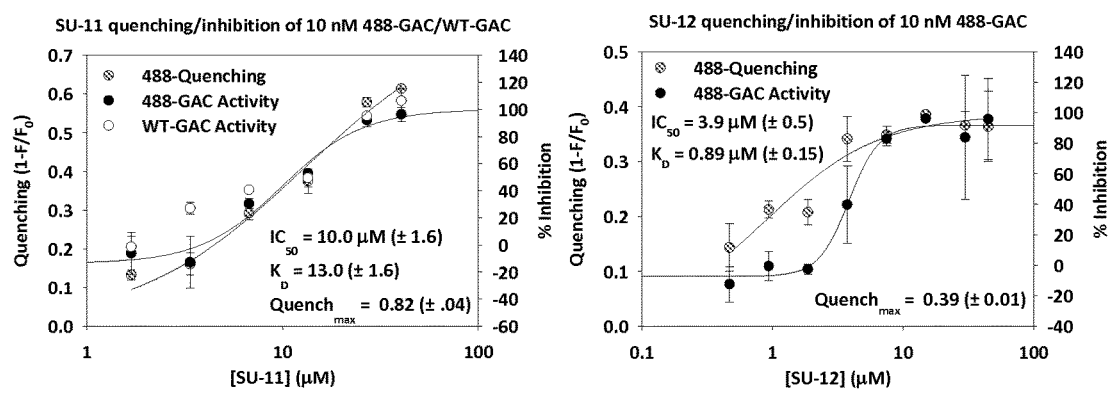
Figures 10I (left) and 10J (right)

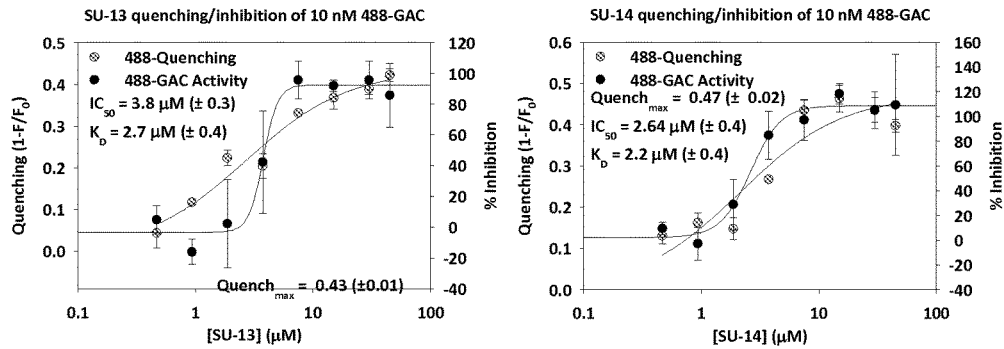
Figures 10K (left) and 10L (right)
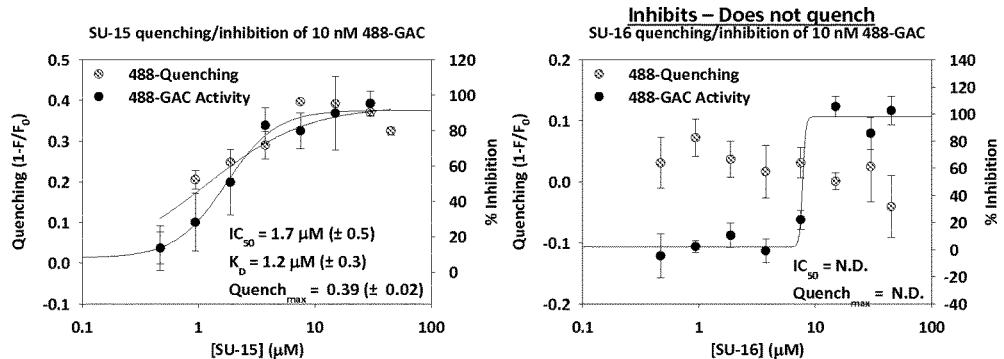
Figures 10M (left) and 10N (right)
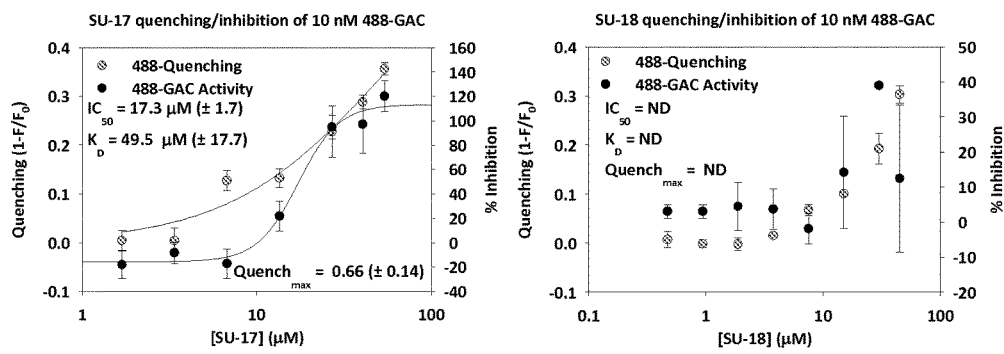
Figures 10O (left) and 10P (right)

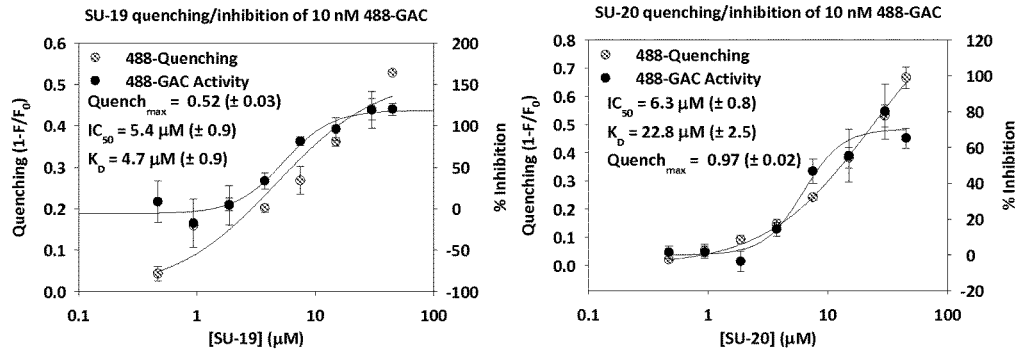
Figures 10Q (left) and 10R (right)
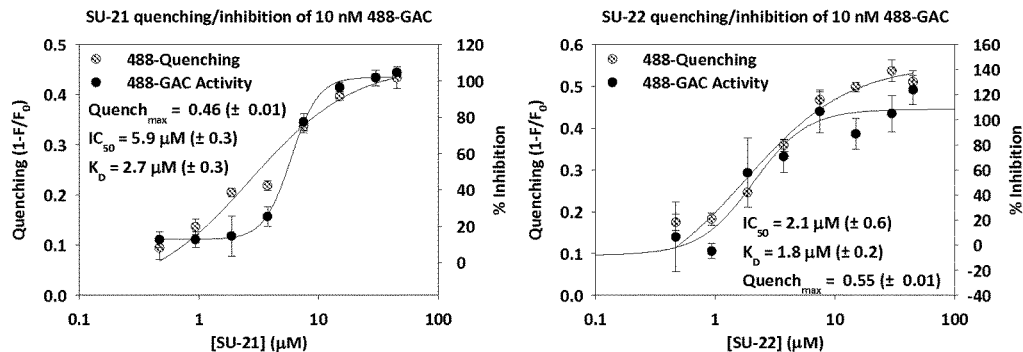
Figures 10S (left) and 10T (right)
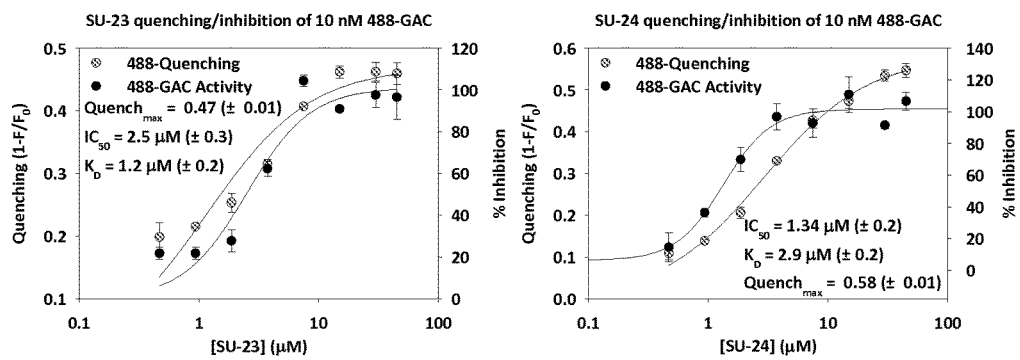
Figures 10U (left) and 10V (right)

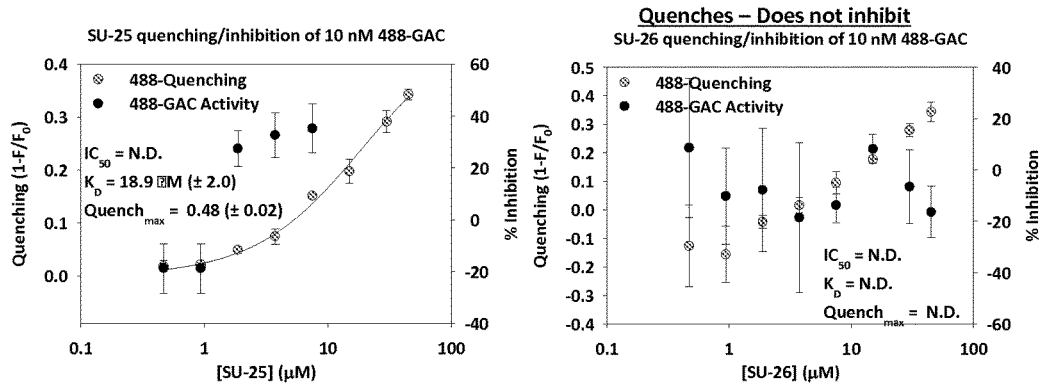
Figures 10W (left) and 10X (right)
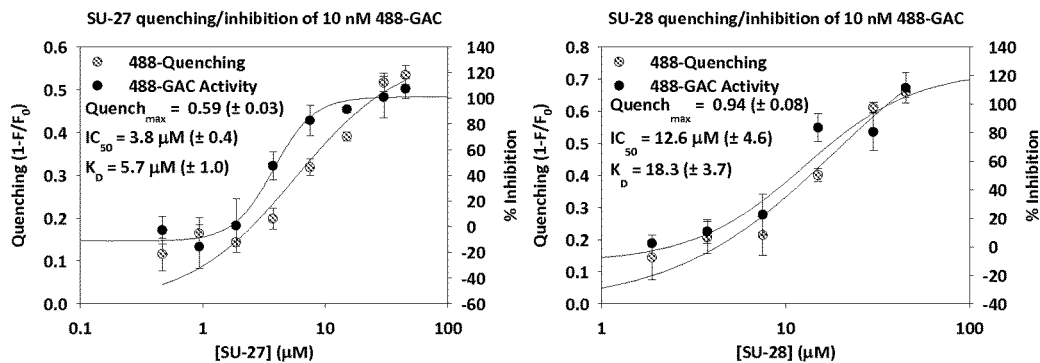
Figures 10Y (left) and 10Z (right)
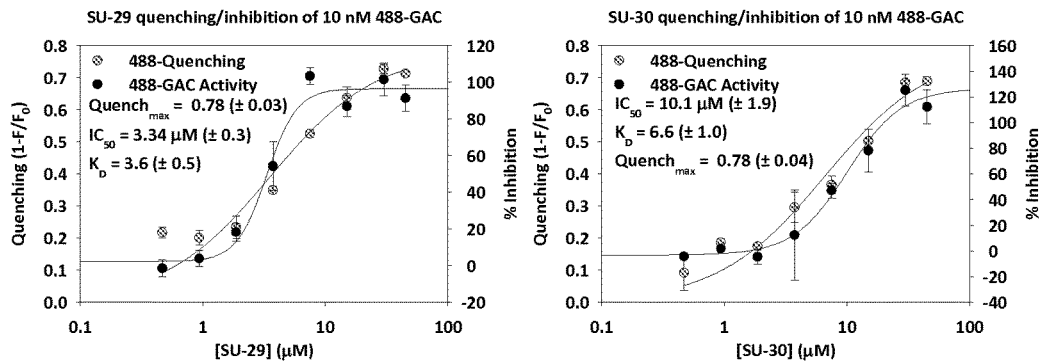
Figures 10AA (left) and 10AB (right)

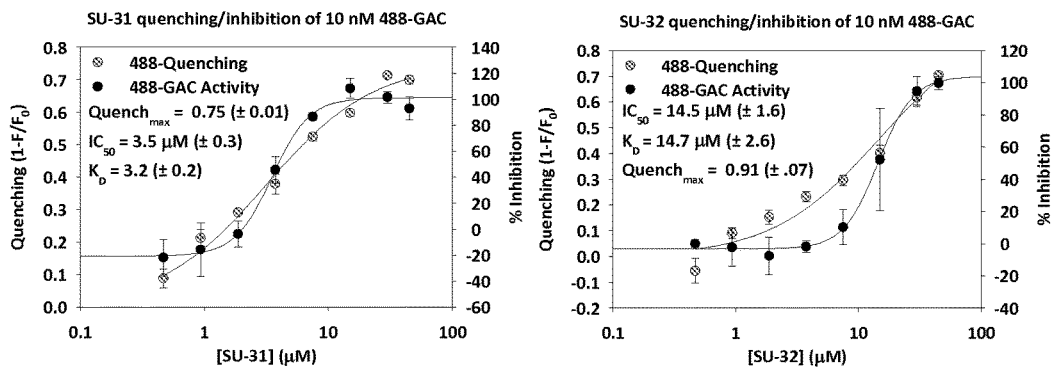
Figures 10AC (left) and 10AD (right)
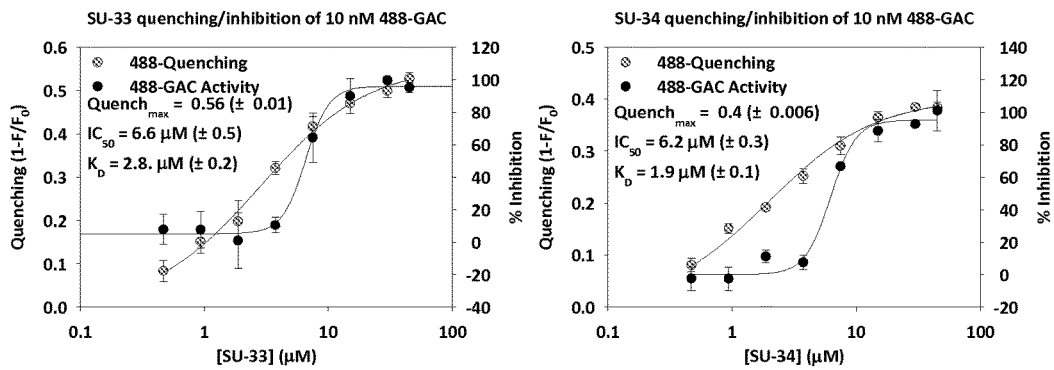
Figures 10AE (left) and 10AF (right)
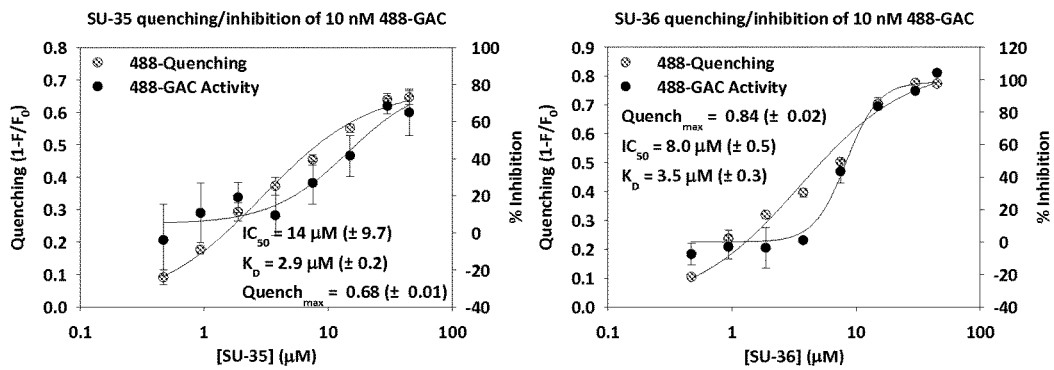
Figures 10AG (left) and 10AH (right)

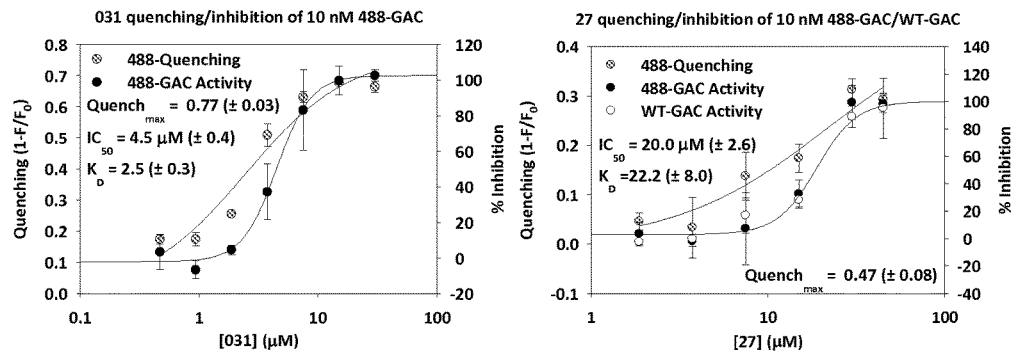
Figures 10AI (left) and 10AJ (right)
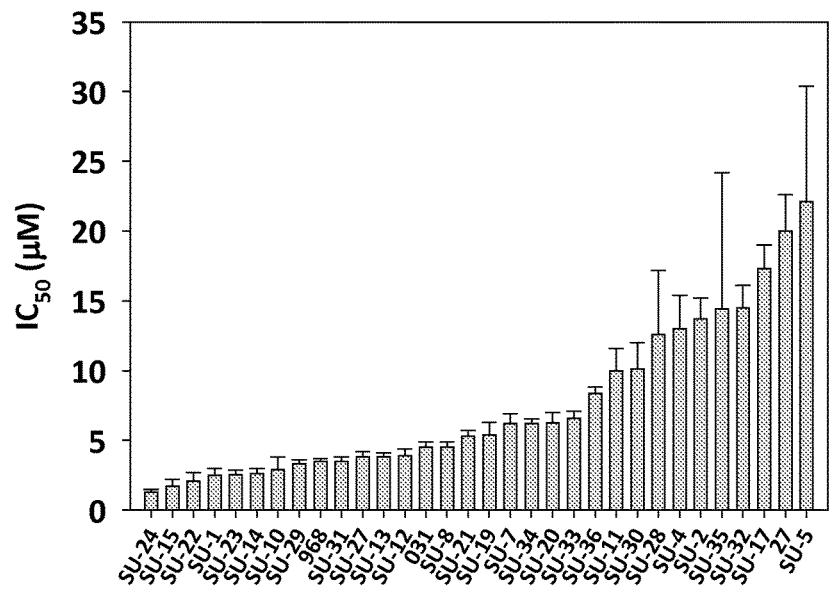
Figure 11

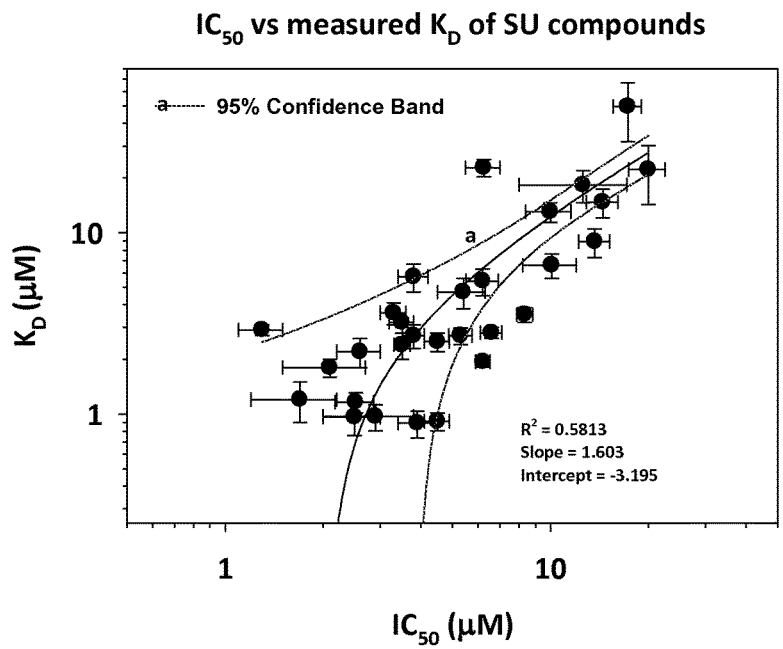
Figure 12
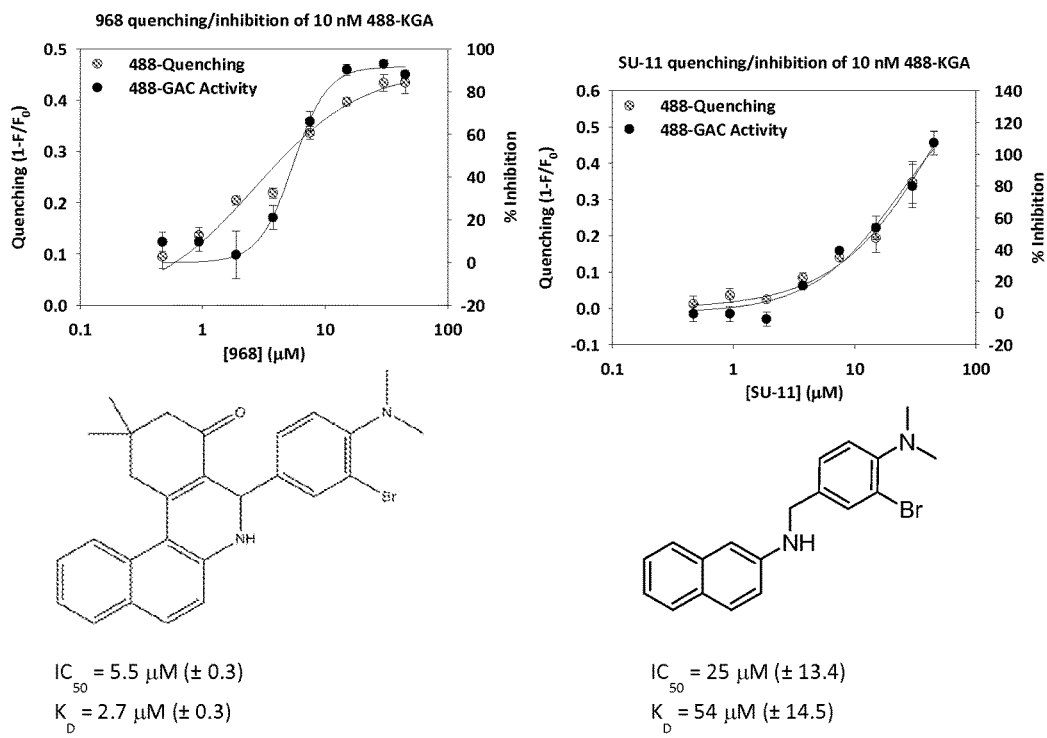
Figure 13A (left) and 13B (right)

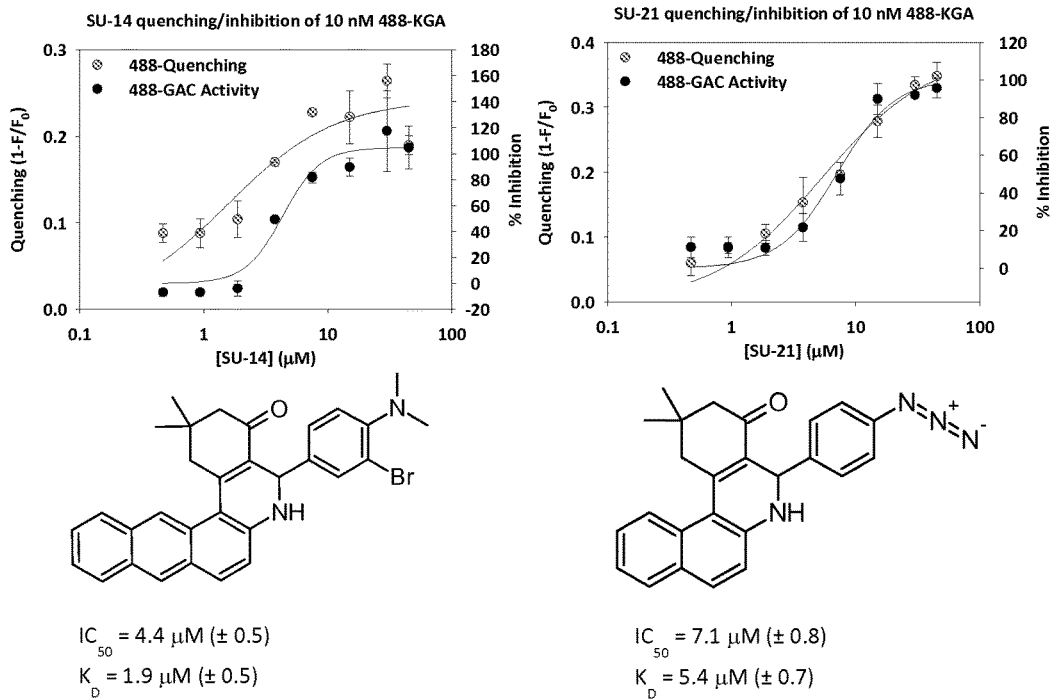
Figure 13C (left) and 13D (right)
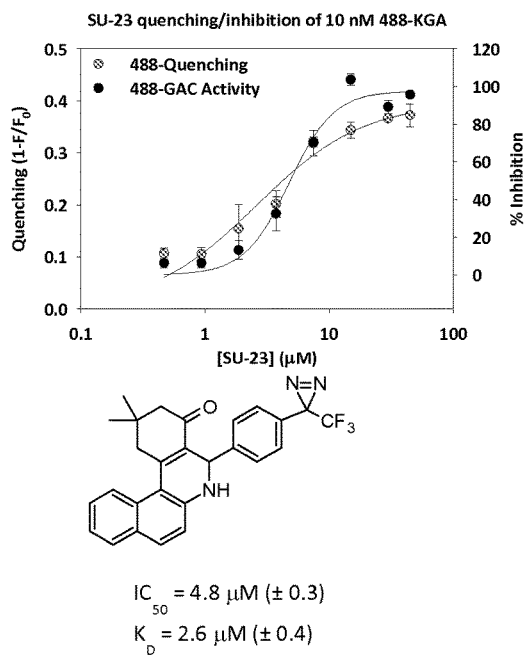
Figure 13E

Evaluation of inhibitory properties of SU-16–SU-20 on the proliferation of MDA-MB-231 breast cancer cells
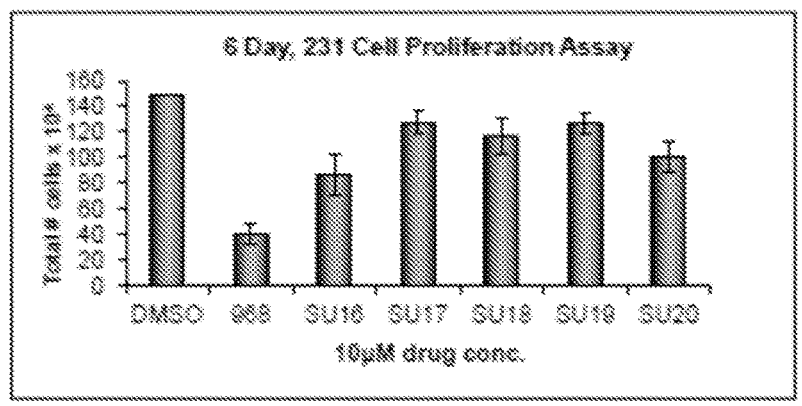
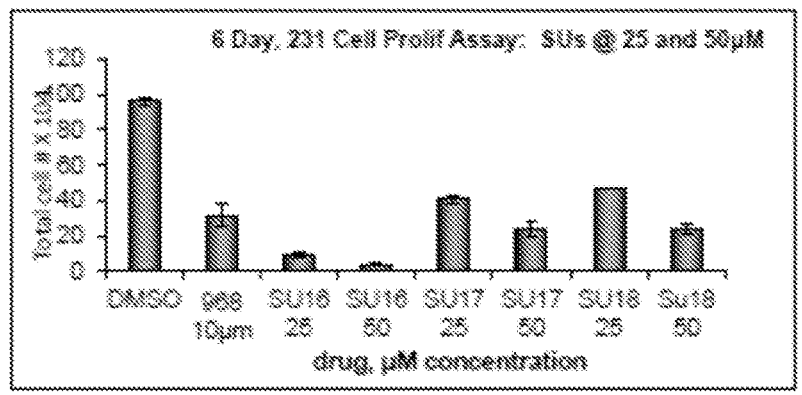
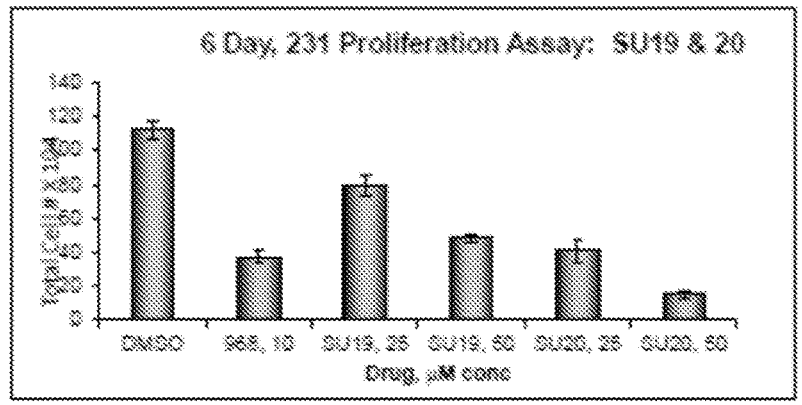
Figure 15

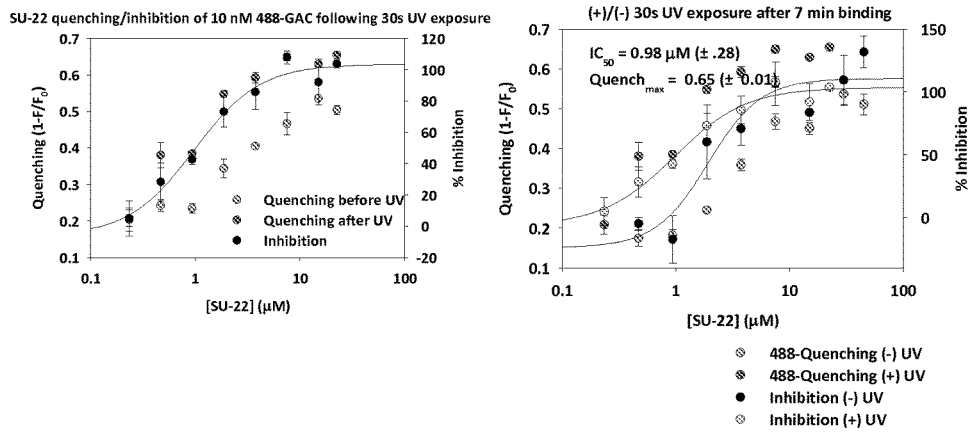
Figure 16A (left) and 16B (right)
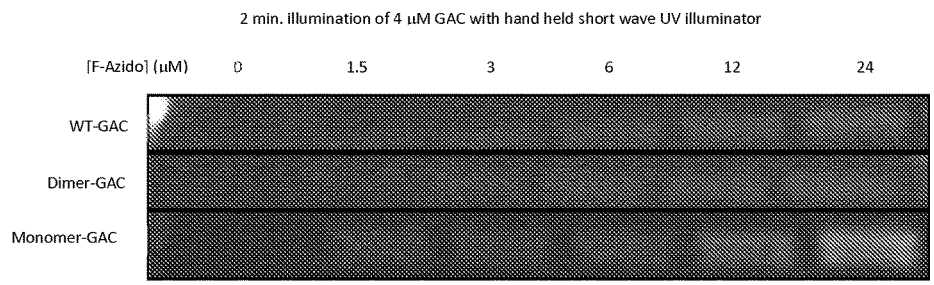
Figure 17
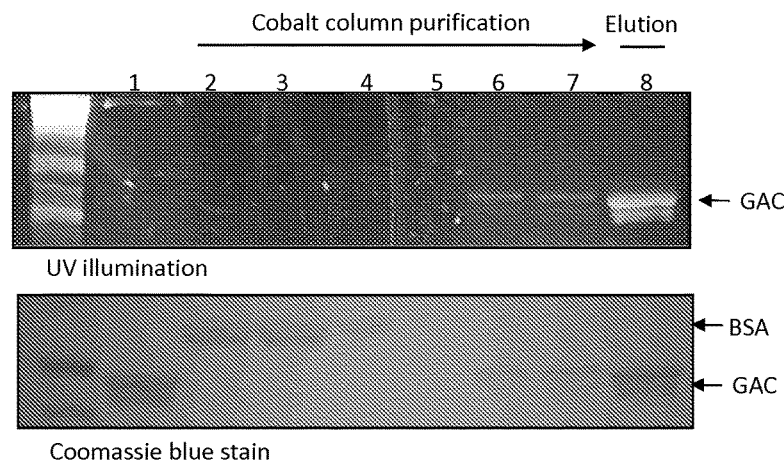
Figure 18A

[GAC] = 9.7 μM
[F-azido] = 5.3 μM
Ratio F-azido/GAC = 0.54

INHIBITORS OF KIDNEY-TYPE GLUTAMINASE, GLS-1

This application is a national stage application under 35 U.S.C. § 371 of PCT Application No. PCT/US2015/064152, filed Dec. 5, 2015, which claims the benefit of U.S. Provisional Patent Application Ser. No. 62/088,370, filed Dec. 5, 2014, and U.S. Provisional Patent Application Ser. No. 62/102,163, filed Jan. 12, 2015, each of which are hereby incorporated by reference in their entirety.

This invention was made with government support under grant number 2R01GM40654 awarded by National Institutes of Health. The government has certain rights in this invention.

FIELD OF THE INVENTION

The present invention relates to inhibitors of glutaminase.

BACKGROUND OF THE INVENTION

Tumor cells have an absolute requirement for glutamine as a growth substrate. Glutamine is required as a precursor for both DNA synthesis and protein synthesis, and may also be used as a respiratory substrate. In experiments where glutamine metabolism in tumor cells has been specifically compared with that in non-transformed cells of the same origin, glutamine metabolism in the tumor cells has been found to be considerably faster. This is true for human hepatocytes and hepatoma cells (Souba, W., "Glutamine and Cancer," *Ann. Surg.* 218:715-28 (1993)) and also for glutamine oxidation in rat kidney fibroblasts and rat fibrosarcoma cells (Fischer et al., "Adaptive Alterations in Cellular Metabolism and Malignant Transformation," *Ann. Surg.* 227:627-34 (1998)).

The first reaction in glutamine metabolism is hydrolysis of glutamine to glutamate via the mitochondrial enzyme phosphate-dependent glutaminase. Two major isoforms of this enzyme have been characterized. These are known as the kidney form (K-type) which was first cloned from rat kidney (Shapiro et al., "Isolation, Characterisation, and In vitro Expression of a cDNA That Encodes the Kidney Isoenzyme of the Mitochondrial Glutaminase," *J. Biol. Chem.* 266:18792-96 (1991)) and is expressed in many mammalian tissues, and the liver form (L-type) (Chung-Bok et al., "Rat Hepatic Glutaminase, Identification of the Full Coding Sequence and Characterisation of a Functional Promoter," *Biochem. J.* 324:193-200 (1997)) which was originally identified in post-natal liver. These two enzymes have different kinetic properties. A splice variant of the K-type, Glutaminase C (GAC), has also been identified and both are commonly referred to as GLS1.

Although the cDNAs encoding the two isoforms have regions of high sequence similarity, they also differ significantly elsewhere and the enzyme isoforms are the products of different genes (for a review see (Curthoys et al., "Regulation of Glutaminase Activity and Glutamine Metabolism," *Annu. Rev. Nutr.* 16:133-59 (1995)). Glutamine metabolism is essential for tumor cell growth but there are few studies at present on glutaminase expression in tumor cells. In mouse Ehrlich ascites cells (Quesada et al., "Purification of Phosphate-Dependent Glutaminase from Isolated Mitochondria of Ehrlich Ascites-Tumor Cells," *Biochem. J.* 255:1031-35 (1988)) and rat fibrosarcoma cells (Fischer et al., "Adaptive Alterations in Cellular Metabolism and Malignant Transformation," *Ann. Surg.* 227:627-34 (1998)), an enzyme with the kinetic properties of the K-type glutaminase is expressed. Rat and human hepatocytes express the L-type glutaminase, but this is not expressed in hepatoma cell lines, which express the K-type instead (Souba, W. W., "Glutamine and Cancer," *Ann. Surg.* 218:715-28 (1993)). Inhibition of K-type glutaminase expression by anti-sense mRNA in Ehrlich ascites cells has been shown to decrease the growth and tumorigenicity of these cells (Lobo et al., "Inhibition of Glutaminase Expression by Antisense mRNA Decreases Growth and Tumorigenicity of Tumor Cells," *Biochem. J.* 348:257-61 (2000)).

Since it is well-known that tumorigenesis is linked to glutamine metabolism, the present invention can have an important impact in cancer therapeutics.

The present invention is directed to overcoming these and other deficiencies in the art.

SUMMARY OF THE INVENTION

A first aspect of the present invention relates to a compound, or a pharmaceutically acceptable salt, ester, enol ether, enol ester, solvate, hydrate, or prodrug thereof, wherein the compound is a compound of Formula I:

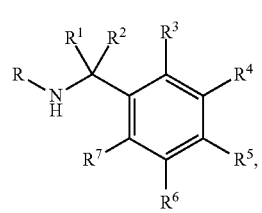

wherein:
R is selected from the group consisting of monocyclic or bicyclic aryl, monocyclic or bicyclic heteroaryl, and monocyclic or bicyclic heterocyclyl, wherein each monocyclic or bicyclic aryl, monocyclic or bicyclic heteroaryl, and monocyclic or bicyclic heterocyclyl can be optionally substituted from 1 to 4 times with substituents independently selected at each occurrence thereof from the group consisting of H, halogen, $C_{1-6}$ alkyl, aryl, $-OR^8$, $-CF_3$, and $-CHF_2$;

$R^1$ and $R^2$ are each independently selected from the group consisting of H, halogen, and $C_{1-6}$ alkyl; or $R^1$ and $R^2$ are combined to form =O;

$R^3$-$R^7$ are each independently selected from the group consisting of H, halogen, $-NO_2$, $-NR^8R^9$, $-SO_2NR^8R^9$, $-N_3$, $-C(O)R^8$, aryl, heteroaryl, heterocyclyl,

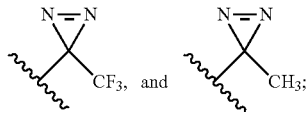 [SMILES: *C1(C(F)(F)F)N=N1 ; "and" ; *C1(C)N=N1]

$R^8$ and $R^9$ are each independently selected from the group consisting of H, $C_{1-6}$ alkyl, $C_{2-6}$ alkenyl, $C_{2-6}$ alkynyl, and aryl; or $R^8$ and $R^9$ are combined with the nitrogen to which they are attached to form a heterocyclyl, wherein the heterocyclyl can be optionally substituted with $-COOH$ or $-COOMe$; and wherein the compound is optionally modified to include a tag and/or an attachment to a solid surface.

A second aspect of the present invention relates to a compound, or a pharmaceutically acceptable salt, ester, enol ether, enol ester, solvate, hydrate, or prodrug thereof, wherein the compound is a compound of Formula II:

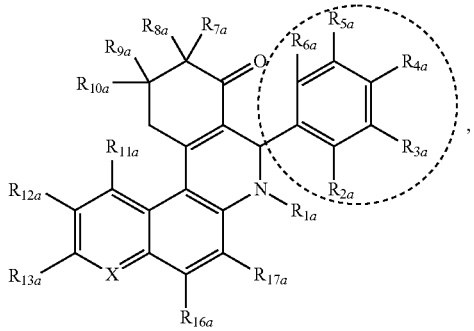

wherein:
the dotted circle identifies an active moiety;
X is independently —CR$_{14a}$— or —N;
R$_{1a}$ is independently H, —OH, —OR$_{14a}$, C$_1$-C$_6$ alkyl, C$_2$-C$_6$ alkenyl, C$_2$-C$_6$ alkynyl, R$_{14a}$C(O)—, R$_{14a}$OC(O)—, R$_{14a}$S(O)—, or R$_{14a}$S(O)$_2$—;
R$_{2a}$, R$_{3a}$, R$_{4a}$, R$_{5a}$, and R$_{6a}$ are each independently a photoreactive moiety, H, halogen, —NO$_2$, —OH, —OR$_{14a}$, —SR$_{14a}$, —NH$_2$, —NHR$_{14a}$, —NR$_{14a}$R$_{15a}$, R$_{14a}$C(O)—, R$_{14a}$OC(O)—, R$_{14a}$C(O)O—, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; or R$_{2a}$ and R$_{3a}$, R$_{3a}$ and R$_{4a}$, R$_{4a}$ and R$_{5a}$, or R$_{5a}$ and R$_{6a}$ are combined to form a heterocyclic ring optionally substituted with a photoreactive moiety;
R$_{7a}$, R$_{8a}$, R$_{9a}$, and R$_{10a}$ are each independently a photoreactive moiety, H, —OH, —NH$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the aryl, heteroaryl, and aryl C$_1$-C$_6$ alkyl are optionally substituted from 1 to 3 times with substituents selected from the group consisting of, halogen, —OH, —NH$_2$, C$_1$-C$_6$ alkyl, C$_2$-C$_6$ alkenyl, C$_1$-C$_6$ alkoxy, —SH, and C$_1$-C$_6$ thioalkyl, and wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; and
R$_{11a}$, R$_{12a}$, R$_{13a}$, R$_{14a}$, R$_{15a}$, R$_{16a}$, and R$_{17a}$ are each independently a photoreactive moiety, H, halogen, —OH, —NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, wherein the alkyl, alkenyl, alkynyl, cycloalkyl, cycloalkylalkyl, arylalkyl, and mono or polycyclic aryl are optionally substituted with a photoreactive moiety and each one of R$_{11a}$-R$_{17a}$ is optionally substituted with —NH$_2$, —OH, halogen, —COOH, —NO$_2$, and —CN;
wherein the compound comprises at least one photoreactive moiety; and
wherein the compound is optionally modified to include a tag and/or an attachment to a solid surface.

A third aspect of the present invention relates to a compound, or a pharmaceutically acceptable salt, ester, enol ether, enol ester, solvate, hydrate, or prodrug thereof, wherein the compound is a compound of Formula III:

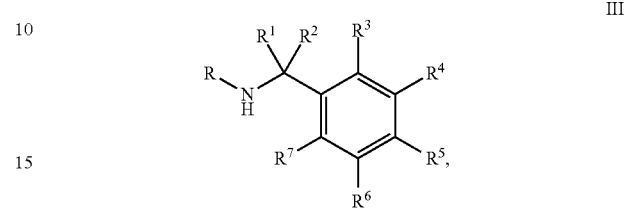

wherein:
R is selected from the group consisting of monocyclic or bicyclic aryl, monocyclic or bicyclic heteroaryl, and monocyclic or bicyclic heterocyclyl, wherein each monocyclic or bicyclic aryl, monocyclic or bicyclic heteroaryl, and monocyclic or bicyclic heterocyclyl can be optionally substituted from 1 to 4 times with substituents independently selected at each occurrence thereof from the group consisting of H, halogen, C$_{1-6}$ alkyl, aryl, —OR$^8$, —CF$_3$, and —CHF$_2$;
R$^1$ and R$^2$ are each independently selected from the group consisting of a photoreactive moiety, H, halogen, and C$_{1-6}$ alkyl optionally substituted with a photoreactive moiety; or R$^1$ and R$^2$ are combined to form =O;
R$^3$-R$^7$ are each independently selected from the group consisting of a photoreactive moiety, H, halogen, —NO$_2$, —NR$^8$R$^9$, —SO$_2$NR$^8$R$^9$, —N$_3$, —C(O)R$^8$, aryl, heteroaryl, and heterocyclyl, wherein the aryl and heteroaryl are optionally substituted with a photoreactive moiety; and
R$^8$ and R$^9$ are each independently selected from the group consisting of a photoreactive moiety, H, C$_{1-6}$ alkyl, C$_{2-6}$ alkenyl, C$_{2-6}$ alkynyl, and aryl, wherein the alkyl, alkenyl, alkynyl, and aryl are optionally substituted with a photoreactive moiety; or R$^8$ and R$^9$ are combined with the nitrogen to which they are attached to form a heterocyclyl, wherein the heterocyclyl can be optionally substituted with a photoreactive moiety, —COOH, or —COOMe;
wherein the compound comprises at least one photoreactive moiety; and
wherein the compound is optionally modified to include a tag and/or an attachment to a solid surface.

A fourth aspect of the present invention relates to a pharmaceutical composition comprising a compound of Formula I, Formula II, or Formula III, or a pharmaceutically acceptable salt, ester, enol ether, enol ester, solvate, hydrate, or prodrug thereof.

A fifth aspect of the present invention relates to a method of reducing the production of glutamate from glutamine in a sample. This method involves inhibiting glutaminase GLS1 activity in the sample by providing a compound and contacting glutaminase GLS1 in the sample with the compound to reduce the production of glutamate from glutamine in the sample, wherein the compound is a compound of Formula I, Formula II, or Formula III, or a pharmaceutically acceptable salt, ester, enol ether, enol ester, solvate, hydrate, or prodrug thereof.

A sixth aspect of the present invention relates to a method of treating a subject with a condition mediated by production of glutamate from glutamine by glutaminase GLS1. The method includes selecting a subject with a condition mediated by production of glutamate from glutamine by glutaminase GLS1 and administering to the selected subject an inhibitor of glutaminase GLS1 activity under conditions effective to treat the condition mediated by production of glutamate from glutamine, wherein the inhibitor is a compound of Formula I, Formula II, or Formula III, or a pharmaceutically acceptable salt, ester, enol ether, enol ester, solvate, hydrate, or prodrug thereof.

A seventh aspect of the present invention relates to methods that involve the formation of a conjugate between a compound and glutaminase GLS1 protein. One embodiment of this aspect of the present invention relates to a method of detecting glutaminase GLS1 protein in a sample. This embodiment involves providing a sample potentially containing glutaminase GLS1 protein; contacting the sample with a compound comprising a photoreactive moiety; exposing the compound to a light source under conditions effective to form a conjugate between the compound and glutaminase GLS1 protein, if present in the sample, through covalent modification of the photoreactive moiety; and detecting whether any compound-glutaminase GLS1 protein conjugates are formed, wherein formation of a compound-glutaminase GLS1 protein conjugate indicates the presence of glutaminase GLS1 protein in the sample; and wherein the compound is a compound of Formula II or III, or a pharmaceutically acceptable salt, ester, enol ether, enol ester, solvate, hydrate, or prodrug thereof. Another embodiment of this aspect of the present invention relates to a method of producing a glutaminase inhibitor-glutaminase GLS1 protein conjugate in a sample. This embodiment involves providing a sample containing one of (i) glutaminase GLS1 protein and (ii) a compound comprising a photoreactive moiety; contacting the sample with the other of (i) glutaminase GLS1 protein and (ii) a compound comprising a photoreactive moiety; and exposing the compound to a light source under conditions effective to form a conjugate between the compound and glutaminase GLS1 protein through covalent modification of the photoreactive moiety; wherein the compound is a compound of Formula II or III, or a pharmaceutically acceptable salt, ester, enol ether, enol ester, solvate, hydrate, or prodrug thereof.

BRIEF DESCRIPTION OF THE DRAWINGS

FIG. 1A shows fluorescent staining before (+Dox) and after (−Dox) a 24-hour induction of Dbl-inducible MEFs with anti-actin (top) and anti-HA (bottom) antibodies. FIG. 1B shows that expression of Dbl confers the ability of MEFs to form foci, which is blocked by treatment with 10 μM 968. FIG. 1C is a diagram showing $^{13}C$ enrichment from [U-$^{13}C$]-glutamine into TCA cycle intermediates, where GAC activation downstream from Dbl is highlighted. $^{13}C$-carbons are shown as dark-filled circles and $^{12}C$-carbons as light-filled circles. FIG. 1D shows glutamine-derived metabolites (glutamate M+5, fumarate M+4, malate M+4, citrate M+4) normalized to $^{13}C$ enrichment observed for MEFs not expressing Dbl. Comparisons were made between treatment with 968, its less potent analog 27, and untreated cells. Bars represent the mean (±SD) of triplicate determinations. P-values were determined by the Students t-test (*p<0.05, **p<0.005).

FIGS. 2A-H are histograms (FIGS. 2A and 2C-H) and a $^{13}C$ enrichment diagram (FIG. 2B) relating to the measured isotopologues of TCA cycle intermediates derived from [U-$^{13}C$]glutamine or [U-$^{13}C$]glucose in non-induced and induced Dbl-MEFs with 968 and 27 treatment. FIG. 2A shows that 968 treatment (8 μM) causes a modest decrease in glutamate pool sizes in non-induced and induced cells while having no effect on the pool sizes of fumarate, malate, and citrate. Metabolites were quantified by normalizing the integrated peaks for all mass isotopologues with respect to the internal standard (50 nmol of 2-oxobutyrate) and protein content. FIG. 2B shows the incorporation of glucose- and glutamine-derived carbon into TCA cycle intermediates. Glutamine-derived carbons are shown as dark-filled circles and glucose derived carbons as light-filled circles. FIGS. 2C-F show isolated and quantified TCA cycle isotopologues following a 1 hour incubation of Dbl-MEFs with [U-$^{13}C$]-glutamine in both the induced (−DOX) and non-induced states (+DOX), with overnight treatment of 8 μM 968, 27 or DMSO control to illustrate effects on glutamine metabolism (+)/(−) DOX as well as with drug treatments. [U-$^{13}C$] glutamine enrichment is noted in the M+5 isotopologue of glutamate (FIG. 2C), M+4 of fumarate (FIG. 2D), M+4 of malate (FIG. 2E), and M+4 of citrate (FIG. 2F), where an inhibition of glutamine metabolism by 968 was observed in both induced and non-induced cells as read out by $^{13}C$ enrichment. FIGS. 2G-H show isolated and quantified citrate isotopologues following incubation of [U-$^{13}C$]glucose in Dbl-MEFs in both the induced and non-induced states to illustrate the effects of Dbl-induction on glucose fueled anaplerosis both over time and with drug treatments. FIG. 2G shows the kinetics of [U-$^{13}C$]glucose enrichment of the TCA cycle intermediate citrate in the induced and non-induced states as read out by the increase of M+2 over time. FIG. 2H shows 968 inhibition of [U-$^{13}C$]glucose enrichment in the M+2 isotopologue of citrate following an 8 hour incubation of Dbl-MEFs with [U-$^{13}C$]glucose in the induced and noninduced states, with overnight treatment of 8 μM 968 and 27; this is thought to be due to the inhibition of glutamine derived TCA cycle intermediates being incorporated into the primary substrate of glucose incorporation into the TCA cycle, oxaloacetate (OAA).

FIGS. 3A-F are a schematic diagram (FIG. 3A) and graphs (FIGS. 3B-F) that relate to a real-time fluorescence assay for detecting GAC tetramer formation. FIG. 3A is a schematic depiction of the FRET assay. FIG. 3B shows that 25 nM 488-GAC (donor) fluorescence is quenched upon addition of QSY9-GAC (acceptor) in a dose-dependent manner and reversed with the addition of a 10-fold excess of unlabeled GAC. FIG. 3C shows FRET resulting from the titration of 25 nM 488-GAC with increasing amounts of QSY9-GAC (open circles) overlaid with concentration-dependent in vitro activation of GAC (closed circles). FRET data was fit to a quadratic binding isotherm. Points represent the mean±SD of three independent experiments. FIG. 3D shows increasing amounts of BPTES added to 25 nM 488-GAC and 25 nM QSY9-GAC to examine the effects of the inhibitor on GAC tetramer formation. A 10-fold excess of unlabeled GAC was added to attempt to reverse tetramer formation. FIG. 3E shows that 968 induces a dose-dependent quenching of 488-GAC fluorescence that is distinct from the quenching induced by the addition of QSY9-GAC. FIG. 3F shows fluorescence quenching upon addition of different concentrations of 968 to 10 nM 488-GAC in the absence of QSY9-GAC.

FIG. 4 is a graph showing quenching of 20 nM 488-labeled GAC fluorescence by 968 (•) and inhibition of 20 nM unlabeled WT GAC as measured by NADH fluorescence emission (○), as described for FIG. 5A, where unlabeled WT GAC (20 nM) was assayed in place of 488-labeled GAC.

FIGS. 5A-E relate to the development of real-time 968 binding and inhibition assays. FIG. 5A is a schematic model of real-time 968 binding and inhibition assays. Monitoring 488-GAC fluorescence quenching serves as a read-out for 968 binding, and enzymatic activity is monitored through the generation of NADH fluorescence upon addition of 20 mM glutamine and 50 mM phosphate to an assay incubation containing labeled GAC together with 10 units of glutamate dehydrogenase (GDH) and 2 mM NAD+. FIG. 5B is a graph of fluorescence of 10 nM 488-GAC (520 nm emission, "a" curves) monitored upon addition of 20 μM 968 (-), 10 μM BPTES (•••), or DMSO (---) at the indicated time. Simultaneously, NADH fluorescence (460 nm emission, "b" curves) was monitored following the addition of 20 mM glutamine and 50 mM phosphate at 120 seconds. FIG. 5C is a graph of real-time 968 binding and inhibition assays adapted to a 96-well plate format and shows overlapping inhibition and fluorescence quenching profiles for 10 nM 488-GAC and 10 nM wild-type (WT) unlabeled GAC. Data points are the average±SD of three independent experiments. The solid line shows the semi-log plot of the binding isotherm with $K_D$=3 μM. FIG. 5D shows the structures of 968 and 968-like analogues used in real-time binding and inhibition assays. FIG. 5E shows plotted $IC_{50}$ (±SD) values from inhibition data and measured $K_D$ (±SD) values from fluorescence quenching data for a representative group of 968 analogues (depicted in FIG. 5D). The compounds a-i correspond to the letter designations shown in FIG. 5D. Values obtained from inhibition data and quenching data were fit to a ligand binding equation for a biomolecular interaction. The line represents a linear regression fit with the following values: $R^2$=0.92, slope=1.10.

FIGS. 6A-D show that binding of 968 is not affected by pretreatment of GAC with the allosteric activator inorganic phosphate whereas its inhibitory potency is markedly reduced. FIG. 6A is a cartoon model of the FRET and 968-binding assays. FIG. 6B is an emission spectra that shows that relative fluorescence emission of 25 nM 488-GAC, in the presence (broken-dotted line) or absence (solid and broken lines) of 100 mM $P_i$, is quenched upon addition of 25 nM QSY9-GAC. 488-GAC fluorescence emission was further quenched upon addition of 10 μM 968, compared to the DMSO control, as a result of 968 binding. As shown in FIGS. 6C-D, 10 nM 488-GAC was assayed for 968 binding (quantified in FIG. 6C) and inhibition (quantified in FIG. 6D), using the assays depicted in FIG. 6A, where 50 mM $P_i$ was added either prior to, or after, 968 addition. Data points represent the average (±SD) of 3 independent experiments, and were fit to a ligand binding equation for a biomolecular interaction.

FIGS. 7A-G relate to the examination of 968 binding to monomeric and dimeric GAC mutants. FIG. 7A shows the crystal structure of the GAC tetramer (human isoform) in complex with both BPTES and glutamate (PDB 3UO9), with the proposed 968-binding pocket indicated by the arrow pointing toward the C-terminal monomer-monomer interface. Insets highlight critical monomer-monomer (top) and dimer-dimer (bottom) contacts, with the corresponding human and mouse GAC isoform residue numbering. FIG. 7B shows multi-angle light scattering profiles of WT GAC (a), D391K-GAC (b), and K316E-D391K-R459E-GAC (c), 250 μg (each), where the solid line represents the elution of each species by monitoring refractive index (R.I.), and the broken line designates the calculated molecular weight for the species eluted at that time. Reference lines for the molecular weights of the monomeric, dimeric, and tetrameric forms of the enzyme are included at 58 kD, 116 kD, and 232 kD respectively. FIGS. 7C-D show that dimeric and monomeric GAC mutants are inactive in the presence and absence of inorganic phosphate. FIGS. 7C-D are graphs of concentration-dependent enzymatic activities of WT GAC, dimeric GAC (D391K), and monomeric GAC (D391K, K316E, R459E), without addition of phosphate (FIG. 7C) and with the addition of 100 mM phosphate (FIG. 7D). Activities were measured in a 2-step end-point activity assay where GAC was incubated in the presence of glutamine for 2 minutes at concentrations under 250 nM GAC, and for 30 seconds at concentrations above 250 nM GAC. Points represent the average (±SD) of 3 independent experiments. FIG. 7E shows FRET assays upon addition of 200 nM WT QSY9-labeled GAC (a), the dimeric QSY9-GAC (D391K) (b), and monomeric QSY9-GAC (K316E, D391K, R459E) (c) to 20 nM WT 488-labeled GAC. FIG. 7F shows 968 binding monitored by its quenching of the fluorescence of WT 488-labeled GAC, dimeric 488-GAC (D391K), and the monomeric GAC (K316E, D391K, R459E) (10 nM total monomer in each sample). Data points represent the mean (±SD) of three independent experiments, and were fit as in FIG. 5C. FIG. 7G shows in vitro inhibition curves of 50 nM (closed circles) and 5 nM WT GAC (open circles) preincubated with increasing concentrations of 968. Data points represent the mean (±SD) of three independent experiments, and were fit to a logistic four parameter curve. Overlaid is the dose dependent inhibition by 968 of Dbl-induced focus formation (triangles).

FIGS. 10A-AJ are graphs showing in vitro quenching and inhibition of GAC for compounds 968, SU-1, SU-2, SU-4, SU-5, SU-7, SU-8, SU-10-SU-36, 031, and 27 respectively.

FIG. 11 is a histogram showing $IC_{50}$s from FIG. 9 ranked in order of potency, including as compared to compound 968.

FIG. 12 shows the correlation between $IC_{50}$ and $K_D$ of the GLS1 inhibitors.

FIGS. 13A-F are graphs showing in vitro quenching and inhibition of 488-KGA for compounds 968, SU-11, SU-14, SU-21, SU-23, and 27, respectively.

FIG. 15 shows the inhibition of various compounds in a proliferation assay in MDA-MB-231 breast cancer cells.

FIGS. 16A-B are graphs of SU-22 quenching and inhibition of 488-GAC following 30 s UV exposure (FIG. 16A) or after 7 minutes of binding with or without UV exposure (FIG. 16B).

FIG. 17 shows SU-22 photo cross linking to GAC in vitro separated using SDS-PAGE and visualized under UV light.

FIGS. 18A-D relate to the purification of SU-22 photo cross linked to GAC in vitro analyzed using gel filtration chromatography and high performance liquid chromatography of peptide fragments following reaction with trypsin. FIG. 18A (top) illustrates the fluorescence of each fraction of the purification protocol for cross linking SU-22 to the K316E/D391K/R459E GAC mutant. Additionally, the total protein in each fraction was visualized using Coomassie blue staining (FIG. 18A (bottom)), further illustrating the purification of the SU-22 labeled species. FIG. 18B is the absorbance trace showing the isolated SU-22 conjugate analyzed using analytical gel filtration. The absorbance trace at 280 nm represents the elution of the protein species and the absorbance trace at 350 nm represents the absorbance of the small molecule, SU-22. FIG. 18C shows the absorbance profile of the isolated SU-22-WT GAC conjugate analyzed using UV-vis spectroscopy, where the absorbance at 350 nm is characteristic of the small molecule SU-22. FIG. 18D shows the HPLC profile of the SU-22-WT GAC conjugate, where the absorbance trace at 254 nm represents any eluted peptides, and the absorbance at 350 nm represents the small molecule SU-22 conjugated peptide (arrow).

DETAILED DESCRIPTION OF THE INVENTION

Figure 1A:
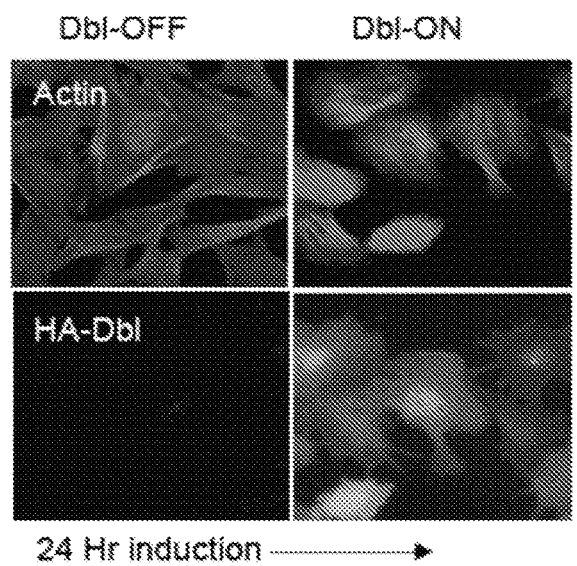
FIGS. 1A-D show that Dbl-induced transformation and increased glutaminolysis are inhibited by 968.

One aspect of the present invention relates to a compound, or a pharmaceutically acceptable salt, ester, enol ether, enol ester, solvate, hydrate, or prodrug thereof, wherein the compound is a compound of Formula I:

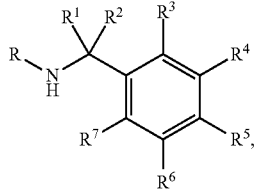

I wherein:
R is selected from the group consisting of monocyclic or bicyclic aryl, monocyclic or bicyclic heteroaryl, and monocyclic or bicyclic heterocyclyl, wherein each monocyclic or bicyclic aryl, monocyclic or bicyclic heteroaryl, and monocyclic or bicyclic heterocyclyl can be optionally substituted from 1 to 4 times with substituents independently selected at each occurrence thereof from the group consisting of H, halogen, $C_{1-6}$ alkyl, aryl, $—OR^8$, $—CF_3$, and $—CHF_2$;

$R^1$ and $R^2$ are each independently selected from the group consisting of H, halogen, and $C_{1-6}$ alkyl; or $R^1$ and $R^2$ are combined to form $=O$;

$R^3$-$R^7$ are each independently selected from the group consisting of H, halogen, $—NO_2$, $—NR^8R^9$, $—SO_2NR^8R^9$, $—N_3$, $—C(O)R^8$, aryl, heteroaryl, heterocyclyl,

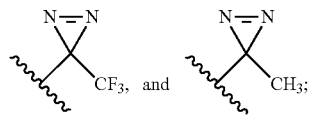

and
$R^8$ and $R^9$ are each independently selected from the group consisting of H, $C_{1-6}$ alkyl, $C_{2-6}$ alkenyl, $C_{2-6}$ alkynyl, and aryl; or $R^8$ and $R^9$ are combined with the nitrogen to which they are attached to form a heterocyclyl, wherein the heterocyclyl can be optionally substituted with —COOH or —COOMe; and wherein the compound is optionally modified to include a tag and/or an attachment to a solid surface.

Another aspect of the present invention relates to a compound, or a pharmaceutically acceptable salt, ester, enol ether, enol ester, solvate, hydrate, or prodrug thereof, wherein the compound is a compound of Formula II:

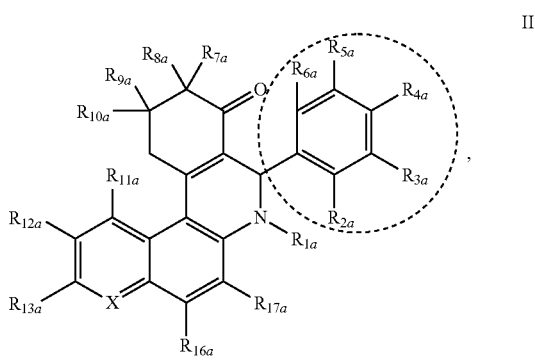

II wherein:
the dotted circle identifies an active moiety;
X is independently $—CR_{14a}—$ or $—N$;
$R_{1a}$ is independently H, $—OH$, $—OR_{14a}$, $C_1$-$C_6$ alkyl, $C_2$-$C_6$ alkenyl, $C_2$-$C_6$ alkynyl, $R_{14a}C(O)—$, $R_{14a}OC(O)—$, $R_{14a}S(O)—$, or $R_{14a}S(O)_2—$;
$R_{2a}$, $R_{3a}$, $R_{4a}$, $R_{5a}$, and $R_{6a}$ are each independently a photoreactive moiety, H, halogen, $—NO_2$, $—OH$, $—OR_{14a}$, $—SR_{14a}$, $—NH_2$, $—NHR_{14a}$, $—NR_{14a}R_{15a}$, $R_{14a}C(O)—$, $R_{14a}OC(O)—$, $R_{14a}C(O)O—$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; or $R_{2a}$ and $R_{3a}$, $R_{3a}$ and $R_{4a}$, $R_{4a}$ and $R_{5a}$, or $R_{5a}$ and $R_{6a}$ are combined to form a heterocyclic ring optionally substituted with a photoreactive moiety;
$R_{7a}$, $R_{8a}$, $R_{9a}$, and $R_{10a}$ are each independently a photoreactive moiety, H, $—OH$, $—NH_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the aryl, heteroaryl, and aryl $C_1$-$C_6$ alkyl are optionally substituted from 1 to 3 times with substituents selected from the group consisting of, halogen, $—OH$, $—NH_2$, $C_1$-$C_6$ alkyl, $C_2$-$C_6$ alkenyl, $C_1$-$C_6$ alkoxy, $—SH$, and $C_1$-$C_6$ thioalkyl, and wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; and $R_{11a}$, $R_{12a}$, $R_{13a}$, $R_{14a}$, $R_{15a}$, $R_{16a}$, and $R_{17a}$ are each independently a photoreactive moiety, H, halogen, —OH, —NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, wherein the alkyl, alkenyl, alkynyl, cycloalkyl, cycloalkylalkyl, arylalkyl, and mono or polycyclic aryl are optionally substituted with a photoreactive moiety and each one of $R_{11a}$-$R_{17a}$ is optionally substituted with —NH$_2$, —OH, halogen, —COOH, —NO$_2$, and —CN;

wherein the compound comprises at least one photoreactive moiety; and wherein the compound is optionally modified to include a tag and/or an attachment to a solid surface.

Another aspect of the present invention relates to a compound, or a pharmaceutically acceptable salt, ester, enol ether, enol ester, solvate, hydrate, or prodrug thereof, wherein the compound is a compound of Formula III:

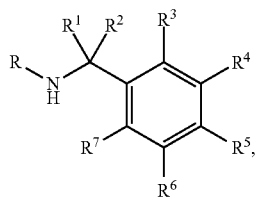

III wherein:

R is selected from the group consisting of monocyclic or bicyclic aryl, monocyclic or bicyclic heteroaryl, and monocyclic or bicyclic heterocyclyl, wherein each monocyclic or bicyclic aryl, monocyclic or bicyclic heteroaryl, and monocyclic or bicyclic heterocyclyl can be optionally substituted from 1 to 4 times with substituents independently selected at each occurrence thereof from the group consisting of H, halogen, C$_{1-6}$ alkyl, aryl, —OR$^8$, —CF$_3$, and —CHF$_2$;

$R^1$ and $R^2$ are each independently selected from the group consisting of a photoreactive moiety, H, halogen, and C$_{1-6}$ alkyl optionally substituted with a photoreactive moiety; or $R^1$ and $R^2$ are combined to form =O;

$R^3$-$R^7$ are each independently selected from the group consisting of a photoreactive moiety, H, halogen, —NO$_2$, —NR$^8$R$^9$, —SO$_2$NR$^8$R$^9$, —N$_3$, —C(O)R$^8$, aryl, heteroaryl, and heterocyclyl, wherein the aryl and heteroaryl are optionally substituted with a photoreactive moiety; and $R^8$ and $R^9$ are each independently selected from the group consisting of a photoreactive moiety, H, C$_1$-C$_6$ alkyl, C$_{2-6}$ alkenyl, C$_{2-6}$ alkynyl, and aryl, wherein the alkyl, alkenyl, alkynyl, and aryl are optionally substituted with a photoreactive moiety; or R$^8$ and R$^9$ are combined with the nitrogen to which they are attached to form a heterocyclyl, wherein the heterocyclyl can be optionally substituted with a photoreactive moiety, —COOH, or —COOMe;

wherein the compound comprises at least one photoreactive moiety; and wherein the compound is optionally modified to include a tag and/or an attachment to a solid surface.

The term "halo" or "halogen" means fluoro, chloro, bromo, or iodo.

The term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substitutents include, without limitation, oxo, thio (i.e. =S), nitro, cyano, halo, OH, NH$_2$, C$_1$-C$_6$ alkyl, C$_1$-C$_6$ alkoxy, C$_2$-C$_6$ alkenyl, C$_2$-C$_6$ alkynyl, C$_3$-C$_6$ cycloalkyl, C$_4$-C$_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two ("bicyclic") or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "thioalkyl" means an alkyl group as described above bonded through a sulfur linkage.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "alkoxy" means an alkyl-O—, alkenyl-O—, or alkynyl-O— group wherein the alkyl, alkenyl, or alkynyl group is described above. Exemplary alkoxy groups include methoxy, ethoxy, n-propoxy, i-propoxy, n-butoxy, pentoxy, and hexoxy.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane.

The term "cycloalkylalkyl" refers to a radical of the formula —R$^a$R$^b$ where R$^a$ is an alkyl radical as defined above and $R^b$ is a cycloalkyl radical as defined above. The alkyl radical and the cycloalkyl radical may be optionally substituted as defined above.

The term "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —$R^aR^b$ where $R^a$ is an alkyl radical as defined above and $R^b$ is an aryl radical as defined above. The alkyl radical and the cycloalkyl radical may be optionally substituted as defined above.

The term "arylarylalkyl" refers to a radical of the formula —$R^aR^bR^c$ where $R^a$ is an alkyl as defined above, $R^b$ is an aryl radical as defined above, and $R^c$ is an aryl radical as defined above. The alkyl radical and both aryl radicals may be optionally substituted as defined above.

The term "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" refers to an aromatic ring radical which consists of carbon atoms and from one to five heteroatoms selected from the group consisting of nitrogen, oxygen, and sulfur. For purposes of this invention the heteroaryl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

Further heterocycles and heteroaryls are described in COMPREHENSIVE HETEROCYCLIC CHEMISTRY: THE STRUCTURE, REACTIONS, SYNTHESIS AND USE OF HETEROCYCLIC COMPOUNDS Vol. 1-8 (Alan R. Katritzky et al. eds., $1^{st}$ ed. 1984), which is hereby incorporated by reference in its entirety.

A "photoreactive moiety" as used herein is a moiety that becomes reactive when exposed to ultraviolet or visible light. Photoreactive moieties for use in the compounds of Formula II and Formula III include, for example, aryl azides, diazirines, and benzophenone.

The compounds of the present invention (or pharmaceutically acceptable salts, esters, enol ethers, enol esters, solvates, hydrates, or prodrugs thereof) can optionally be modified to include a tag. A "tag" as used herein includes any labeling moiety that facilitates the detection, quantitation, isolation, and/or purification of a compound (i.e., a compound of the present invention, a compound-glutaminase GLS1 protein conjugate as described infra, a conjugated compound/inhibitor as described infra, and/or a conjugated glutaminase GLS1 protein as described infra). Methods for modifying small molecules to include tags are well known in the art. For example, click chemistry (see, e.g., U.S. Pat. No. 7,375,234 to Sharpless et al., which is hereby incorporated by reference in its entirety) may be used to attach a tag to a compound.

Suitable tags include purification tags, radioactive or fluorescent labels, enzymatic tags, prosthetic groups, luminescent materials, bioluminescent materials, positron emitting metals, nonradioactive paramagnetic metal ions, and any other signal suitable for detection and/or measurement by radiometric, colorimetric, fluorometric, size-separation, or precipitation means, or other means known in the art.

Purification tags, such as maltose-binding protein (MBP-), poly-histidine ($His_6$-), or a glutathione-S-transferase (GST-), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}$I, $^{123}$I, $^{131}$I, $^{111}$In, $^{112}$In, $^{113}$In, $^{115}$In, $^{99}$TC, $^{213}$Bi, $^{14}$C, $^{51}$Cr, $^{153}$Gd, $^{159}$Gd, $^{68}$Ga, $^{67}$Ga, $^{68}$Ge, $^{166}$Ho, $^{140}$La, $^{177}$Lu, $^{54}$Mn, $^{99}$Mo, $^{103}$Pd, $^{32}$P, $^{142}$Pr, $^{149}$Pm, $^{186}$Re, $^{188}$Re, $^{105}$Rh, $^{97}$Ru, $^{153}$Sm, $^{47}$Sc, $^{75}$Se, $^{85}$Sr, $^{35}$S, $^{201}$Ti, $^{113}$Sn, $^{117}$Sn, $^{3}$H, $^{133}$Xe, $^{169}$Yb, $^{175}$Yb, $^{90}$Y, and $^{65}$Zn. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Further examples include positron emitting metals using various positron emission tomographies, and nonradioactive paramagnetic metal ions.

Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, Texas Red, and umbelliferone. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme—Antibody Conjugates for Use in Enzyme Immunoassay, in METHODS IN ENZYMOLOGY 147-66 (Langone et al. eds., 1981), which is hereby incorporated by reference in its entirety.

Prosthetic group complexes include, but are not limited to, streptavidin/biotin and avidin/biotin. Alternatively, the compound can be conjugated to a luminescent or bioluminescent material including, but not limited to, luminol, luciferase, luciferin, and aequorin.

The compounds of the present invention (or pharmaceutically acceptable salts, esters, enol ethers, enol esters, solvates, hydrates, or prodrugs thereof) can optionally be modified to include an attachment to a solid surface, such as a fibrous test strip, a column, a multi-well microliter plate, a test tube, or beads. Methods for attaching small molecules to such surfaces, including covalent attachment (for example via click chemistry, as described supra) as well as non-covalent attachment through the use of antibody-antigen partners, complementary nucleic acids, etc., are well known in the art.

Pharmaceutically acceptable salts include, but are not limited to, amine salts, such as but not limited to, N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts, such as but not limited to, lithium, potassium, and sodium; alkali earth metal salts, such as but not limited to, barium, calcium, and magnesium; transition metal salts, such as but not limited to, zinc; and other metal salts, such as but not limited to, sodium hydrogen phosphate and disodium phosphate; and also including, but not limited to, salts of mineral acids, such as but not limited to, hydrochlorides and sulfates; and salts of organic acids, such as but not limited to, acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C═C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C═C (OC (O) R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

Exemplary Formula I compounds of the present invention include, without limitation, any of the following GLS1 inhibitors (and pharmaceutically acceptable salts or produgs thereof, and optionally modified to include a tag and/or an attachment to a solid surface).

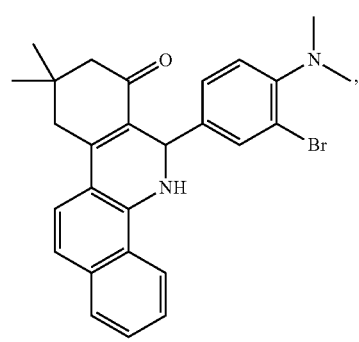

SU-1

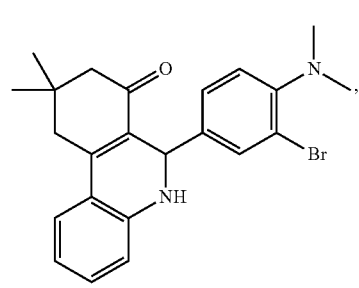

SU-2

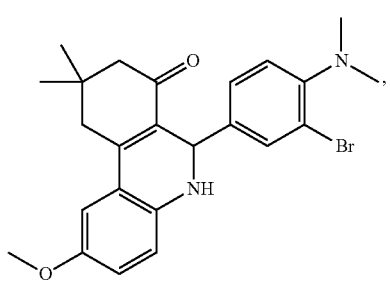

SU-3

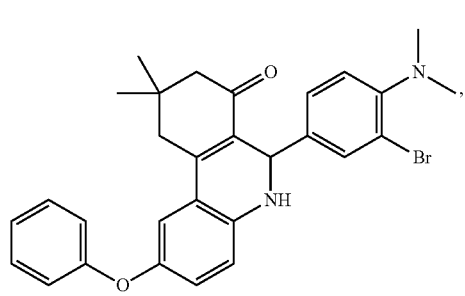

SU-4

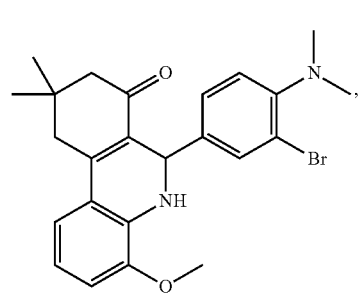

SU-5

SU-6
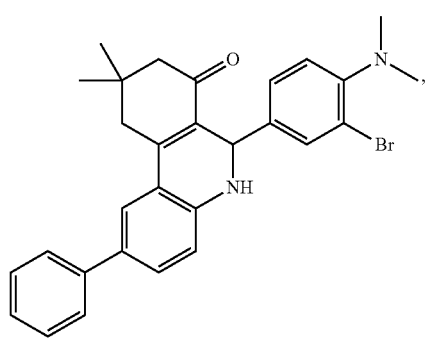
SU-7
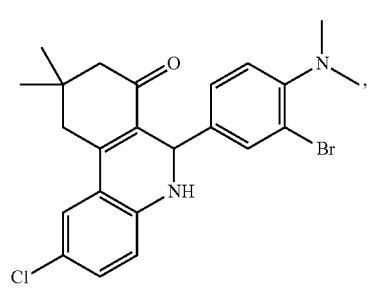
SU-8
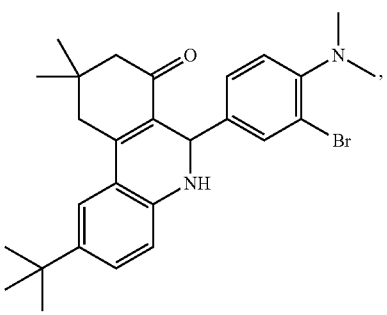
SU-9
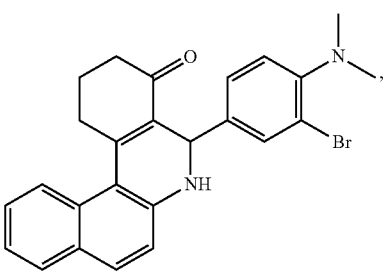
SU-10
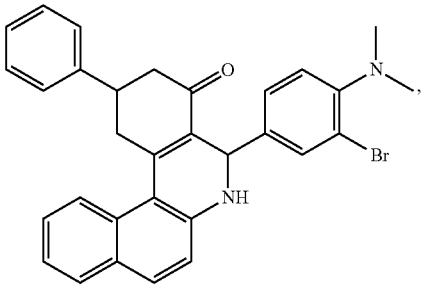
SU-11
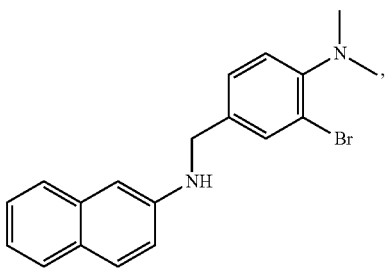
SU-12
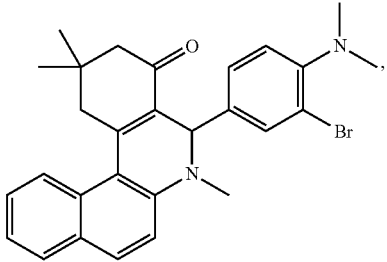
SU-13
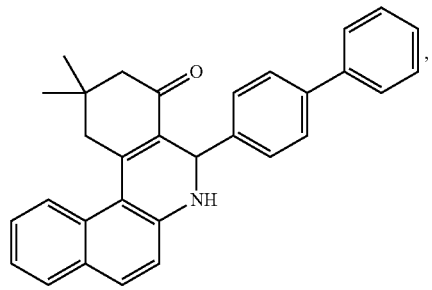
SU-14
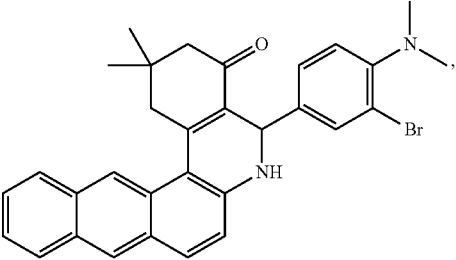
SU-15
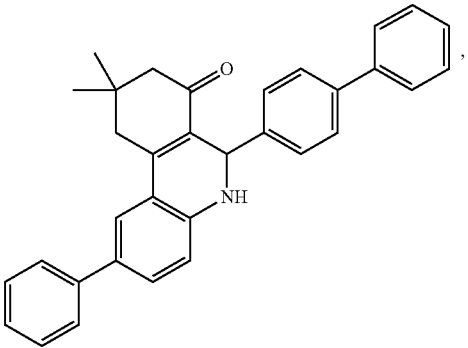

SU-16
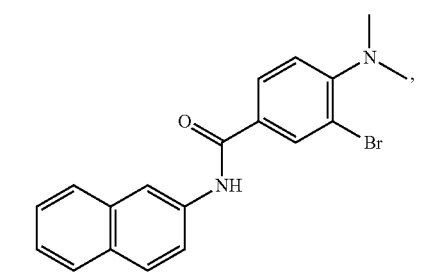
SU-17
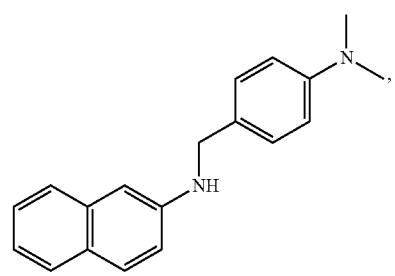
SU-18
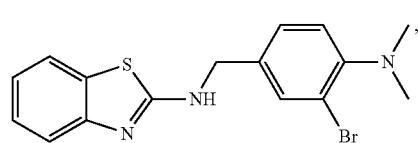
SU-19
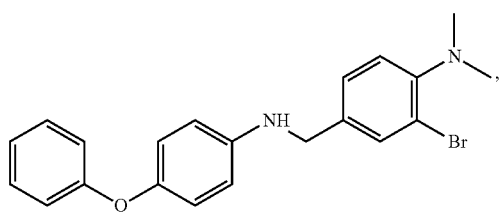
SU-20
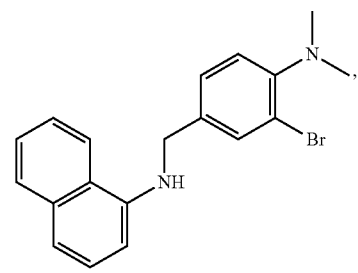
SU-21
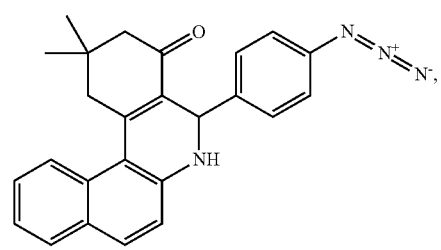
SU-22
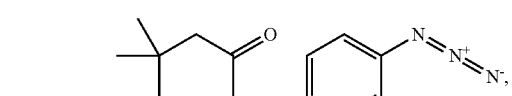
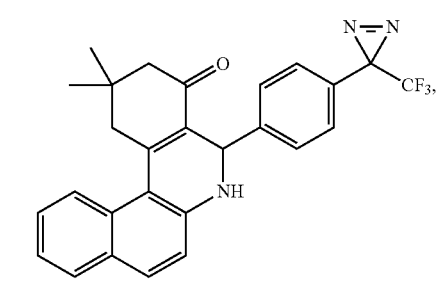
SU-23
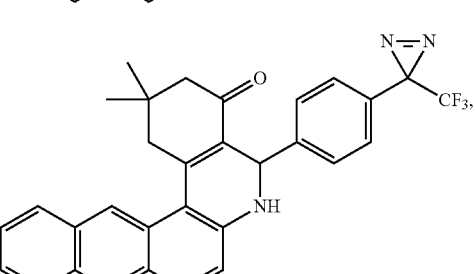
SU-24
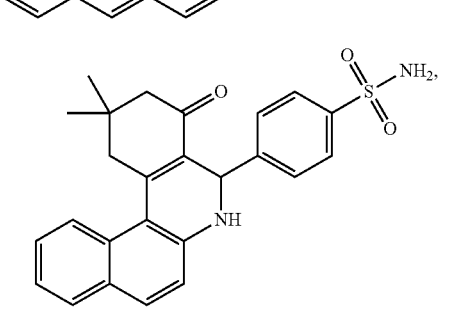
SU-25
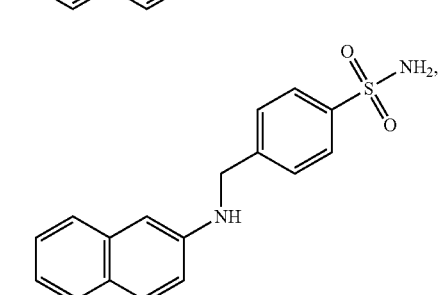
SU-26
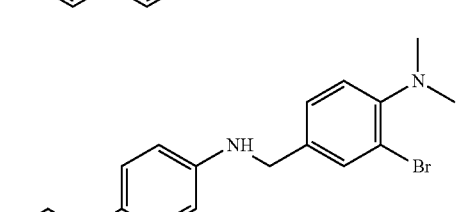
SU-27
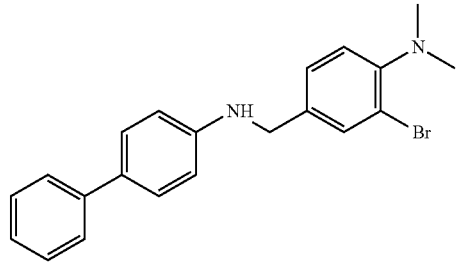

SU-28 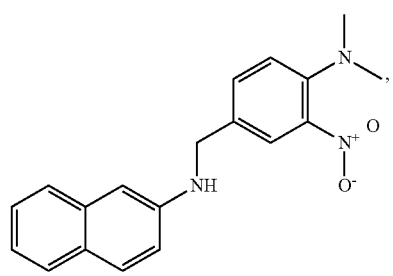

SU-29 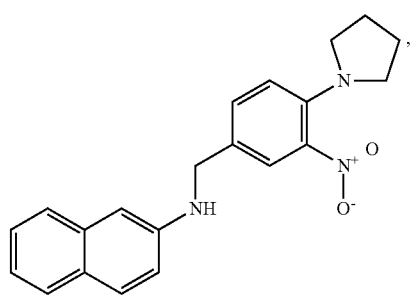

SU-30 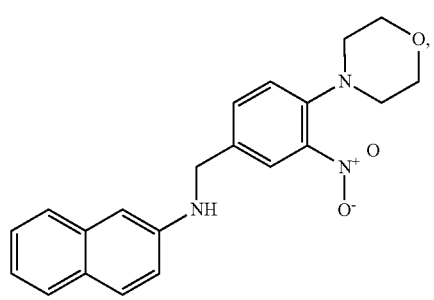

SU-31 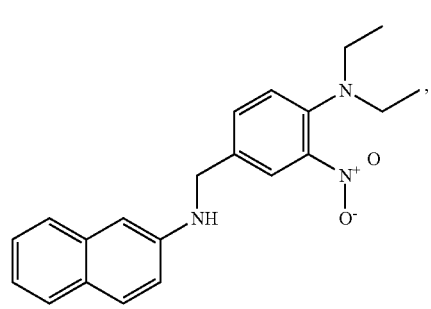

SU-32 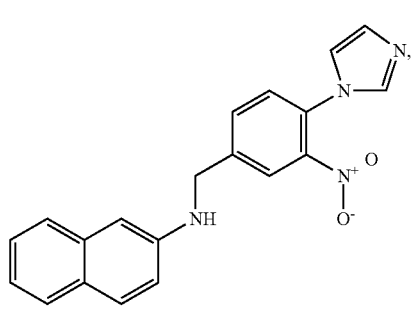

SU-33 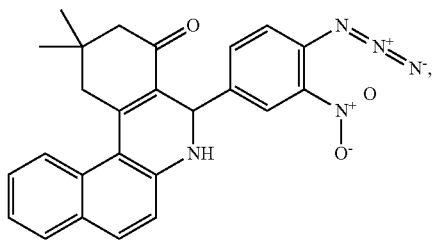

SU-34 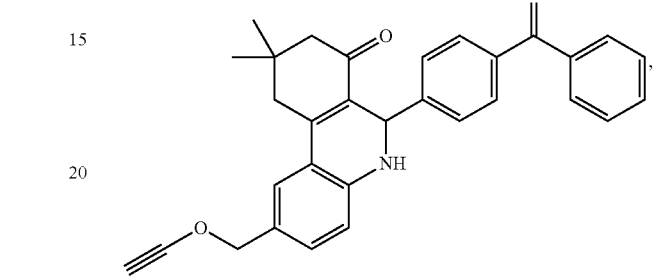

SU-35 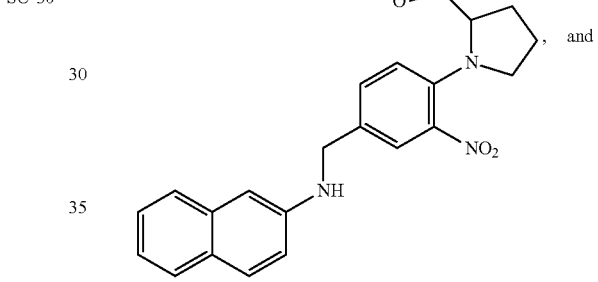

SU-36 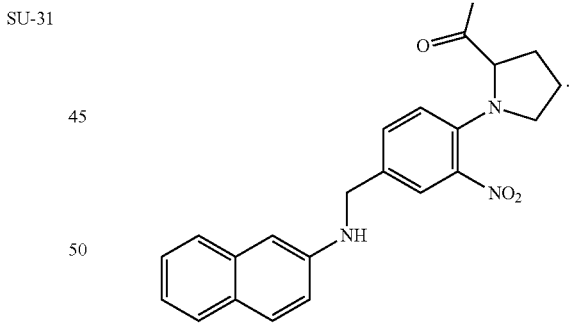

In a preferred embodiment, the compound of Formula I is selected from the group consisting of SU-11, SU-14, SU-16, SU-17, SU-18, SU-19, SU-20, SU-21, SU-22, SU-23, SU-24, SU-25, SU-26, SU-27, SU-28, SU-29, SU-30, SU-31, SU-32, SU-33, SU-34, SU-35, and SU-36 (and pharmaceutically acceptable salts or produgs thereof, and optionally modified to include a tag and/or an attachment to a solid surface).

In a preferred embodiment, the compound of Formula I is selected from the group consisting of SU-11, SU-16, SU-17, SU-19, SU-20, SU-23, SU-24, SU-26, SU-27, SU-28, SU-29, SU-30, SU-31, SU-32, SU-35, and SU-36 (and pharmaceutically acceptable salts or produgs thereof, and optionally modified to include a tag and/or an attachment to a solid surface).

Exemplary Formula II compounds of the present invention include any of the glutaminase inhibitors disclosed in International Patent Application No. PCT/US10/28688, which is hereby incorporated by reference in its entirety, but being modified to include a photoreactive moiety in accordance with Formula II herein (and pharmaceutically acceptable salts or produgs thereof, and optionally modified to include a tag and/or an attachment to a solid surface).

With respect to compounds of Formula II, suitable active moieties are described in International Patent Application No. PCT/US10/28688, which is hereby incorporated by reference in its entirety, and include the active moieties shown below (optionally modified to include a photoreactive moiety, a tag, and/or an attachment to a solid surface).

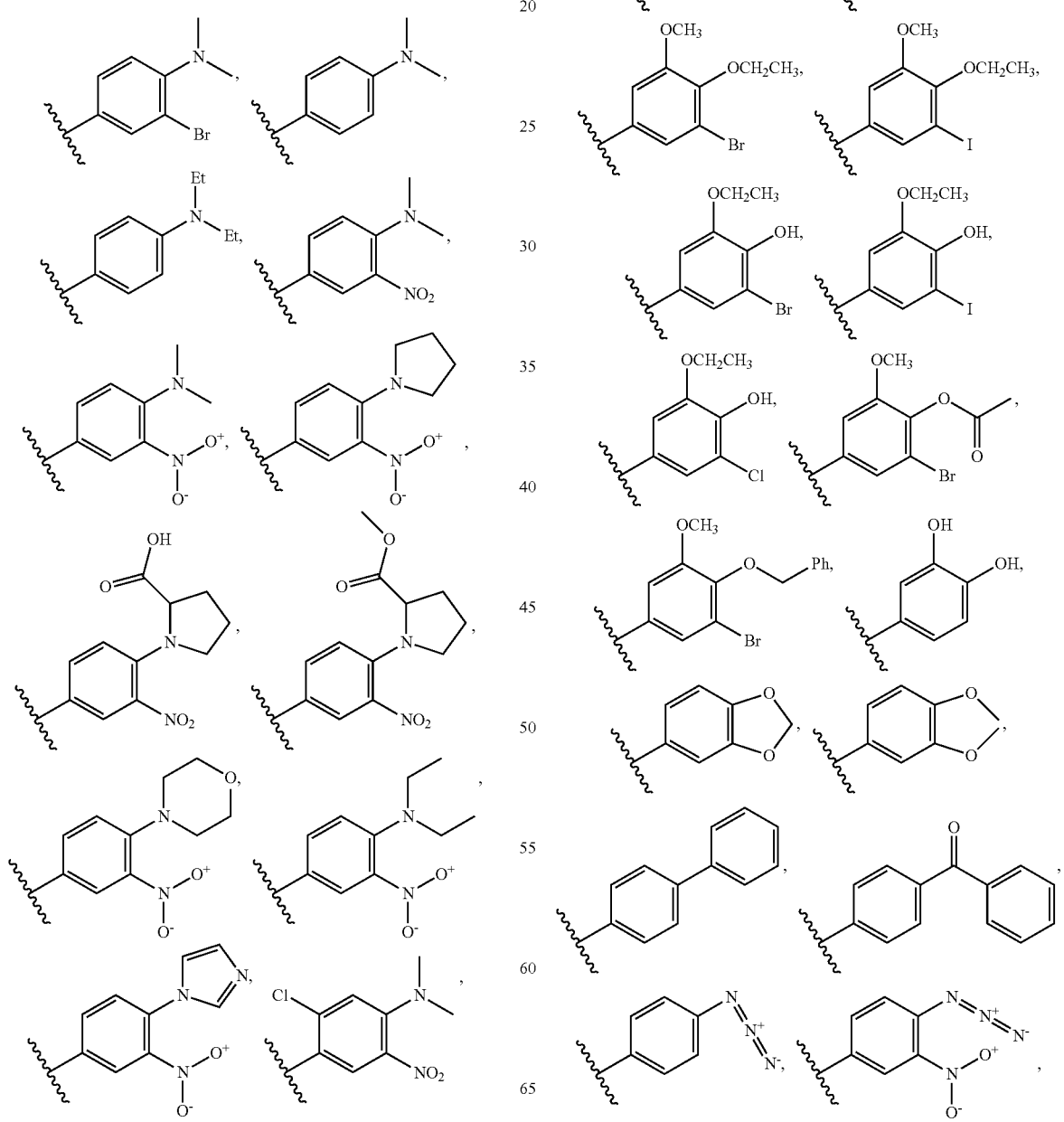

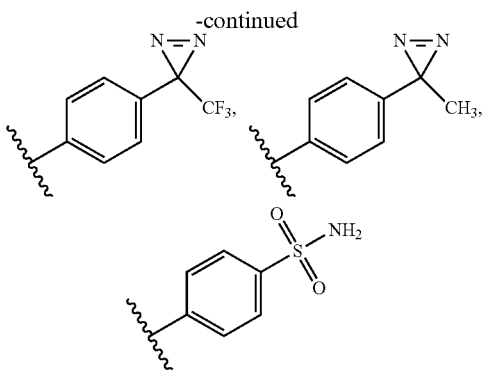

In a preferred embodiment, the active moiety is

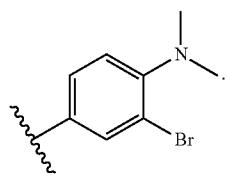 [SMILES: *c1ccc(N(C)C)c(Br)c1]

Exemplary Formula III compounds of the present invention include SU-21, SU-22, SU-23, SU-24, SU-33, and SU-34 (and pharmaceutically acceptable salts or produgs thereof, and optionally modified to include a tag and/or an attachment to a solid surface).

As noted above, photoreactive moieties for use in the compounds of Formula II and Formula III include, for example, aryl azides, diazirines, and benzophenone. Suitable examples include, without limitation, —N=N$^+$=N$^-$;

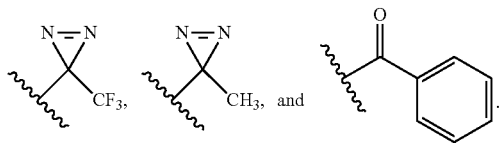 [SMILES: *C1(C(F)(F)F)N=N1 ; *C1(C)N=N1 ; "and" ; *C(=O)c1ccccc1]

As will be apparent to the skilled artisan, aryl azides and benzophenone are attached to an aromatic ring. Thus, when the photoreactive moiety is an aryl azide or benzophenone, it is present in Formula II at the $R_{2a}$-$R_{6a}$, $R_{11a}$, $R_{12a}$, $R_{13a}$, $R_{16a}$, or $R_{17a}$ position and is present in Formula III at the $R_3$-$R_7$ positions.

With respect to Formula II compounds, compounds having a photoreactive moiety in the $R_{2a}$-$R_{6a}$ ring have been shown to be effective. Inhibition assays using 968-like compounds have shown that the $R_{7a}$-$R_{10a}$ ring can tolerate many different substitutions while maintaining efficacy. Thus, it is expected that the photoreactive moiety may be located on this ring as well. In at least one embodiment, the photoreactive moiety is present at the $R_{4a}$ position.

With respect to Formula III compounds, compounds having a photoreactive moiety at the $R^5$ position have been shown to be effective. Inhibition assays using compounds of Formula I, which are structurally similar to those of Formula III, have shown that such compounds can tolerate many different substitutions at the $R^1$-$R^4$, $R^6$, and $R^7$ positions while maintaining efficacy. Thus, it is expected that the photoreactive moiety may be located at these positions as well. In at least one embodiment, the photoreactive moiety is present at the $R^5$ position.

Another aspect of the present invention relates to a pharmaceutical composition comprising a compound of Formula I, Formula II, or Formula III, or a pharmaceutically acceptable salt, ester, enol ether, enol ester, solvate, hydrate, or prodrug thereof.

According to this aspect of the present invention, the pharmaceutical compositions can comprise a compound of the present invention and a pharmaceutically acceptable carrier and, optionally, one or more additional active agent(s) as discussed below.

Numerous standard references are available that describe procedures for preparing various formulations suitable for administering the compounds according to the invention. Examples of potential formulations and preparations are contained, for example, in the HANDBOOK OF PHARMACEUTICAL EXCIPIENTS (American Pharmaceutical Association, current edition), PHARMACEUTICAL DOSAGE FORMS: TABLETS (Lieberman et al. eds., Marcel Dekker, Inc., pubs., current edition), and REMINGTON'S PHARMACEUTICAL SCIENCES 1553-93 (Arthur Osol ed., current edition), which are hereby incorporated by reference in their entirety.

Any pharmaceutically acceptable liquid carrier suitable for preparing solutions, suspensions, emulsions, syrups and elixirs may be employed in the composition of the invention. Compounds of the present invention may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

It will be understood that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

Another aspect of the present invention relates to a method of reducing the production of glutamate from glutamine by glutaminase GLS1 in a sample. This method involves inhibiting glutaminase GLS1 activity in the sample by providing a compound and contacting glutaminase GLS1 in the sample with the compound to reduce the production of glutamate from glutamine in the sample, where the compound is a compound of Formula I, Formula II, or Formula III, or a pharmaceutically acceptable salt, ester, enol ether, enol ester, solvate, hydrate, or prodrug thereof.

The term "reduce" means to suppress, decrease, diminish, or lower the production of glutamate from glutamine.

Suitable samples include those described infra.

In all aspects of the present invention directed to methods involving contacting a sample with one or more compounds, contacting can be carried out using methods that will be apparent to the skilled artisan, and can be done in vitro, ex vivo, or in vivo.

Compounds of the present invention may be delivered directly to a targeted cell/tissue/organ. Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell, including its transport across the blood-brain barrier; and/or to facilitate its uptake by a target cell (e.g., its transport across cell membranes).

In vivo administration can be accomplished either via systemic administration to the subject or via targeted administration to affected tissues, organs, and/or cells, as described above. Typically, the therapeutic agent (i.e., a compound of the present invention) will be administered to a patient in a vehicle that delivers the therapeutic agent(s) to the target cell, tissue, or organ. Typically, the therapeutic agent will be administered as a pharmaceutical formulation, such as those described above.

The compounds of the present invention can be administered, e.g., by intravenous injection, intramuscular injection, subcutaneous injection, intraperitoneal injection, topical application, sublingual, intraarticular (in the joints), intradermal, buccal, ophthalmic (including intraocular), intranasally (including using a cannula), or by other routes. The compounds of formulae I, II, and/or III (as well as compounds comprising their active moieties) can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682, which is hereby incorporated by reference in its entirety) via a liposomal formulation (see, e.g., European Patent No. 736299, WO 99/59550, and WO 97/13500, which are hereby incorporated by reference in their entirety), via formulations described in WO 03/094886, which is hereby incorporated by reference in its entirety, or in some other form. The compounds of the present invention can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., *Nature Reviews Drug Discovery* 3:115 (2004), which is hereby incorporated by reference in its entirety). The compounds can be administered locally, for example, at the site of injury to an injured blood vessel. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in WO 00/45792, WO 00/53160, and WO 02/19989, which are hereby incorporated by reference in their entirety. An example of a transdermal formulation containing plaster and the absorption promoter dimethylisosorbide can be found in WO 89/04179, which is hereby incorporated by reference in its entirety. WO 96/11705, which is hereby incorporated by reference in its entirety, provides formulations suitable for transdermal administration.

For use as aerosols, a compound of the present invention in solution or suspension may be packaged in a pressurized aerosol container together with suitable propellants, for example, hydrocarbon propellants like propane, butane, or isobutane with conventional adjuvants. The compounds of the present invention also may be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-Cell-Specific Delivery and Controlled Expression of a Foreign Gene in Mouse," *Proc. Nat'l Acad. Sci. USA* 84:7851-55 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the compound to the desired organ, tissue, or cells in vivo to effect this aspect of the present invention.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the compound of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The compounds of the present invention can be administered alone or as an active ingredient of a pharmaceutical formulation, such as those described above. The compounds of the present invention can be administered in a form where the active ingredient is substantially pure.

Another aspect of the present invention relates to a method of treating a subject with a condition mediated by production of glutamate from glutamine. The method involves selecting a subject with a condition mediated by production of glutamate from glutamine and administering to said selected subject an inhibitor of GLS1 activity under conditions effective to treat the condition mediated by production of glutamate from glutamine. In this aspect of the present invention, the inhibitor of GLS1 activity is a compound of Formula I, Formula II, or Formula III, or a pharmaceutically acceptable salt, ester, enol ether, enol ester, solvate, hydrate, or prodrug thereof.

The term "treatment" or "treating" means any manner in which one or more of the symptoms of a disease or disorder are ameliorated or otherwise beneficially altered. Treatment also encompasses any pharmaceutical use of the compositions herein, such as use for treating diseases or disorders mediated by the production of glutamate from glutamine.

Splice isoforms, namely kidney-type glutaminase (KGA) and isoform C (GAC) of the Gls1 gene (gene locus 2q32-q34) represent the translated forms of the human kidney-type glutaminase or GLS1, an enzyme found in abundance in proliferating cells, immune cells, kidney, brain, muscle, and other tissues, and is generally referred to here throughout as GLS1. Gls1 gene products are involved in the hydrolysis of glutamine to glutamate and ammonium.

In one embodiment, this aspect of the present invention can be carried out by inhibiting overexpression-independent GLS1 activity and/or inhibiting GLS1 activity independent of exogenous phosphate addition. Alternatively, an activating phosphorylation event on GLS1 can be inhibited. As a further alternative of the method of the present invention, inhibition of GLS1 activity can be performed by inhibiting GLS1 hyperactivity.

Although GLS1 expression has been found to be increased in some cancers, applicants have found that the participation of GLS1 is not limited to an increase in expression. Some cancer cells (such as the breast cancer cell line SKBR3) have been found to exhibit a particular splice isoform of GLS1 (GAC) expression levels which are similar to normal cells, but are still dependent on the presence of GLS1 for cell growth (see, e.g. WO 10/111504, which is hereby incorporated by reference in its entirety). Thus, by reducing the normal expression levels of this splice isoform of GLS1, one can inhibit kidney-type glutaminase activity in cancer cells.

GLS1 isolated from cancer cells can show an elevated glutaminase activity level relative to GLS1 isolated from normal cells when assayed in the absence of phosphate, but in the presence of phosphate the enzymes isolated from both normal and cancer cells show a similar extent of activation per amount of GLS1 (see, e.g. WO 10/111504, which is hereby incorporated by reference in its entirety). Thus, the GLS1 in cancer cells is not dependent on the exogenous addition of phosphate to be active. Inhibition of the phosphate-independent activation of GLS1 in cancer cells would inhibit the production of glutamate from glutamine.

One way in which the GLS1 activity from cancer cells may be increased relative to the GLS1 activity in normal cells is by a phosphorylation event that occurs on GLS1. If the phosphorylations on GLS1 are removed/blocked using either alkaline phosphate or a small molecule (e.g., compound 968), the ability for GLS1 to produce glutamate from glutamine is limited.

The activation state of GLS1 may vary among different cancer cells, regardless of the expression levels of GLS1. A higher amount of activity may be referred to as "hyperactivity". For example, Dbl transformed cells and Cdc42 F28L transformed cells contain similar levels of GLS1 as do untransformed NIH 3T3 cells. However, the GLS1 in the Dbl and Cdc42 transformed cells shows a higher activation than in the non-transformed cells, with the GLS1 from the Dbl cells being approximately twice as active than the GLS1 from the Cdc42 transformed cells (see, e.g. WO 10/111504, which is hereby incorporated by reference in its entirety). Thus, the GLS1 in the Dbl transformed cells is hyperactive. Inhibiting the hyperactivity of GLS1 in Dbl cells would limit the production of glutamate from glutamine by glutaminase C.

In a preferred embodiment, the glutaminase GLS1 is any translated isoform of Gls1 that exhibits measurable glutamine deamidation activity, i.e. hydrolyses glutamine to produce glutamate and ammonia. This includes GAC and KGA.

Glutaminase inhibitors have been shown to have efficacy in cancers of the breast, brain, lung, ovary, pancreas, colon, and multiple myeloma. It is expected that GLS1 inhibitors of Formula I, Formula II, and Formula III of the present application would show efficacy in these and any other cancer which was glutamine dependent and/or had high GLS1 expression and/or activation. Thus, the conditions mediated by production of glutamate from glutamine according to the present invention include, without limitation, any cancer that exhibits active glutaminase activity, as the result of GLS1 expression and/or activation.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline (e.g., cats) or canine (e.g., dogs) subjects, farm animals, such as but not limited to bovine (e.g., cows), equine (e.g., horses), caprine (e.g., goats), ovine (e.g., sheep), and porcine (e.g., pigs) subjects, wild animals (whether in the wild or in a zoological garden), research animals, such as mice, rats, rabbits, guinea pigs, goats, sheep, pigs, dogs, cats, horses, cows, camels, llamas, monkeys, zebrafish etc., avian species, such as chickens, turkeys, songbirds, etc., i.e., for veterinary medical use.

Administering may be carried out as described supra.

Another aspect of the present invention relates to methods that involve the formation of a conjugate between a compound of Formula II or Formula III and glutaminase GLS1 protein. As will be apparent to the skilled artisan, inhibitor-glutaminase GLS1 protein conjugates can be made using photoreactive glutaminase inhibitor compounds of Formula II and Formula III. Briefly, when the glutaminase inhibitor is allowed to bind to glutaminase GLS1 protein, covalent modification can be initiated by exposing the inhibitor to an appropriate light source, thereby forming the conjugate. The ability to form inhibitor-glutaminase GLS1 protein conjugates can be utilized for the detection, quantitation, separation, and/or purification of the inhibitors and/or the glutaminase GLS1 protein.

One embodiment of this aspect of the present invention relates to a method of detecting glutaminase GLS1 protein in a sample. This method involves providing a sample potentially containing glutaminase GLS1 protein; contacting the sample with a compound comprising a photoreactive moiety; exposing the compound to a light source under conditions effective to form a conjugate between the compound and glutaminase GLS1 protein, if present in the sample, through covalent modification of the photoreactive moiety; and detecting whether any compound-glutaminase GLS1 protein conjugates are formed, wherein formation of a compound-glutaminase GLS1 protein conjugate indicates the presence of glutaminase GLS1 protein in the sample; and wherein the compound is a compound of Formula II or Formula III, or a pharmaceutically acceptable salt, ester, enol ether, enol ester, solvate, hydrate, or prodrug thereof.

Another embodiment of this aspect of the present invention relates to a method of producing a glutaminase inhibitor-glutaminase GLS1 protein conjugate in a sample. This method involves providing a sample containing one of (i) glutaminase GLS1 protein and (ii) a compound comprising a photoreactive moiety; contacting the sample with the other of (i) glutaminase GLS1 protein and (ii) a compound comprising a photoreactive moiety; and exposing the compound to a light source under conditions effective to form a conjugate between the compound and glutaminase GLS1 protein through covalent modification of a photoreactive moiety; wherein the compound is a compound of Formula II or Formula III, or a pharmaceutically acceptable salt, ester, enol ether, enol ester, solvate, hydrate, or prodrug thereof.

As will be apparent to the skilled artisan, once the conjugate is produced, further steps may optionally be carried out to, for example, detect (including imaging), quantitate, isolate, and/or purify the inhibitor and/or glutaminase GLS1 protein. These steps may be used, for example, to identify cells/tissue in which glutaminase GLS1 is present, to determine the subcellular localization of glutaminase GLS1, to monitor glutaminase GLS1 and/or the inhibitor during cellular fractionation, etc. These steps can be facilitated by using an inhibitor that has been appropriately tagged, as described supra.

Detecting and/or quantitating according to all aspects of the present invention include detection and/or measurement by radiometric, colorimetric, fluorometric, size-separation, or precipitation means, or other means known in the art. By way of example, radioactivity can be detected and quantified using a scintillation counter or autoradiography, fluorescence can be detected and quantified using a fluorometer, color changes catalyzed by enzymatic tags can be measured spectrophotometrically. Other methods for detecting and quantifying are well known in the art.

As will be apparent to the skilled artisan, this aspect of the present invention may be carried out in vitro, ex vivo, or in vivo. Contacting may be carried out as described supra.

Suitable samples according to this and all aspects of the present invention include, without limitation, purified proteins, cells, cell extracts, and tissue. Methods involving cell or tissue samples may be carried out using a cell or tissue that is present within a subject, or with a cell or tissue that has been isolated from a subject. Suitable cells and tissues include those of the cancers described supra. Suitable subjects in which the cell/tissue may be contained or from which the cell/tissue may be isolated include the subjects described supra.

EXAMPLES

The following examples are provided to illustrate embodiments of the present invention but are by no means intended to limit its scope.

Example 1

Isogenic, Dbl-Inducible Cell System Culture Conditions and Immunofluorescence Staining Inducible oncogenic Dbl cell lines were created using the TET-OFF system in mouse embryonic fibroblasts (MEFs) following the manufacturer's instructions (Clontech). Briefly, PCR products for onco-Dbl-containing NotI and XbaI restriction endonuclease sites were cloned in the per2.1 vector using the TOPO-TA cloning kit (Invitrogen) and subsequently subcloned into the p-TREHA vector (Clontech). The pTRE-HA-onco-Dbl was then co-transfected with pMET-Puro in a 20:1 ratio into parental MEFs (Clontech), which contained the transcriptional transactivator (tTa), with Lipofectamine (Invitrogen). Cells were placed under puromycin selection at 48 hours post transfection, and colonies were selected after 2-4 weeks for doxycycline-dependent expression of HA-onco-Dbl using HA.11 antibody (Covance). Cells were maintained in DMEM supplemented with 10% (v/v) Tet system-approved FBS (clontech) and 100 µg/mL G418 (Gibco). To suppress Dbl expression, 1 µg/mL doxycycline was added to the medium every 2 days. Cells were induced by re-plating in doxycycline-free medium where residual doxycycline was removed by replacing the medium 3 hours after plating. Immunofluorescence was conducted on cells grown 48-72 hours on glass cover slips and fixed with 3.7% formaldehyde. Fixed cells were permeabilized with 0.2% Triton-X100 and co-stained with α-HA (rabbit polyclonal, Covance) and α-actin (mouse monoclonal, Covance) for 1 hour at 37° C., followed by incubation with Oregon green-conjugated α-rabbit IgG (Molecular Probes) and Rhodamine conjugated α-mouse IgG (molecular probes). Digital images were collected using a Zeiss fluorescence microscope and AxioVision 3.1 software.

Example 2

Metabolic Tracing and Foci Forming Assays

Foci forming assays were performed on Dbl-inducible cell lines in both the induced and noninduced states by mixing with parental MEFs (Clontech) in a 1:4 ratio. Cells were grown to confluence in complete medium and then switched to 5% FBS and grown for 14-21 days. The small molecule inhibitor, 968, was added to examine its ability to inhibit focus formation. Cells were fixed in 3.7% formaldehyde and stained with 0.4% crystal violet in methanol.

Figure 2A:
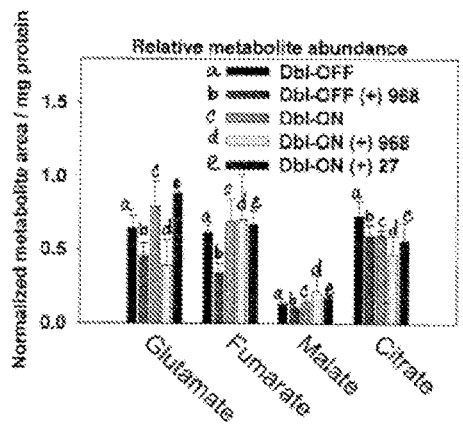
Figure 2B:
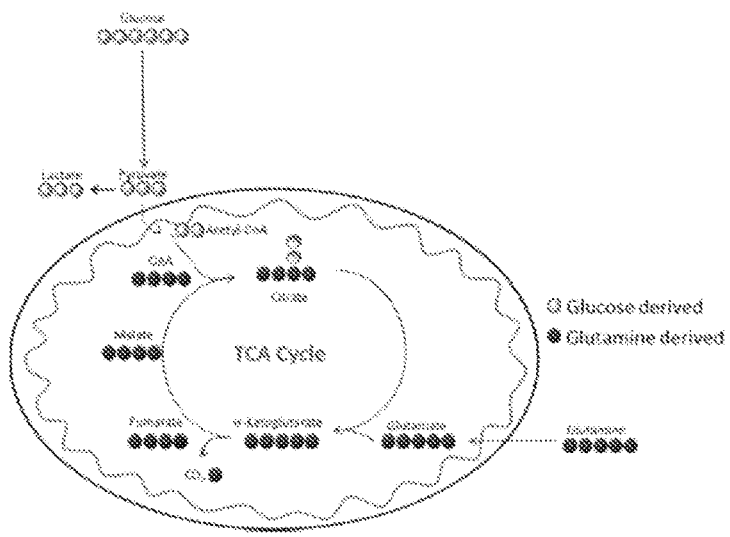

Methods for mass isotopologue distribution analyses using [U-$^{13}$C]glutamine or [U-$^{13}$C]glucose (Cambridge Isotope Laboratories) were adapted from Cheng et al., "Pyruvate Carboxylase Is Required for Glutamine-Independent Growth of Tumor Cells," *Proc. Natl. Acad. Sci.* 108:8674-79 (2011), which is hereby incorporated by reference in its entirety. Briefly, induced (16 hours in complete media without Dox) or non-induced cells (complete media with 1 µg/mL Dox) were plated into 100 mm$^2$ dishes at a density such that the cells were approximately 60% confluent when adhered, at which point the cells were washed with PBS and grown to 80% confluence in DMEM supplemented with 1% Tet-approved FBS and 8 µM 968/27 for drug treated samples, or 0.8% DMSO for control samples, with or without 1 µg/mL Dox (i.e. overnight). When 80% confluent, cells were then washed with PBS and $^{13}$C-labeling media containing the appropriate drug, DMSO, and Dox concentrations. Media was prepared from glucose- and glutamine-free DMEM powder (Sigma) and supplemented with 1% Tet-approved FBS, 2 mM L[U-$^{13}$C]glutamine and 15 mM unlabeled glucose or 15 mM D[U-$^{13}$C]glucose and 2 mM unlabeled glutamine (FIGS. 2F-G), together with 1 µg/mL Dox for non-induced samples. For samples containing [U-$^{13}$C]glutamine, cells were incubated for 1 hour before extracting metabolites, whereas samples containing [U-$^{13}$C] glucose were incubated for 8 hours. Metabolites were extracted by first washing cells twice with ice cold normal saline (0.9% w/v NaCl), followed by addition of 0.5 mL of a 1:1 methanol:water mixture (−20° C.). An internal standard (50 nmol of 2-oxobutyrate) was added and samples were subjected to 3 freeze-thaw cycles, after which macromolecules were separated by centrifugation. The supernatant was evaporated completely and remaining metabolites sily-lated in 100 μL of a trimethylsilyl donor (Tri-Sil, Thermo) for 30 minutes at 42° C. Metabolites were subjected to GC-MS analysis using an Agilent 6970 gas chromatograph networked to an Agilent 5973 mass selective detector. Metabolites were identified and isotope enrichment calculated as described by Cheng et al., "Pyruvate Carboxylase Is Required for Glutamine-Independent Growth of Tumor Cells," *Proc. Natl. Acad. Sci.* 108:8674-79 (2011), which is hereby incorporated by reference in its entirety.

Example 3

Recombinant Glutaminase Preparation and Labeling with Spectroscopic Probes

A plasmid encoding the mouse kidney-type glutaminase isoform 2 (GAC, GenBank Accession No. NP_001106854.1, which is hereby incorporated by reference in its entirety) (residues 72-603) was cloned into a pET23a vector containing an N-terminal histidine (His)-tag and thrombin cleavage site. The expressed protein was purified using $Co^{2+}$ affinity beads (Clontech), followed by His-tag cleavage with human thrombin (Haemetologic Technologies) overnight at 4° C., and subsequently purified by anion exchange (GE healthcare) and gel filtration chromatography. Purified GAC was stored in a high salt-containing buffer (20 mM Tris-HCl pH 8.5, 500 mM NaCl, 1 mM NaN3) at −80° C., following snap freezing in liquid $N_2$ for long term use. Labeling recombinant GAC with small molecule probes was performed by exchanging 1.5 mg of enzyme into 50 mM HEPES, pH 7.2, and 100 mM NaCl (labeling buffer), using a PD10 desalting column (GE healthcare). The enzyme was then incubated with 50 μM (5-fold excess of enzyme) of either AlexaFluor 488 succinimidyl ester or QSY9 succinimidyl ester (Molecular Probes) for 1 hour at 4° C. After 1 hour, the labeling reaction was quenched with 150 mM Tris-HCl, pH 8.5, and unreacted probe was separated from labeled-enzyme using a PD10 desalting column, eluting labeled-GAC back into the high salt-containing buffer. The stoichiometry of labeling was determined using the probe manufacturer's reported molar absorptivity values and instructions. Briefly, the concentration of GAC was determined by first correcting absorbance at 280 nm (Abs280) for each probe, using the reported correction values (0.11 for AlexaFluor 488 and 0.23 for QSY-9) and their absorbance values at their absorbance maxima (495 nm and 562 nm, respectively). The corrected Abs280 was used along with the experimentally determined molar absorptivity of GAC ($\varepsilon 280=38,850$ M−1 cm−1). AlexaFluor 488 and QSY-9 probes were quantified using their respective absorbance maxima and the manufacturer's reported molar absorptivity values ($\varepsilon 495=71,000$ M−1 cm−1 and $\varepsilon 562=85,000$ M−1 cm−1). The labeling stoichiometries for 488-labeled and QSY-9 labeled GAC were found to be 0.49±0.09 and 1.00±0.05 respectively, where stoichiometry is defined as moles probe/moles protein.

Example 4

FRET Assays

Fluorescence experiments were performed using a Varian Cary Eclipse Fluorometer in the counting mode. Excitation and emission wavelengths were 490 and 520 nm, respectively. Experiments were all performed using 1-mL samples with continuous stirring at 20° C. in 50 mM Tris-Acetate, pH 8.5, 0.1 mM ethylenediamine tetraacetic acid (EDTA). For wild-type (WT) GAC titrations in the absence of inorganic phosphate, 25 nM 488-GAC was equilibrated with 25 μL of QSY9-GAC (at varying concentrations) and allowed to equilibrate for 10 minutes, at which point 75 μL of the appropriate concentration of unlabeled WT GAC was added to provide a 10-fold excess over labeled-GAC. To test whether the purified GAC mutants can form oligomers with WT GAC, 200 nM QSY9-GAC (D391K) or 200 nM QSY9-GAC (D391K, K316E, R459E) was added to an equilibrated sample of 20 nM 488-WT GAC. When assaying the effects of BPTES and 968 on oligomer formation, BPTES or 968 was added following equilibration of a sample of 25 nM QSY9-WT GAC and 25 nM 488-WT GAC. Both BPTES and 968 were prepared in DMSO, and appropriate dilutions were made so that less than 2% (v/v) DMSO was added to an experimental sample.

Example 5

Real-Time 968 Binding and Enzyme Activity Assays

Real-time fluorescence monitoring of 968 binding and GAC activity through production of NADH was performed on a Varian Cary Eclipse Fluorometer, whereas small molecule inhibition and binding titrations were performed in a 96-well format in a Tecan Saphire absorbance and fluorescence plate reader. Samples for monitoring real-time binding of 968 to 488-GAC were prepared by adding 10 μL of varying concentrations of 968 prepared in DMSO to an equilibrated 1 mL sample of 10 nM 488-GAC, while observing 488 fluorescence (490 nm excitation/520 nm emission). Similarly, this method was replicated for monitoring real-time binding of 968 to mutant forms of GAC, namely 488-labeled GAC (GD391K) and 488-GAC (D391K, K316E, R459E). Real-time activity assays monitoring 968 binding and NADH production were prepared in 1 mL samples, where 10 units of glutamate dehydrogenase (Sigma) and 2 mM NAD+ (Sigma) were prepared in 50 mM Tris-Acetate, pH 8.5, 0.1 mM EDTA and equilibrated at 20° C. WT GAC (10 nM) was added and allowed to equilibrate 2 minutes before monitoring the fluorescence emission of 488-GAC (490 nm excitation, 520 nm emission) and NADH (340 nm excitation, 490 nm emission). Appropriate dilutions of 968 or BPTES prepared in DMSO were introduced after 30 seconds and allowed to equilibrate for 2 minutes before a 180 μL solution of $K_2HPO_4$ and glutamine was added to make a final concentration of 50 mM $K_2HPO_4$ and 20 mM glutamine, to initiate GAC activation. The activity of GAC was measured in a coupled assay, by monitoring the NADH produced by glutamate dehydrogenase, which converts the product of the glutaminase-catalyzed reaction, glutamate, to α-ketoglutarate and ammonia by reducing NAD+ to NADH. Because solutions containing glutamine undergo non-enzymatic degradation to glutamate, samples were further analyzed by subtracting the NADH produced by glutaminase in the presence of 968, BPTES, or the equivalent volume of DMSO as a control, from the NADH produced in the absence of glutaminase under identical experimental conditions. NADH was quantified using a standard curve of freshly prepared NADH (Sigma) in 50 mM Tris-Acetate, pH 8.5, and 0.1 mM EDTA.

Procedures for the real-time binding and inhibition assays were adapted for 96-well microtiter format with minor alterations. Briefly, 2 μL of inhibitor or DMSO were distributed across the 96-well plate, followed by addition of 200 μL of 10 nM 488-GAC, unlabeled WTGAC, or in the absence of added GAC as a negative control, in 50 mM Tris-Acetate, pH 8.5, and 0.1 mM EDTA, followed by immediate monitoring of 488 fluorescence (490 nm/520 nm excitation/emission, 5 nm/20 nm excitation/emission slits). The 488-fluorescence was measured every 2 minutes with 90 seconds of orbital shaking, followed by 30 seconds resting between each cycle for a total of four cycles (i.e. 6 minutes). A mixture of GDH and NAD+ (20 μL) was then added to give 10 units of GDH and 2 mM NAD+. To activate GAC, 30 μL of a mixture of glutamine and $K_2HPO_4$ were added to give a total concentration of 50 mM $K_2HPO_4$ and 20 mM glutamine in each well. NADH fluorescence was measured (340 nm/460 nm excitation/emission, 10 nm/10 nm excitation/emission slits) every minute with 30 seconds orbital shaking, and a 30 second rest between each reading, for 10 cycles (i.e. 9 minutes). Three wells were prepared for each experimental condition (i.e. each concentration of compound) alongside one well where 2 μL of DMSO were added in place of inhibitor, and one well that contained the small molecule inhibitor but no GAC. To analyze 488-quenching by the added compound, 488-fluorescence (F) was normalized to the DMSO control (F0). Quenching was quantified as follows: 1-F/F0. For compounds that emitted fluorescence within the observed range, fluorescence measured in the well that contained the compound but lacked GAC was used to subtract added fluorescence due to the compound. Similarly, samples were analyzed for NADH fluorescence by subtracting the fluorescence measured for the experimental condition from the NADH fluorescence in the well that contained the added compound but no GAC. Percent inhibition at each drug concentration was calculated using the adjacent DMSO control.

Example 6

End-Point Glutaminase Activity Assays

Activity assays used to compare FRET values and evaluate the activity of GAC mutants followed a two-step protocol adapted from Robinson et al., "Novel Mechanism of Inhibition of Rat Kidney-Type Glutaminsae by Bis-2-(5-Phenylacetamido-1,2,4-Thiadiazol-2-yl) Ethyl Sulfide (BPTES)," *Biochem. J.* 406(3):407-14 (2007), which is hereby incorporated by reference in its entirety). Briefly, 20 μL of 20 mM glutamine, 50 mM Tris-acetate, pH 8.5, and 0.1 mM EDTA, in either the presence or absence of a $K_2HPO_4$, were added to a UV-transparent Costar 96-well plate (Corning). To initiate the reaction, 5 μL of a solution of the appropriate concentration of GAC, prepared in 20 mM Tris-HCl, pH 8.5, 100 mM NaCl, and 1 mM $NaN_3$, were added to the glutamine solution and incubated at 23° C. for 2 minutes before the reaction was quenched using 2.5 μL of 3 M HCl. For reactions that contained more than 250 nM GAC, the first reaction was quenched at 30 seconds instead of 2 minutes. The second step was initiated by the addition of 200 μL of 12 units/μL GDH, 2 mM NAD+, 100 mM hydrazine (Sigma), and 100 mM Tris-HCl, pH 9.2, on top of the first quenched reaction and incubated for 45 minutes at 23° C. before reading NADH absorbance. Glutamate produced by the first reaction was determined from the amount of NADH generated in the second reaction by using the extinction coefficient for NADH (6,220 M−1 cm−1).

Example 7

Multi-Angle Light Scattering (MALS)

Purified GAC and GAC mutants were subjected to multi-angle light scattering (MALS) as previously described by Moller et al., "Small Angle X-Ray Scattering Studies of Mitochondrial Glutaminase C Reveal Extended Flexible Regions, and Link Oligomeric State with Enzyme Activity," *PLoS One* 8(9):e74783 (2013), which is hereby incorporated by reference in its entirety. Briefly, 50 μL samples of 5 mg/mL GAC were injected onto a WTC-030S5 size-exclusion column (Wyatt technology), coupled to a static 18-angle light scattering detector (DAWN HELEOS-II) and a refractive index detector (OptiLab TrEX, Wyatt Technology), at 23° C. The size-exclusion column was equilibrated with 20 mM Tris-HCl, pH 8.5, and 200 mM NaCl with or without 50 mM $K_2HPO_4$. The flow rate was kept at 1 mL/minutes. RMS radius and mass distribution (polydispersity) were analyzed using the ASTRA software, with monomeric BSA (Sigma) serving to normalize the light scattering signal.

Example 8

Preparation of 968 Analogs

Compounds 27 (see FIG. 5D(i)) and 742 (see FIG. 5D(g)) were obtained from Chembridge (San Diego), and compound 031 was from Specs (Netherlands). Starting materials for chemical synthesis were used without further purification.

Example 9

3-Bromo-4-(Dimethylamino)Benzaldehyde (4)

4-(Dimethylamino)benzaldehyde (6.7 mmol) was suspended in 1,4 dioxane (13 mL), Nbromosuccinimide (7.0 mmol) was added at once and stirred at room temperature for 3 hours. Water (50 mL) and ethyl acetate (50 mL) were added and the organic layer washed with two more portions of water (50 mL) then removed and dried with magnesium sulfate. The solvent was removed by rotary evaporation and the crude product purified by silica gel chromatography using 2:1 $CH_2Cl_2$:hexane as the eluent to give 0.84 g of a clear oil (55% yield). 1H NMR (400 MHz, CDCl3): δ=9.80 (1H, s), 8.03 (1H, d, J=1.84 Hz), 7.73 (1H, dd, J=8.24 Hz, 1.84 Hz), 7.06 (1H, d, J=8.24 Hz), 2.94 (6H, s).

Example 10

General Procedure for Synthesis of 968, SU-1, and SU-14 (5)

The appropriate arylamine, 3-bromo-4-(dimethylamino) benzaldehyde and dimedone (2 mmol each) were heated to reflux in 10 mL ethanol for 1 hour, upon which time a precipitate formed. The precipitate was filtered, washed with ethanol and dried to give the product.

968: $^1$H NMR (400 MHz, d6-DMSO): δ=9.71 (1H, s), 7.91 (1H, d, J=8.7 Hz), 7.76 (2H, m), 7.40 (1H, m), 7.35 (1H, m), 7.28 (2H, m), 7.10 (1H, dd, J=8.24 Hz, 1.8 Hz), 6.90 (1H, d, J=8.24 Hz), 5.70 (1H, s), 2.52 (6H, s), 2.47 (1H, d, J=15.9 Hz) 2.37 (1H, d, J=15.9 Hz), 2.18 (1H, d, J=16.0 Hz), 2.02 (1H, d, J=16.0 Hz), 0.99 (3H, s), 0.85 (3H, s).

SU-1: $^1$H NMR (400 MHz, d6-DMSO): δ=9.28 (1H, s), 8.40 (1H, d, J=8.9 Hz), 7.78 (1H, d, J=8.9 Hz), 7.55 (1H, m), 7.45 (2H, m), 7.36 (1H, m), 7.25 (1H, d, J=8.1 Hz), 7.11 (1H, m), 6.94 (1H, d, J=8.8 Hz), 5.11 (1H, s), 2.73 (1H, d, J=15.1 Hz), 2.64 (1H, d, J=15.1 Hz), 2.55 (6H, s), 2.22 (1H, d, J=16.0 Hz), 2.04 (1H, d, J=16.0 Hz), 1.02 (3H, s), 0.97 (3H, s).

SU-14: $^1$H NMR (d6-DMSO): δ=9.77 (1H, s), 8.56 (1H, s), 8.43 (1H, s), 8.07 (1H, d, J=7.8 Hz), 7.94 (2H, d, J=9.16 Hz), 7.49 (1H, m), 7.40 (2H, m), 7.31 (1H, m), 7.26 (1H, m), 6.90 (1H, d, J=8.3 Hz), 5.88 (1H, s), 2.55 (1H, d, J=16.0 Hz), 2.50 (6H, s) 2.42 (1H, d, J=16.0 Hz), 2.22 (1H, d, J=16.0 Hz), 2.05 (1H, d, J=16.0 Hz), 1.02 (3H, s), 0.88 (3H, s).

Example 11

General Procedure for Synthesis of SU-2, SU-7, SU-8

The appropriate arylamine (3.7 mmol) and 3-bromo-4-(dimethylamino) benzaldehyde (3.7 mmol) were dissolved in benzene (5 mL) supplemented with molecular sieves (0.7 g) and stirred at RT for 18 hours. The mixture was filtered and the solid material washed with dichloromethane. The combined filtrate was dried with magnesium sulfate, filtered and the solvent removed by rotary evaporation. The crude imine was dissolved in 1-butanol (6 mL), combined with dimedone (2 mmol) and heated to reflux for 2 hours. The reaction mixture was cooled and solvent removed by rotary evaporation. The crude product was purified by silica gel chromatography using 1:1 hexanes:ethyl acetate as the eluent.

SU-2: $^1$H NMR (400 MHz, CDCl3): δ=7.35 (1H, d, J=1.7 Hz), 7.1-7.25 (3H, m), 6.96 (1H, dd J=1.7 Hz, 11 Hz), 6.92 (1H, d, J=11 Hz), 6.75 (1H, d, J=8.9 Hz), 6.61 (1H, br s), 5.19 (1H, s), 2.69 (6H, s), 2.38 (1H, d, J=8.0 Hz), 2.34 (2H, m), 2.24 (1H, d, J=8 Hz), 1.09 (3H, s), 1.12 (3H, s).

SU-7: $^1$H NMR (400 MHz, CDCl3): δ=7.30 (1H, d, J=1.8 Hz), 7.18 (1H, dd, J=8.2 Hz, 1.8 Hz), 7.06 (2H, m), 6.93 (1H, d, J=8.3 Hz), 6.69 (1H, d, J=9.1 Hz), 6.20 (1H, br s), 5.11 (1H, s), 2.74 (2H, m), 2.72 (6H, s), 2.40 (1H, d, J=11.4 Hz), 2.22 (1H, d, J=9.1 Hz), 1.09 (3H, s), 1.03 (3H, s).

SU-8: $^1$H NMR (400 MHz, d6-DMSO): δ=7.33 (1H, d, J=1.7 Hz), 7.1-7.2 (3H, m), 6.92 (1H, d, J=11 Hz), 6.70 (1H, d, J=11 Hz), 6.34 (1H, br s), 5.19 (1H, s), 2.70 (6H, s), 2.38 (2H, m), 2.22 (2H, m) 1.23 (9H, s), 1.09 (3H, s), 1.02 (3H, s).

Example 12

The GAC Inhibitor 968 Blocks Glutaminolysis in Transformed Cells

Previous work identified a potential connection between glutamine metabolism and Rho GTPase-dependent oncogenic transformation, through the discovery of the small molecule inhibitor 968 (Wang et al., "Targeting Mitochondrial Glutaminase Activity Inhibits Oncogenic Transformation," *Cancer Cell* 18(3):207-19 (2010), which is hereby incorporated by reference in its entirety). It was shown that 968 specifically inhibited the growth of transformed cells and various cancer cells by blocking GAC activation, although the detailed mechanism was unclear. Here, it has been set out to better understand how 968 functions by first examining its effects on glutamine metabolism in a well-defined model system for oncogenic transformation, in which the stable expression of the Dbl oncogene in mouse embryonic fibroblasts (MEFs) is controlled by the removal of doxycycline (Dox).

Figure 1B:
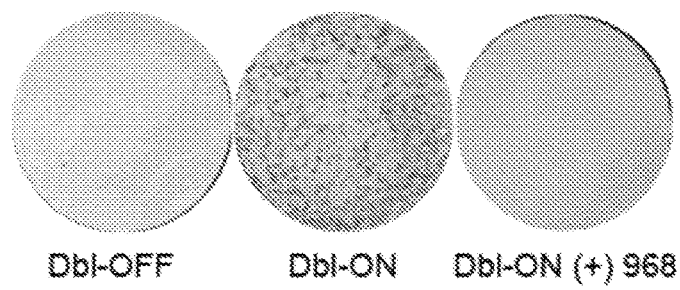
Figure 1C:
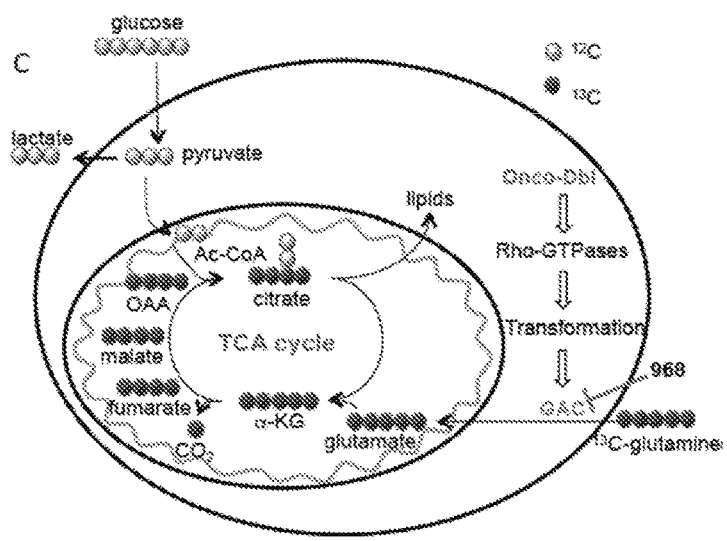
Figure 1D:
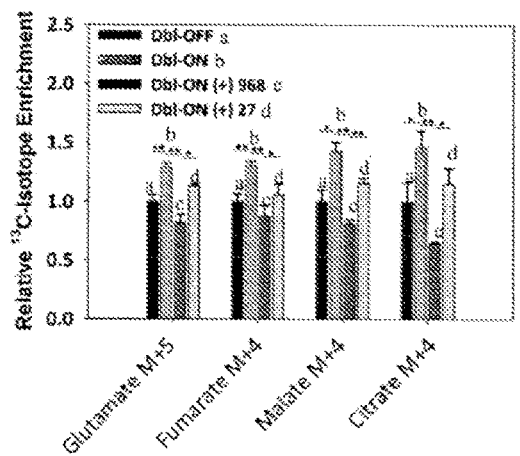

As shown in FIG. 1A, induction of oncogenic Dbl in MEFs results in marked changes in cell morphology, as a result of cytoskeletal rearrangements caused by the activation of Rho GTPases (Lin et al., "Specific Contributions of the Small GTPases Rho, Rac, and Cdc42 to Dbl Transformation," *J. Biol. Chem.* 274(33):23633-41 (1999); Rossman et al., "GEF Means Go: Turning on Rho GTPases with Guanine-Nucleotide Exchange Factors," *Nat. Rev. Mol. Cell. Biol.* 6(2):167-80 (2005); Etienne-Manneville and Hall, "Rho GTPases in Cell Biology," *Nature* 420(6916): 629-35 (2002); Olivo et al., "Distinct Involvement of Cdc-42 and RhoA GTPases in Actin Organization and Cell Shape in Untransformed and Dbl Oncogene Transformed NIH3T3 Cells," *Oncogene* 19(11):1428-36 (2000), which are hereby incorporated by reference in their entirety). These morphological changes accompany the ability of oncogenic Dbl-expressing cells to overcome contact inhibition to form foci. Consistent with previous results (Wang et al., "Targeting Mitochondrial Glutaminase Activity Inhibits Oncogenic Transformation," *Cancer Cell* 18(3):207-19 (2010), which is hereby incorporated by reference in its entirety), treatment of MEFs expressing oncogenic Dbl with 968 blocked focus formation (FIG. 1B). It was then examined whether these effects were accompanied by an inhibition of glutaminolysis. As shown in FIGS. 1C and 1D, the induction of oncogenic Dbl expression in MEFs increased glutaminolysis and glutamine dependent anaplerosis, as monitored by $^{13}$C enrichment in TCA cycle intermediates derived from [U-$^{13}$C]-glutamine. As shown in FIGS. 2A-F, treatment of Dbl-expressing cells with 968 caused significant reductions in the glutamine-derived $^{13}$C isotopic enrichment within TCA cycle intermediates, but did not result in the depletion of relative pool sizes of each metabolite, with the exception of a modest reduction in intracellular glutamate (compare red (b) and yellow (d) versus black (a), green (b), and blue (e)). A modest inhibition of glutaminolysis by 968 was also observed in MEFs not expressing Dbl (see FIG. 1B and the M+5 histograms for Dbl-OFF, ±968, in FIG. 2C, and the M+4 histograms in FIGS. 2D-F). However, these effects were not accompanied by reductions in cell growth, suggesting that glutamine metabolism is critical for supporting the transformed phenotypes accompanying oncogenic Dbl expression, but not for the proliferative capability of normal MEFs. Treatment with the less potent 968-analogue, compound 27, caused a weaker inhibition of the $^{13}$C enrichment of metabolites (see FIG. 1D), consistent with its reduced potency to inhibit enzymatic activity (see below).

As shown in FIG. 2G, oncogenic Dbl induction did not cause marked increases in glucose-fueled anaplerosis, as measured by $^{13}$C enrichment in citrate, when using [U-$^{13}$C]-glucose as a tracer (see the M+2 histograms in FIG. 2G), demonstrating that a highly specific stimulation of glutamine metabolism accompanies Rho GTPase-dependent transformation. However, 968 was observed to inhibit glucose labeling of citrate isotopologues (see the M+2 histogram in FIG. 2H). This presumably was due to the inhibition of glutamate flux by 968. Overall, these results show how 968 attenuates cellular glutamine metabolism and restores a normal growth phenotype in cells expressing oncogenic Dbl, thus highlighting the role of glutamine as a critical source for anaplerosis during cellular transformation.

Example 13

Examining the Effects of 968 on the Dimer-to-Tetramer Transition of GAC

The transition of GAC from a dimer to a tetramer has been suggested to be essential for enzyme activity (Robinson et al., "Novel Mechanism of Inhibition of Rat Kidney-Type Glutaminsae by Bis-2-(5-Phenylacetamido-1,2,4-Thiadiazol-2-yl)Ethyl Sulfide (BPTES)," *Biochem. J.* 406(3):407-14 (2007); Godfrey et al., "Correlation Between Activation and Dimer Formation of Rat Renal Phosphate-Dependent Glutaminase," *J. Biol. Chem.* 252(6):1927-31 (1977); Kenny et al., "Bacterial Expression, Purification, and Characterization of Rat Kidney-Type Mitochondrial Glutaminase," *Protein Expr. Purif.* 31(1):140-48 (2003), which are hereby incorporated by reference in their entirety). A well-established allosteric inhibitor of GAC, BPTES, has been shown to stabilize an inactive tetrameric state of the enzyme (Robinson et al., "Novel Mechanism of Inhibition of Rat Kidney-Type Glutaminsae by Bis-2-(5-Phenylacetamido-1,2,4-Thiadiazol-2-yl)Ethyl Sulfide (BPTES)," *Biochem. J.* 406(3):407-14 (2007), which is hereby incorporated by reference in its entirety). Thus, it was examined whether 968 acted in a similar manner, by developing a real-time read-out for the GAC dimer-to-tetramer transition. FIG. 3A depicts the proposed FRET assay, where oligomer formation is monitored between two populations of purified recombinant GAC, labeled with either the highly fluorescent AlexaFluor 488 (donor) probe, or with the non-fluorescent QSY9 (acceptor) chromophore. A major advantage of using FRET as a direct read-out for GAC tetramer formation is the ability to monitor oligomer formation at the low concentrations of GAC commonly used for assaying its enzymatic activity.

The addition of QSY9-GAC to 488-GAC yielded a dose-dependent quenching of the donor 488 emission due to FRET, that was reversible upon the addition of unlabeled GAC, demonstrating that GAC tetramer formation is a dynamic process (see FIG. 3B). The dose dependent binding isotherm obtained from the QSY9-GAC titration profile directly correlated with the basal activation of GAC that occurs at increasing protein concentrations (i.e. due to tetramer formation through mass-action), yielding an apparent $K_D$ of 164 nM (±20 nM) for tetramer formation (see FIG. 3C), supporting the contention that the GAC tetramer is the minimal unit for enzymatic activity.

The effects of 968 were then compared, versus BPTES, on the GAC dimer-to-tetramer transition. Consistent with previous findings that BPTES stabilizes GAC as an inactive tetramer (DeLaBarre et al., "Full-Length Human Glutaminase in Complex with an Allosteric Inhibitor," *Biochemistry* 50(50):10764-70 (2011), which is hereby incorporated by reference in its entirety), it was found that it caused an immediate quenching of 488-GAC fluorescence emission when added to a mixture of 488-GAC and QSY9-GAC (see FIG. 3D), i.e. due to the ability of BPTES to promote the formation of 488-GAC:QSY9-GAC (donor:acceptor) tetramers. These stable GAC:BPTES tetrameric complexes were less susceptible to reversal by the addition of unlabeled GAC (in FIG. 3D, compare the "a" trace for the addition of unlabeled GAC in the presence of the vehicle control DMSO to the "e" trace, which represents the addition of unlabeled GAC in the presence of 5 µM BPTES). Interestingly, 968 elicited a markedly different response, causing a significant change in the fluorescence emission of 488-GAC, followed by a partial fluorescence recovery upon the addition of excess unlabeled GAC (see FIG. 3E). The recovery of 488 fluorescence when adding excess unlabeled GAC was due to the elimination of FRET between 488-GAC and QSY9-GAC, following the formation of mixed tetramers between 488-GAC or QSY9-GAC and unlabeled GAC. Thus, 968 does not appear to interfere with GAC tetramer formation. However, the inability to achieve a full recovery of the fluorescence emission suggested that 968 binding was directly affecting 488-GAC donor fluorescence emission. Indeed, it was found that 968 caused a dose-dependent quenching of 488-GAC emission (in the absence of the FRET acceptor QSY9-GAC) that matched the 968-mediated inhibition of GAC activity (see FIG. 3F and FIG. 4). Taken together, these findings show that 968 does not mimic the actions of BPTES by trapping GAC in an inactive tetrameric state, but instead regulates GAC activity through a distinct allosteric mechanism.

Example 14

Real-Time Monitoring of 968 Binding to GAC and Its Inhibition of Enzyme Activity A real-time enzyme activity assay was developed so as to simultaneously monitor both the binding of 968 to GAC and its effects on enzyme activity. The enzymatic activity of 488-GAC is assayed by monitoring NADH production (i.e. fluorescence emission at 460 nm) that accompanies the conversion of glutamate (the product of the GAC-catalyzed reaction) to α-ketoglutarate, catalyzed by glutamate dehydrogenase. FIG. 5A depicts the coupling of these two fluorescence assays, and FIG. 5B shows the results of an experiment simultaneously monitoring the direct binding of 968 to GAC ("a", solid line) and its inhibition of enzyme activity ("b", solid line; the dashed line represents the control enzyme activity treated with the solvent vehicle DMSO). Unlike 968, BPTES does not directly affect 488-GAC fluorescence, under conditions where it strongly inhibits GAC activity (in FIG. 5B, see the "a" and "b" dotted traces, respectively).

These assays were then adapted to a 96-well plate format, and it was shown that 968 exhibited an overlapping dose-dependent inhibition of both 488-GAC and unlabeled GAC activity (FIG. 5C, black closed and open circles respectively), as well as an overlapping dose-response for its direct binding to 488-GAC (FIG. 5C, grey closed circles). The robustness of these high throughput binding and enzymatic assays was tested by examining a group of newly synthesized 968-derivatives (compounds SU-1, SU-2, SU-7, SU-8, and SU-14 in FIG. 5D), together with molecules 031, 27, and 742 (see FIG. 5D) that were previously characterized and shown to be GAC inhibitors (Wang et al., "Targeting Mitochondrial Glutaminase Activity Inhibits Oncogenic Transformation," *Cancer Cell* 18(3):207-19 (2010); Katt et al., "Dibenzophenanthridines as Inhibitors of Glutaminase C and Cancer Cell Proliferation," *Mol. Cancer Ther.* 11(6):1269-78 (2012), which are hereby incorporated by reference in their entirety). A direct correlation exists between the ability of different 968 analogs to bind to GAC and to inhibit its enzymatic activity (see FIG. 5E). The results of these analyses, and particularly the finding that substituting the napthyl group of 968 with a quinoline moiety (e.g. compound 27) markedly affected both binding and inhibitory activity, suggests that hydrophobicity at this position is required for maximal efficacy.

Previous studies of the 968-mediated inhibition of recombinant GAC activity showed that 968 was much more effective when it was added prior to glutamine and inorganic phosphate (the latter being an allosteric activator that stimulates GAC tetramer formation and GAC activity), compared to when it was added after the addition of phosphate (Katt et al., "Dibenzophenanthridines as Inhibitors of Glutaminase C and Cancer Cell Proliferation," *Mol. Cancer Ther.* 11(6): 1269-78 (2012), which is hereby incorporated by reference in its entirety). Therefore, whether the ability of 968 to bind to GAC was compromised under conditions where the enzyme was pre-treated with inorganic phosphate and assumed an activated tetrameric state was examined. In fact, it was found that 968 was capable of binding to a tetrameric GAC species comprised of 488-labeled GAC and QSY9-labeled GAC dimers, as read-out by the quenching of 488 fluorescence emission (FIGS. 6A and 6B). Moreover, 968 was able to bind to GAC that had been preincubated with inorganic phosphate (FIG. 6C, closed versus open circles). However, under these conditions, 968 was much less effective at inhibiting enzyme activity (FIG. 6D, closed versus open circles). Thus, phosphate induces an activated state that is less sensitive to 968 inhibition, even though 968 is able to bind to phosphate-activated GAC. In contrast, when GAC was pre-incubated with 968 before adding phosphate, the enzyme activity was strongly inhibited and directly correlated with the binding of 968 (FIGS. 6C and 6D, open circles).

Example 15

968 Preferentially Binds to the Monomeric State of GAC

Docking analyses using the x-ray structure of the GAC tetramer, together with mutagenesis studies, suggested that 968 binds in a cove between the monomer-monomer interface (Katt et al., "Dibenzophenanthridines as Inhibitors of Glutaminase C and Cancer Cell Proliferation," *Mol. Cancer Ther.* 11(6):1269-78 (2012), which is hereby incorporated by reference in its entirety). To examine the ability of 968 to bind to different oligomeric states of GAC, the recently solved x-ray structures of GAC (DeLaBarre et al., "Full-Length Human Glutaminase in Complex with an Allosteric Inhibitor," *Biochemistry* 50(50):10764-70, which is hereby incorporated by reference in its entirety) was used to design mutants trapped as either monomers or dimers. FIG. 7A depicts the BPTES-binding sites within the GAC tetramer interface and the proposed 968-binding pocket at the C-terminal region of the monomer-monomer interface. Residue contacts that were mutated in order to create constitutive monomeric and dimeric GAC mutants are highlighted at the GAC-tetramer helical interface (bottom inset), as well as at the GAC dimer interface (top inset). When a point mutation was incorporated at the tetramer interface of mouse GAC (D391K), tetramer formation was disrupted with the resulting GAC mutant being trapped in a dimeric state, as determined by multi-angle light scattering (MALS) (FIG. 7B, "b" trace) and further confirmed with the determination of its x-ray crystal structure (PDB submission in preparation). Introducing point mutations at the dimer interface of mouse GAC (K316E, R459E), within the background of the dimeric GAC mutant, resulted in a monomeric GAC (D391K, K316E, R459E) species (FIG. 7B, "c" trace). As expected, the monomeric and dimeric GAC mutants showed neither a concentration-dependent basal enzymatic activity, nor phosphate-stimulated activity (FIGS. 7C-D). While the addition of wildtype (WT) QSY9-labeled GAC to WT 488-labeled GAC resulted in the expected FRET due to tetramer formation (FIG. 7E, "a" trace), the addition of either the QSY9-labeled GAC (D391K) dimer or the GAC (D391K, K316E, R459E) monomer to WT 488-labeled GAC failed to result in a significant quenching of the 488-donor fluorescence (FIG. 7E, "b" and "c" traces, respectively). The addition of the dimeric QSY9-GAC (D391K) to WT 488-GAC did induce a minor quenching of the 488-GAC emission, however, this was most likely due to the formation of mixed donor and acceptor labeled dimers, which result from a relatively minor exchange of the monomeric GAC units.

It was found that 968 was capable of binding to WT 488-GAC, as well as to both the dimeric GAC (D391K) and the monomeric GAC (D391K, K316E, R459E), with the monomeric GAC having the highest affinity for 968 (FIG. 7F). These results suggested that 968 should be most effective at inhibiting WT GAC at relatively low enzyme concentrations, i.e. where equilibrium conditions favor GAC initially existing as a monomer. FIG. 7G shows that when the concentration of GAC was decreased from 50 nM to 5 nM, 968 was able to inhibit GAC activity with greater potency. Furthermore, the 968-mediated inhibition of GAC activity at these low enzyme concentrations correlated well with its inhibition of oncogenic transformation (FIG. 7G).

Discussion of Examples 1-15

Previous work aimed at identifying inhibitors that specifically block Rho GTPase-dependent transformation led to the discovery of the benzophenanthridinone 968 (Wang et al., "Targeting Mitochondrial Glutaminase Activity Inhibits Oncogenic Transformation," *Cancer Cell* 18(3):207-19 (2010), which is hereby incorporated by reference in its entirety). Unexpectedly, the protein target for 968 appeared to be a specific splice variant (GAC) of a family of enzymes collectively called glutaminase, that catalyzes the hydrolysis of glutamine to glutamate with the production of ammonia. This highlighted a previously unappreciated connection between the roles of Rho GTPases in driving oncogenic transformation and the regulation of glutamine metabolism. Given the striking specificity that 968 exhibited in its ability to inhibit transformed cells and cancer cells, with little or no effect on their normal cellular counterparts, it was of interest to better understand how 968 functions.

An inducible expression system for oncogenic Dbl allowed the temporal control of the expression of this upstream activator of Rho GTPases in a well-defined manner. Using this system, a direct correlation between the ability of 968 to prevent a key outcome of Dbl-induced transformation, namely focus formation, and to specifically inhibit glutaminolysis was established. Thus, the inhibitory actions of 968 upon oncogenic transformation appear to be a direct outcome of its ability to interfere with glutamine metabolism.

It was then set out to understand how 968 inhibits the activity of a key enzyme in glutamine metabolism, GAC. Because BPTES, a well characterized allosteric inhibitor of GAC, has been shown to bind and stabilize an inactive tetrameric form of the enzyme, one possibility was that 968 had a similar effect. Previous studies used analytical ultracentrifugation, gel filtration, and electron microscopy to investigate the oligomeric transitions of GAC; however, these analyses were performed at GAC concentrations above the $K_D$ for tetramer formation reported here (Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406(3):407-14 (2007); Godfrey et al., "Correlation Between Activation and Dimer Formation of Rat Renal Phosphate-Dependent Glutaminase," *J. Biol. Chem.* 252(6):1927-31 (1977); Kenny et al., "Bacterial Expression, Purification, and Characterization of Rat Kidney-Type Mitochondrial Glutaminase," *Protein Expr. Purif.* 31(1):140-48 (2003); Ferreira et al., "Active Glutaminase C Self-Assembles into a Supratetrameric Oligomer That Can Be Disrupted By an Allosteric Inhibitor," *J. Biol. Chem.* 288(39):28009-20 (2013); Moller et al., "Small Angle X-Ray Scattering Studies of Mitochondrial Glutaminase C Reveal Extended Flexible Regions, and Link Oligomeric State With Enzyme Activity," *PLoS One* 8(9):e74783 (2013), which are hereby incorporated by reference in their entirety). Thus, a real-time FRET assay was used for monitoring GAC tetramer formation. The highly sensitive FRET assay enabled the direct monitoring of GAC tetramer formation and showed that it correlates with enzyme activation, as well as to compare the effects of 968 and BPTES on the dimer-to-tetramer transition. It was found that unlike BPTES, 968 does not stabilize an inactive tetrameric state of GAC. However, during the course of these FRET experiments, it was discovered that the binding of 968 to GAC resulted in a quenching of the reporter group fluorescence, thus providing a direct spectroscopic read-out for the ability of this inhibitor and various analogs to bind to the enzyme.

By taking advantage of a direct binding assay for 968, together with the recent development of GAC mutants that exist as monomers or dimers, it was discovered that 968 has a marked preference for binding to the monomeric form of the enzyme. While 968 is able to bind, albeit more weakly, to a GAC dimer, as well as to a GAC tetramer that has been activated by the allosteric regulator inorganic phosphate, it is unable to inhibit the activity of the activated enzyme tetramer. Therefore, 968 preferentially binds to an inactive, monomeric state of GAC and prevents it from undergoing activating conformational changes, whereas, if GAC reaches an activated state prior to 968-binding, then 968 is unable to inhibit enzyme activity.

These findings highlight the distinction between the two classes of allosteric GAC inhibitors for which BPTES and 968 are the prototypes. BPTES is able to bind and inhibit activated GAC, whereas 968 binds preferentially to and stabilizes an inactive state of the enzyme. In addition, these results shed light on the reason for previous discrepancies when comparing the 968 dose-dependencies for the inhibition of recombinant GAC activity versus oncogenic transformation (Katt et al., "Dibenzophenanthridines as Inhibitors of Glutaminase C and Cancer Cell Proliferation," *Mol. Cancer Ther.* 11(6):1269-78 (2012), which is hereby incorporated by reference in its entirety). Specifically, in those earlier experiments, the concentrations of recombinant GAC routinely being assayed represented a mixture of dimers and tetramers. Consequently, the $IC_{50}$ values for 968 reflected its weaker binding to these oligomeric GAC species. Indeed, when the binding of 968 to GAC, together with its ability to inhibit enzyme activity, is assayed at GAC concentrations where it initially exists predominantly as a monomer, the dose response profiles for these binding assays match the dose-dependent inhibition of transformation in cell culture.

In conclusion, it was shown that 968 functions as a highly specific inhibitor of oncogenic transformation by blocking a key step in glutamine metabolism necessary for sustaining the transformed state. It is demonstrated that 968 is capable of directly binding to GAC, a key enzyme responsible for elevated glutamine metabolism in transformed cells and cancer cells, and that 968 preferentially binds to a monomeric, inactive state of the enzyme. While an x-ray crystal structure of 968 bound to GAC has not yet been achieved, these findings shed new light on why this has been so challenging, given that crystallization trials have been routinely performed at GAC concentrations where it exists as a tetramer, i.e. the least favorable species for binding 968 (Brown et al., "Functional and Structural Characterization of Four Glutaminases From *Escherichia coli* and *Bacillus subtilis*," *Biochemistry* 47(21):5724-35 (2008); DeLaBarre et al., "Full-Length Human Glutaminase in Complex with an Allosteric Inhibitor," *Biochemistry* 50(50):10764-70 (2011); Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci.* 109(20): 7705-10 (2012); Cassago et al., "Mitochondrial Localization and Structure-Based Phosphate Activation Mechanism of Glutaminase C with Implications for Cancer Metabolism," *Proc. Natl. Acad. Sci. USA* 109(4):1092-97, which are hereby incorporated by reference in their entirety). The ability to generate monomeric GAC mutants now provides new opportunities for achieving such a structure. Moreover, the availability of a direct binding read-out adapted for plate-reader assays offers exciting possibilities for the identification of 968-like allosteric inhibitors that could yield new therapeutic strategies against cancer.

Example 16

Synthesis of Additional Compounds

Additional compounds having a compound 968-like scaffold were synthesized as shown below.

General Synthetic Scheme for Inhibitor Analogs of the 968 Scaffold

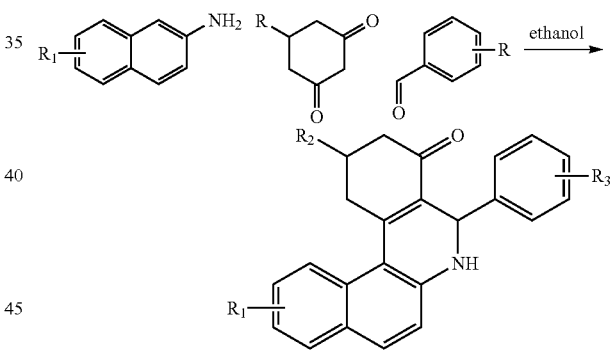

Figure 8A:
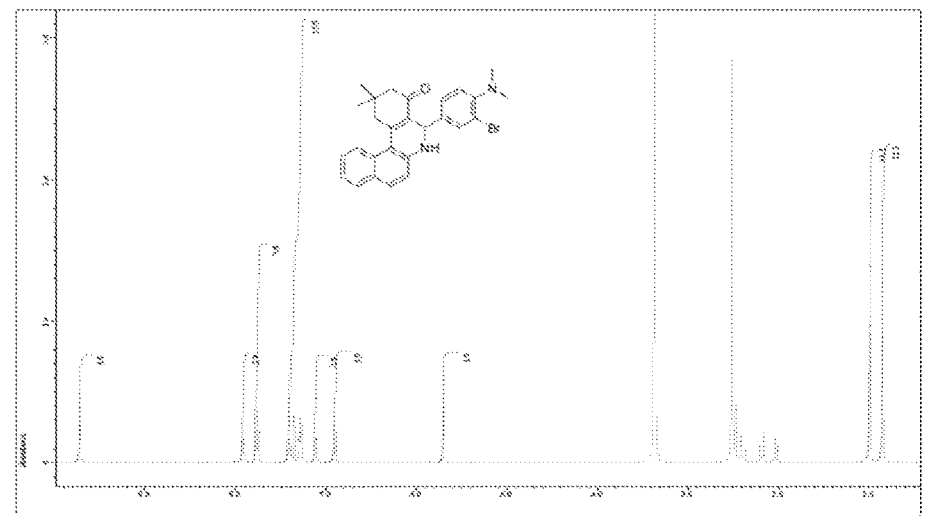
FIGS. 8A-C are representative NMRs of synthesized compounds with a 968-like scaffold (FIGS. 8A-B) or an SU-11-like scaffold (FIG. 8C).
Figure 8B:
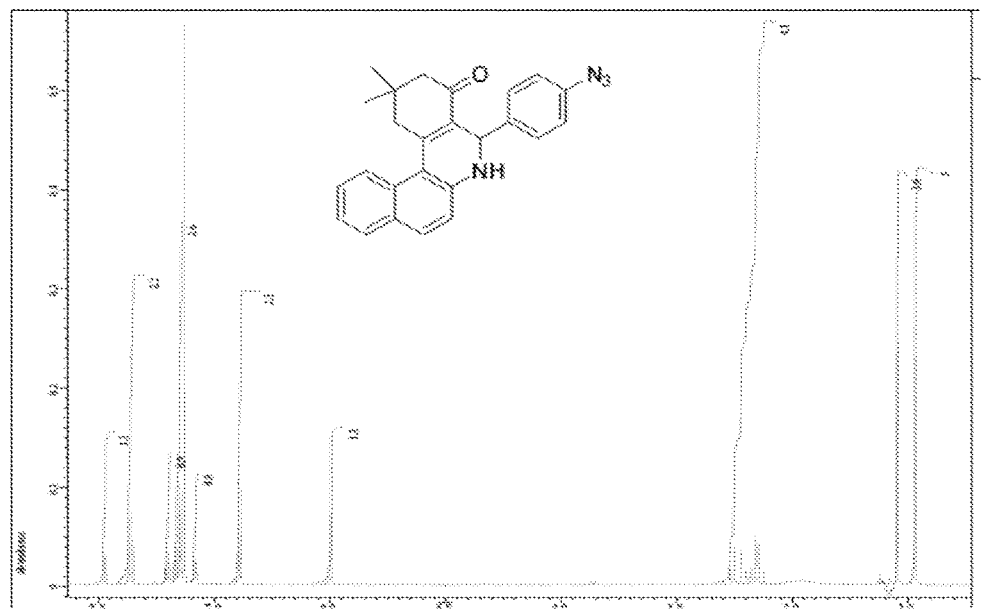

The appropriate aryl amine, 1,3 cyclohexanedione and aryl aldehyde were mixed in equal molar ratios and heated to reflux in ethanol. The resulting product generally precipitates from solution and is recovered by filtration. Representative NMRs are shown in FIGS. 8A-B.

SU-11 and compounds having a compound SU-11-like scaffold were synthesized as shown below.

General Synthetic Scheme for Inhibitor Analogs of the SU-11 Scaffold

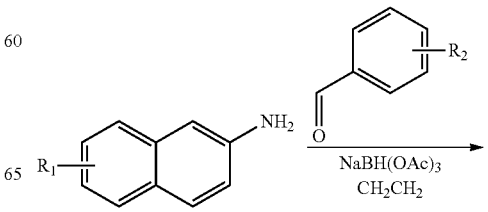

-continued

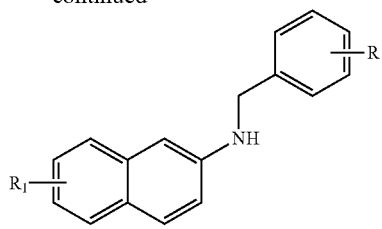

Figure 8C:
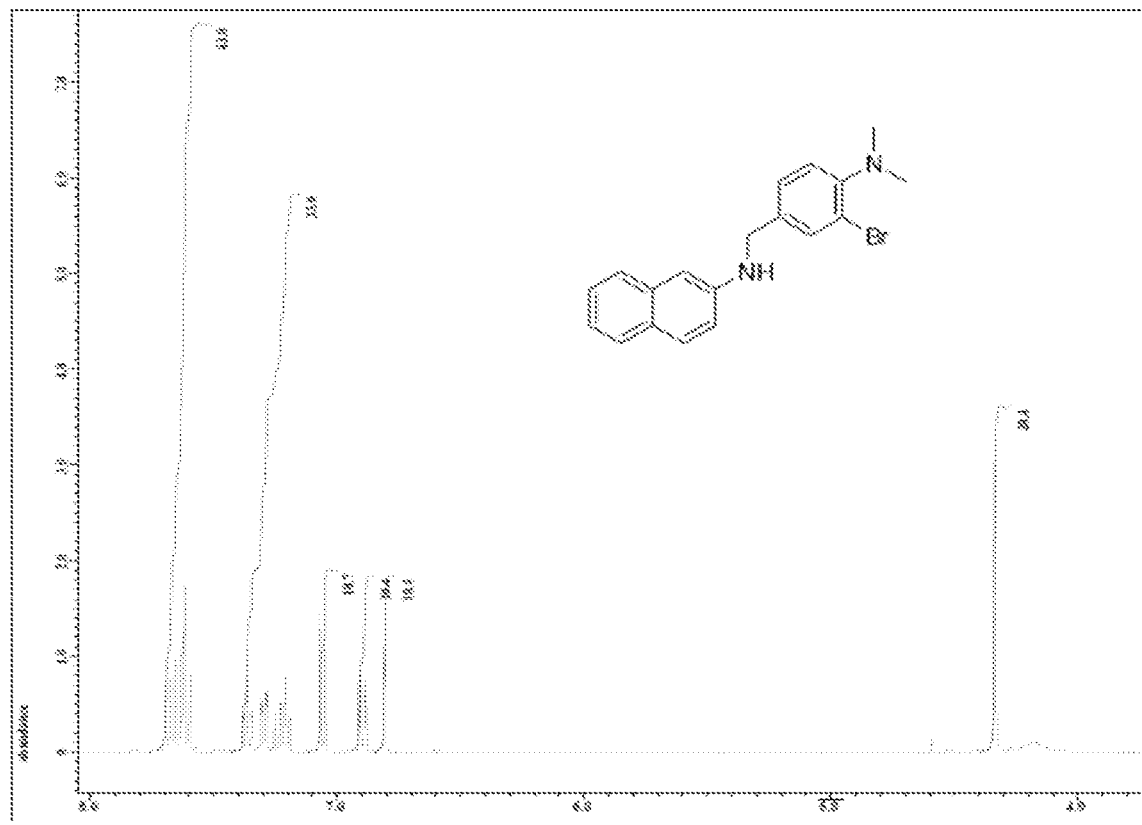

The appropriate aryl amine and aryl aldehyde were mixed in equal molar amounts in dichloromethane, and 1.3 molar equivalents of sodium triacetoxyborohydride was added and the mixture stirred at room temperature overnight. The product was purified by silica gel chromatography. Representative NMRs are shown in FIG. 8C.

Example 17

Real-Time Binding and Enzyme Activity Assays

Compounds SU-3, SU-6, and SU-9

Small molecule inhibition and binding titrations with compounds SU-3, SU-6, and SU-9 (see FIG. 9 for structures) were performed by the following procedure. The GAC inhibitors were solvated in DMSO. Assay vessels were charged with 1 μL of inhibitor in order to effect the reported final concentration. To each vessel, 95 μL of an aqueous solution containing 48 mM Tris-acetate (pH 8.6), 21 mM glutamine, and 50 nM recombinant GAC was added. Fifteen μL of either water or 1 M potassium phosphate, pH 8.2, were added to the mixture to begin the reaction. The assay reagents were incubated for 10 minutes at room temperature, at which point 10 μL of ice-cold 2.4 M hydrochloric acid was added to quench the enzymatic reaction. A second reaction vessel contained 218 μL of an aqueous solution containing 114 mM Tris-HCl (pH 9.4), 0.35 mM ADP, 1.7 mM b-NAD$^+$, 238 mM hydrazine, and 1.3 units of glutamate dehydrogenase. A third reaction vessel contained an identical solution except that it lacked β-NAD$^+$. Forty μL of the initial reaction mixture were added to each of the second and third vessels, which were then incubated at room temperature for one hour. The absorbance of both the second and third reactions was recorded at 340 nM. The third reaction was treated as a baseline, and its absorbance was subtracted from that of the second reaction prior to further data analysis.

All other Compounds

Small molecule inhibition and binding titrations with compounds SU-1, SU-2, SU-4, SU-5, SU-7, SU-8, and SU-10-SU-36 (see FIG. 9 for structures), compound 968, compound 031, and compound 27 were performed in a 96-well format in a Tecan Saphire absorbance and fluorescence plate reader. The activity of GAC was measured in a coupled assay, by monitoring the NADH produced by glutamate dehydrogenase, which converts the product of the glutaminase-catalyzed reaction, glutamate, to α-ketoglutarate and ammonia by reducing NAD+ to NADH. Because solutions containing glutamine undergo non-enzymatic degradation to glutamate, samples were further analyzed by subtracting the NADH produced by glutaminase in the presence of 968, BPTES, or the equivalent volume of DMSO as a control, from the NADH produced in the absence of glutaminase under identical experimental conditions. NADH was quantified using a standard curve of freshly prepared NADH (Sigma) in 50 mM Tris-Acetate, pH 8.5, and 0.1 mM EDTA.

Detailed procedures for the real-time binding and inhibition assays adapted for 96-well microtiter format are as follows: 2 μL of inhibitor or DMSO was distributed across the 96-well plate, followed by addition of 200 μL 10 nM 488-GAC, unlabeled WT-GAC, or no added GAC as a negative control, in 50 mM Tris-Acetate, pH 8.5, and 0.1 mM EDTA, followed by immediate monitoring of 488 fluorescence (490 nm/520 nm excitation/emission, 5 nm/20 nm excitation/emission slits). The 488-fluorescence was measured every 2 minutes with 90 seconds of orbital shaking, followed by 30 seconds resting between each cycle for a total of four cycles (i.e. 6 minutes). A mixture of GDH and NAD+ (20 μL) was then added to give 10 units of GDH and 2 mM NAD+. To activate GAC, 30 μL of a mixture of glutamine and $K_2HPO_4$ was added to give a total concentration of 50 mM $K_2HPO_4$ and 20 mM glutamine in each well. NADH fluorescence was measured (340 nm/460 nm excitation/emission, 10 nm/10 nm excitation/emission slits) every minute with 30 seconds orbital shaking, and a 30 second rest between each reading, for 10 cycles (i.e. 9 minutes). Three wells were prepared for each experimental condition (i.e. each concentration of compound) alongside one well where 2 μL of DMSO was added in place of inhibitor, and one well that contained the small molecule inhibitor but no GAC. To analyze 488-quenching by the added compound, 488-fluorescence (F) was normalized to the DMSO control (F0). Quenching was quantified as follows: 1-F/F0. For compounds that emitted fluorescence within the observed range, fluorescence measured in the well that contained the compound but lacked GAC was used to subtract added fluorescence due to the compound. Similarly, samples were analyzed for NADH fluorescence by subtracting the fluorescence measured for the experimental condition from the NADH fluorescence in the well that contained the added compound but no GAC. Percent inhibition at each drug concentration was calculated using the adjacent DMSO control. FIGS. 10A-10AJ show both quenching and inhibition results for various inhibitors of GAC in vitro. The compounds were ranked in order of their potency as shown in FIG. 11. The correlation between $IC_{50}$ and $K_D$ of the GLS1 inhibitors is shown in FIG. 12.

Certain of the inhibitors were also tested for their ability to inhibit the KGA splice variant, using the same method described supra but using 488-KGA in place of 488-GAC. FIGS. 13A-F show both quenching and inhibition results for various inhibitors of KGA in vitro.

Example 18

Cell-Based Assay

MDA-MB-231 cells were cultured in RPMI-1640 media supplemented with 10% FBS. Prior to initiating the assay, cells that were 70-80% confluent were trypsinized, diluted, counted, and dispensed into 6-well culture plates at a density of $1 \times 10^4$ cells per well. Each well was then brought to 2 mL of media, total. The cells were allowed to adhere to the wells overnight. At this time, and every 72 hours thereafter, media was exchanged for media containing either the indicated amount of a given inhibitor, diluted from an appropriate DMSO stock, or an equivalent amount of DMSO without inhibitor. Cells were counted on the 6th day of culture. Cell counting was performed by aspirating media, rinsing the cells with room temperature PBS, and then incubating at 37°

Figure 14:
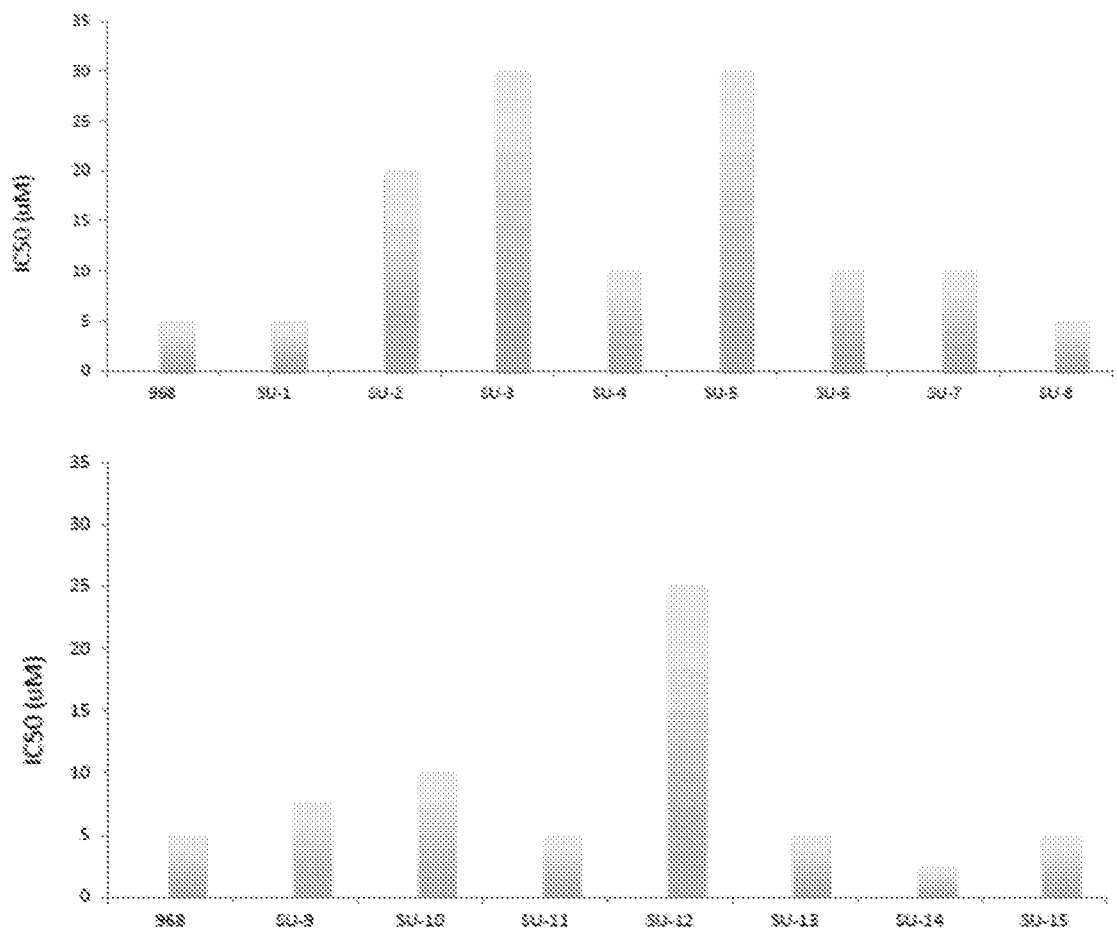
FIG. 14 is a chart showing the $IC_{50}$ values of 968 and SU-1 to SU-15 for the inhibition of cell growth in a proliferation assay using the breast cancer cell line MDA-MB-231.

C. for 5 minutes in 0.5 mL trypsin-EDTA solution. The culture plates were then agitated to fully dissociate cells from the plate surfaces, and 0.5 mL of RPMI-1640 complete media were added to quench trypsin activity. Cells were then counted on a hemocytometer, with 3 readings taken and averaged per sample. All experiments were performed in triplicate. Dose curves and $IC_{50}$ values were determined in Sigmaplot. $IC_{50}$ values are shown in FIG. 14. Using this assay, inhibitory properties of SU-16 to SU-20 were evaluated and are shown in FIG. 15.

Example 19

Covalent Cross Linking of Photo Reactive Compounds In Vitro and in Cells

Glutaminase proteins of the WT sequence, or containing the mutations D391K alone, or the mutations K316E/D391K/R459E, were purified as detailed in Example 3 supra. These glutaminase proteins were incubated with increasing concentrations of the compound SU-22, and excited with a hand held UV lamp for 120 seconds. Immediately following UV exposure, samples were loaded onto a 4-20% Tris-Glycine polyacrylamide gel after the addition of SDS-PAGE sample buffer (50 mM Tris-HCl (pH=6.8), 2% SDS, 10% glycerol, 1% β-mercaptoethanol, 12.5 mM EDTA, 0.02% bromophenol blue), and visualized on a UV light box.

Conditions of in vitro cross linking of WT GAC, and the K316E/D391K/R459E GAC mutant were adapted for efficient cross linking and purification of the cross linked protein product. WT GAC and the K316E/D391K/R459E GAC mutant, both containing the N-terminal His-tag, were diluted to a concentration of 100 nM in 20 mM Tris-HCl (pH=8.6) 100 mM NaCl, upon which 10 μM of SU-22 was added. Following a preincubation time of 5 minutes, samples were exposed to UV light under a hand held 500 W UV lamp to initiate the photo cross linking. Immediately following, bovine serum albumin (BSA, Sigma) was added to a final concentration of 2 mg/mL to help stabilize the cross linked product and to bind excess un-reacted SU-22. To isolate the cross linked product, 2.5 mg cobalt agarose beads (Clontech) were added and the solution was gravity filtered. The beads were first washed with 10 column volumes of 50 mM Tris-HCl (pH=8.6) 10 mM NaCl, 5 column volumes 50 mM Tris-HCl (pH=8.6) 10 mM NaCl containing 5 mM imidazole, 3 column volumes 50 mM Tris-HCl (pH=8.6) 10 mM NaCl containing 20 mM imidazole, and finally the cross linked product was eluted using 4 column volumes of 50 mM Tris-HCl (pH=8.6) 10 mM NaCl containing 320 mM imidazole. The purified cross linked protein was then concentrated using spin columns with a 30 kD molecular weight cutoff and quantified using UV-vis spectroscopy, where the protein was quantified using the A280 ($\varepsilon 280$=38,850 M−1 cm−1) and the cross-linked SU-22 using the A350 ($\varepsilon 350$=18,900 M−1 cm−1). Ratios of cross linked SU-22 to WT and K316E/D391K/R459E GAC were 0.52 and 0.78, respectively.

To further illustrate specific cross linking, the cross linked K316E/D391K/R459E was analyzed using analytical size exclusion chromatography, where 100 μg of cross linked K316E/D391K/R459E was injected onto a superdex 200 10/300 GL (GE Healthcare) equilibrated in 50 mM Tris-HCl (pH=8.6) 20 mM NaCl with a flow rate of 0.3 mL/min monitoring both the absorbance wavelengths at 280 nm and 350 nm.

The cross linked WT GAC was subjected to an overnight typsinization by first reacting all purified cross linked WT GAC (2.5 mg) with 10 mM iodoacetamide, followed by addition of 25 μg sequencing grade trypsin (Roche) and rotated overnight at 37° C. Following overnight trypsin digestion the solution was filtered using a 10 kD MW cutoff spin filter and injected onto a SunFire C18 100 Å 5 μm, 4.6 mm×150 mm (Waters). Peptides were eluted using a binary gradient elution protocol, where mobile phase A (5:95:0.1 acetonitrile:water:trifluoroacetic acid) and mobile phase B (95:5:0.1 acetonitrile:water:trifluoroacetic acid) were varied to produce an increase in acetonitrile up to 80% over 20 minutes at a flow rate of 1 mL/min. The wavelengths 254 nm and 35 nm were monitored.

Cross linking of SU-22 was also performed in cells transformed by the oncogene, Dbl. For these experiments, Dbl-induced MEFs, as detailed in Example 1 supra, were cultured in 150 mm² dishes to approximately 80% confluency in DMEM supplemented with 10% FBS. Cells were then washed and DMEM supplemented with 1% FBS and 5 μM SU-22 was added, and cells were cultured overnight. Cells were then exposed to 60 seconds of UV light by a hand held 50 W UV lamp to initiate the in cell cross linking, followed by washing with DMEM supplemented with 1% FBS without SU-22. Cells were incubated with DMEM supplemented with 1% FBS following UV exposure for 20 minutes. The cells were then trypsinized, and mitochondria were isolated as outlined in Frezza et al., "Organelle Isolation: Functional Mitochondria from Mouse Liver, Muscle, and Cultured Fibroblasts" *Nature Protocols* 2:287-95 (2007), which is hereby incorporated by reference in its entirety. Briefly, suspension of trypsinized cells were spun 600×g 10 minutes at 4° C. and suspended in mitochondrial isolation buffer (10 mM Tris-MOPS (pH=7.4), 1 mM EGTA/Tris, and 200 mM sucrose). Cells were homogenized in a glass potter with a Teflon pestle using a Dounce homogenizer operated at approximately 1600 rpm for 35 strokes. The homogenate was centrifuged 600×g 10 minutes at 4° C. and the supernatant was isolated. The pellet was lysed in RIPA lysis buffer and used as the P1 fraction containing the nucleus and unbroken cells. The supernatant was spun at 7000×g 10 minutes at 4° C., where the resultant pellet was the isolated mitochondria and the supernatant comprising the soluble cytosolic and microsomal fractions. The supernatant was isolated and spun at 200,000×g 1 hour at 4° C., and the resulting pellet was taken to be the S200 fraction containing cytosolic and microsomal components. The mitochondrial pellet was resuspended in mitochondrial isolation buffer and spun again at 7000×g 10 minutes at 4° C., where the resulting pellet was taken to be the purified isolated mitochondria.

For experiments where cells were visualized using confocal fluorescence microscopy, cells were cultured in the same conditions as stated above in MakTek 50 mm² dishes. Cells were treated with 5 mM SU-22 overnight in DMEM supplemented with 1% FBS. Following 30 seconds of UV exposure, media was replaced with fresh DMEM (1% FBS) and incubated at 37° C. for 2 hours. The media was then switched to DMEM (1 FBS) containing 250 nM of the mitochondrial fluorescent probe MitoTracker CMXRos and incubated at 37° C. for 30 minutes, at which point the media was changed to DMEM (1% FBS) without the MitoTracker for an additional 30 minutes. Cells were then fixed in 4% para-formaldehyde and 0.1% glutaraldehyde and imaged on an inverted Axio Observer.Z1 microscope using the 405 laser line for excitation of the SU-22 small molecule and 514 laser line to excite the MitoTracker.

For experiments using the novel compound SU-34, which contains both a photo-cross linking moiety along with a click chemistry ready alkyne functionality, cells were treated the same as stated above. Dbl-transformed cells were seeded in 150 mm² dishes and cultured overnight in DMEM supplemented with 1% FBS and 5 mM SU-34. Following 60 seconds UV exposure cells were harvested and mitochondria were isolated as described above. To each subcellular fraction, the click chemistry was performed by adding reagents to give a final concentration as follows: 20 mg protein, 100 mM MOPS (pH=7), 0.1 mM $CuSO_4$ and 0.5 mM Tris(3-hydroxypropyltriazolyl-methyl)amine (THPA) premixed, 5 mM ascorbate, 20 mM Alexa488-azide (molecular probes). The reaction was performed at 37° C. for 1 hour on a rotisserie inverter. SDS-PAGE sample buffer was added and each sample was run on a 4-20% Tris-glycine SDS-PAGE. The gel was first imaged for in gel fluorescence using the GelDoc XR+ molecular imager (Biorad), followed by transfer to PVDF and immunoblotting with the GLS1 antibody (AP8809b, Abgent).

FIGS. 16A-B show both SU-22 quenching and inhibition results following UV exposure.

Discussion of Examples 16-19

Figure 9:
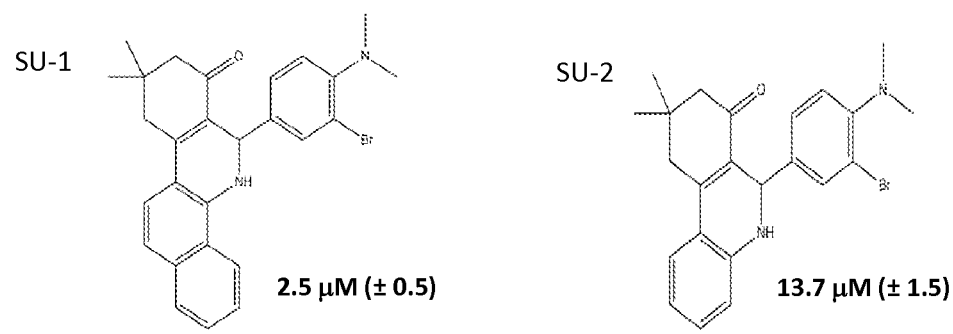
FIG. 9 shows the structure of GLS1 inhibitors SU-1 to SU-36 and depicts their $IC_{50}$ values as determined through an in vitro inhibition assay.
Figure 9:
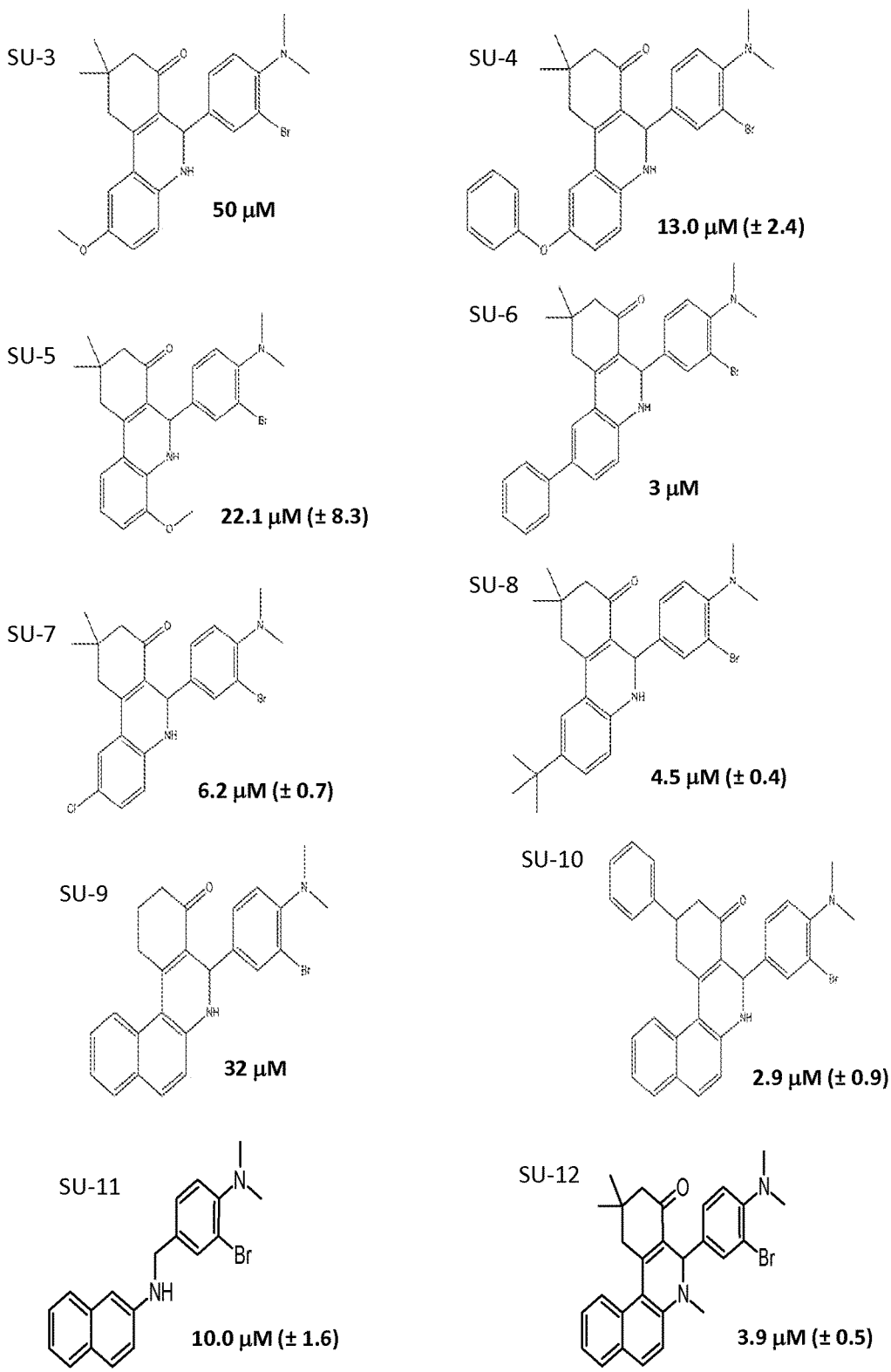
Figure 9:
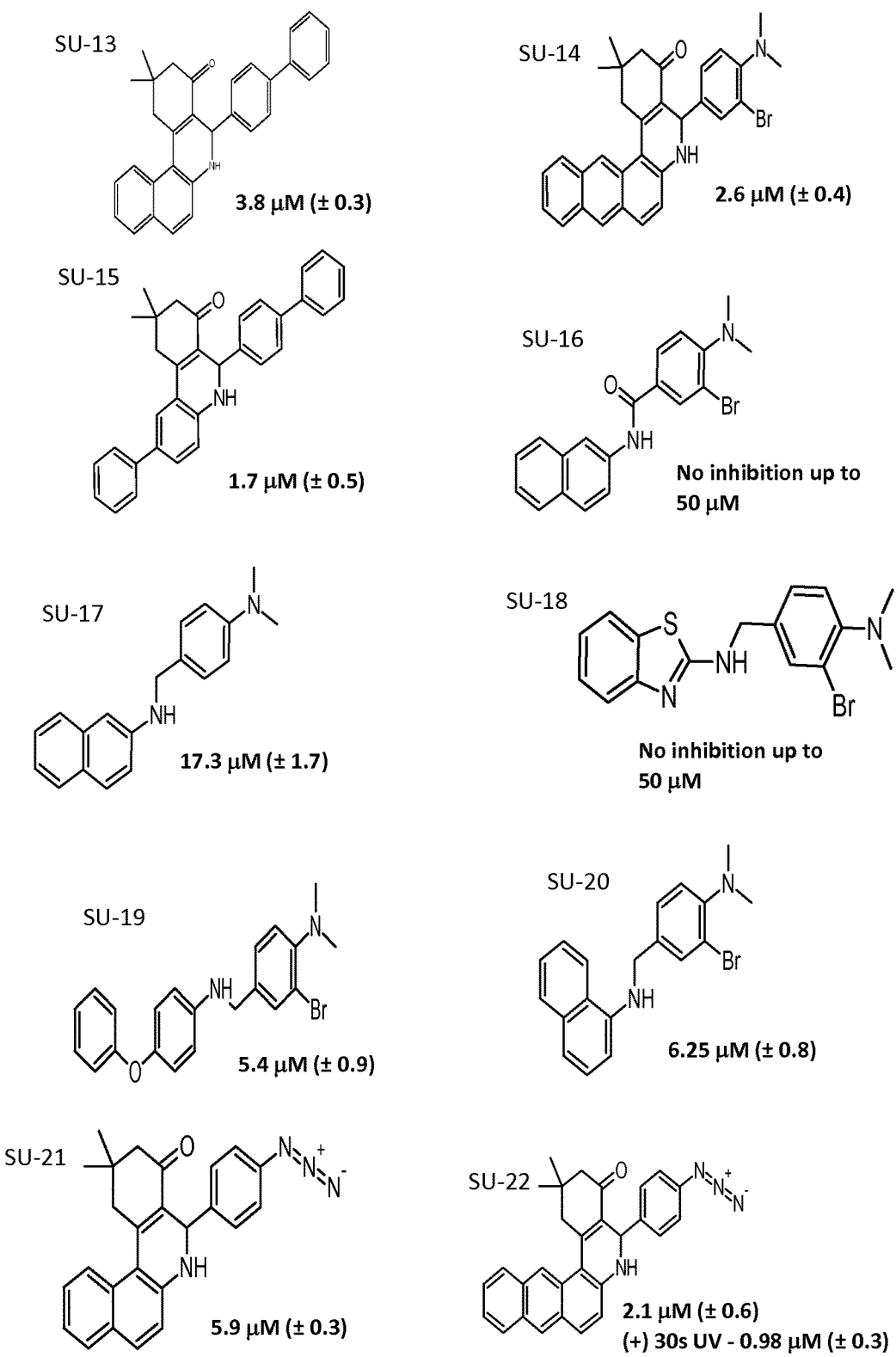
Figure 13F:
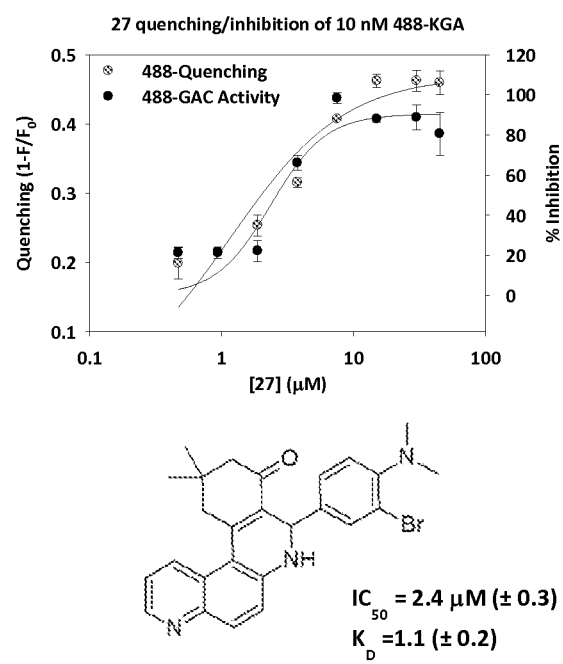

In vitro inhibition and binding assays of newly synthesized kidney-type glutaminase inhibitors are illustrated in FIGS. 9 through 13. These were obtained using the methods described in Stalnecker et al., "Mechanism by Which a Recently Discovered Allosteric Inhibitor Blocks Glutamine Metabolism in Transformed Cells," *PNAS* 112(2):394-99 (2013), which is hereby incorporated by reference in its entirety, where a fluorescently labeled GAC or KGA isoform was assayed first for the binding of these novel inhibitors followed by assaying the activity of the enzyme. FIG. 9 represents the in vitro inhibition of 968-like compounds as well as the novel scaffold described in this invention. FIG. 11 represents the in vitro inhibition data from FIG. 9 in a histogram, where trends are more clearly illustrated. Compounds SU-24, SU-15, SU-22, SU-1, SU-14, SU-10, SU-29, SU-20, and SU-31 inhibited the GAC isoform of the kidney-type glutaminase at a lower concentration than the parent compound, 968. Of these compounds, SU-29, SU-20, and SU-31 were derivatives of the novel scaffold disclosed in this invention, and represent model compounds for effective non-968 inhibitors of kidney-type glutaminase. The binding and inhibition data for these inhibitors were plotted on a two dimensional graph in FIG. 12, where a direct correlation of the binding of these small molecules (y-axis) and inhibition (x-axis) is illustrated. These results provide evidence for the novel compounds disclosed in this invention to bind to the same proposed binding site for the original small molecule 968, and demonstrate the resultant inhibition of enzymatic activity upon binding. The complete data set for each compound analyzed in this in vitro binding and inhibition assay for both 488-labeled GAC and 488-labeled KGA isoforms are presented in FIGS. 10A-AJ (GAC binding/inhibition), FIGS. 13A-F (KGA binding/inhibition), and FIGS. 16A-B (SU-22 quenching/inhibition following UV exposure). FIGS. 14 and 15 demonstrate the ability of the compounds disclosed in this invention to inhibit the growth of cancer cells. Thus, the compounds that are able to inhibit the enzyme glutaminase in vitro, are able to inhibit cancer cell growth by inhibiting the glutaminase enzyme present in cancer cells.

Figure 18B:
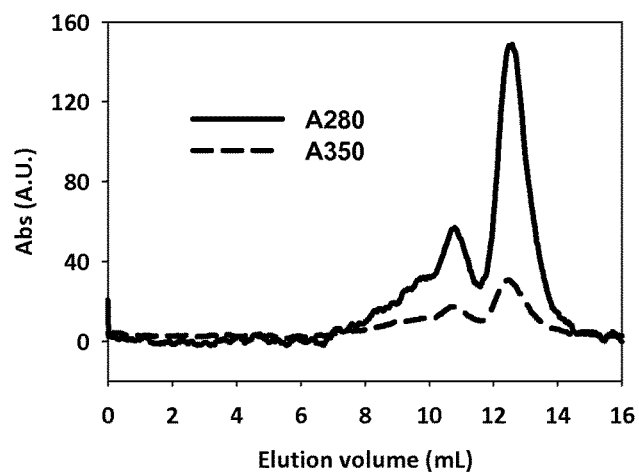
Figure 18C:
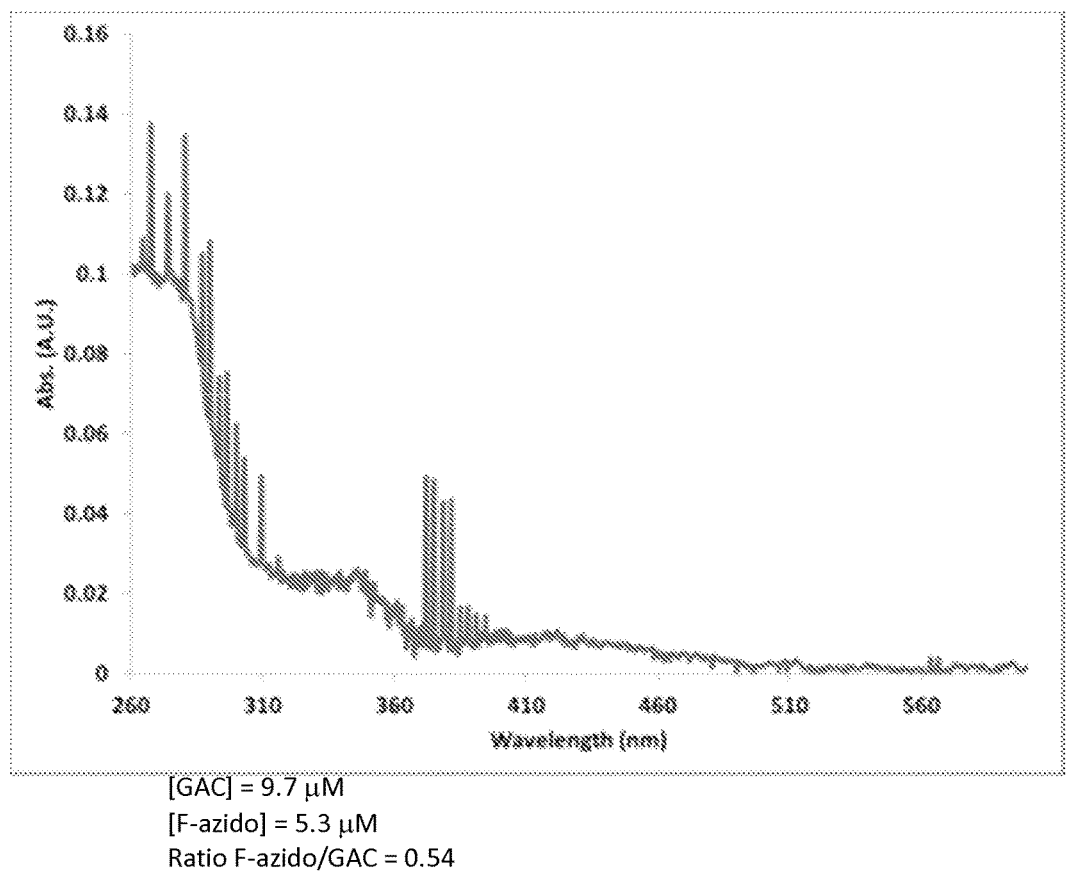
Figure 18D:
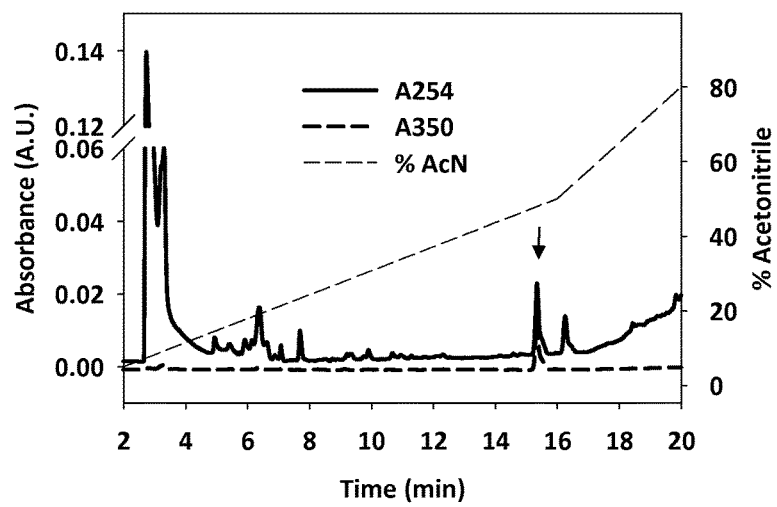

The use of the novel photo-cross linking 968 derivatives, as disclosed here, was investigated both in vitro and in cells. FIG. 17 illustrates the cross linking of SU-22 with the WT GAC isoform of GLS1, along with the mutants D391K, previously shown to be a constitutive dimer using the methods described above in Example 7, and K316E/D391K/R459E, shown to be a constitutive monomer. Consistent with previously published results (Stalnecker et al., "Mechanism by Which a Recently Discovered Allosteric Inhibitor Blocks Glutamine Metabolism in Transformed Cells," *PNAS* 112(2):394-99 (2013), which is hereby incorporated by reference in its entirety), the cross linking of the SU-22 was shown to be more efficient for the monomer mutant, i.e. K316E/D391K/R459E, when compared to the dimer (D391K), or WT GAC. The dose dependent cross linking was consistent with the inhibition profile of SU-34 for WT GAC, included here in FIG. 10AF. The methods for cross linking SU-22 to GAC in vitro were extended to develop a purification protocol of cross linking SU-22 to GLS1 proteins (see FIGS. 18A-D). The purification utilized the N-terminal 6x-His tag on purified GLS1 constructs, where the protein of interest was incubated with SU-22 and cross linked using UV irradiation. The protein SU-22 conjugate was then purified using cobalt agarose beads, where the elution of the labeled GLS1 protein was monitored by running each fraction on an SDS-PAGE and exciting with UV light to visualize the fluorescent SU-22 molecule. FIG. 18A illustrates the fluorescence of each fraction of the purification protocol for cross linking SU-22 to the K316E/D391K/R459E GAC mutant, where strong fluorescence was visualized in the elution fractions, but not the original sample (compare lanes 1 and 8). Additionally, the total protein in each fraction was visualized using Coomassie blue staining, further illustrating the purification of the SU-22 labeled species. The isolated SU-22 conjugate was further analyzed using analytical gel filtration, as illustrated in FIG. 18B, where the absorbance trace at 280 nm represents the elution of the protein species and the absorbance trace at 350 nm represents the absorbance of the small molecule, SU-22. Two distinct peaks are observed, corresponding to the monomer and dimer of GAC, consistent with this small molecule binding at the interface between two monomers as shown previously. This method was extended to include the WT GAC protein, where the final protein SU-22 conjugate was analyzed using UV-vis spectroscopy. FIG. 18C illustrates the absorbance profile of the isolated SU-22 WT GAC conjugate, where the absorbance at 350 nm is characteristic of the small molecule SU-22. Additionally, this SU-22 WT GAC conjugate was subjected to further analysis and characterization by trypsin digestion and subsequent analysis of the resultant peptides by HPLC. FIG. 18D illustrates the HPLC profile of the WT SU-22 conjugate, where the absorbance trace at 254 nm represents any eluted peptides, and the absorbance at 350 nm represents the small molecule SU-22 conjugated peptide (arrow). These results represent general methods for the covalent modification and purification of GLS1 proteins with the photo-cross linker described here, SU-22.

Figure 19:
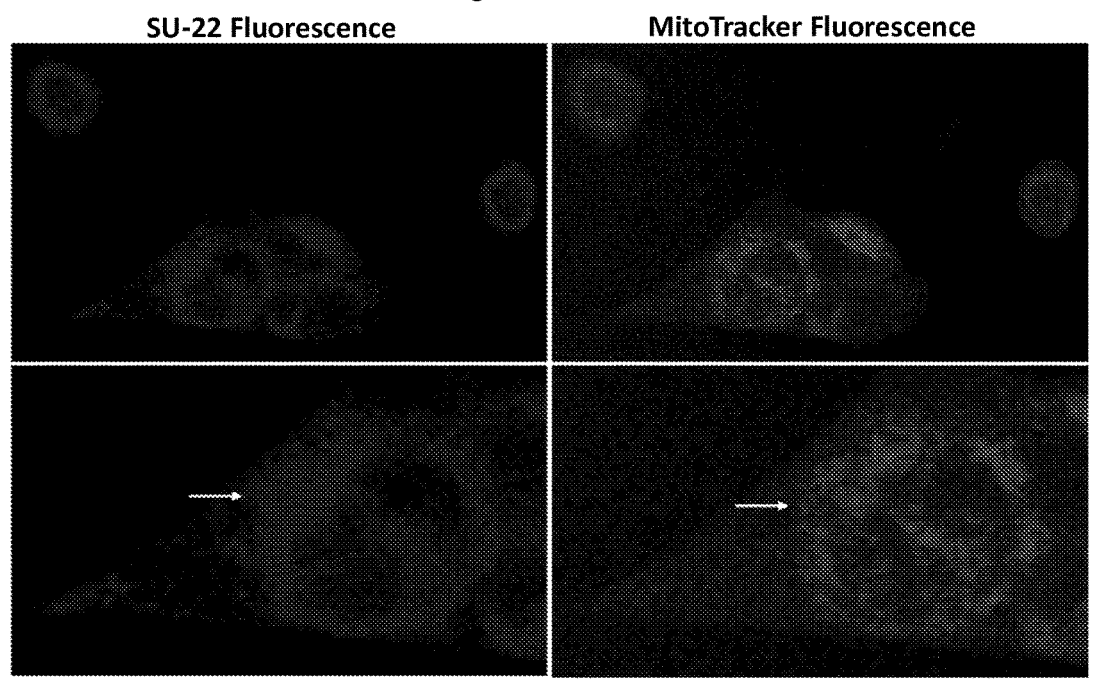
FIG. 19 shows confocal microscopy images of fixed Dbl-transformed MEFs following UV stimulation, showing the subcellular localization of the fluorescent 968 derivative, SU-22, cross linked in Dbl transformed cells.
Figure 20:
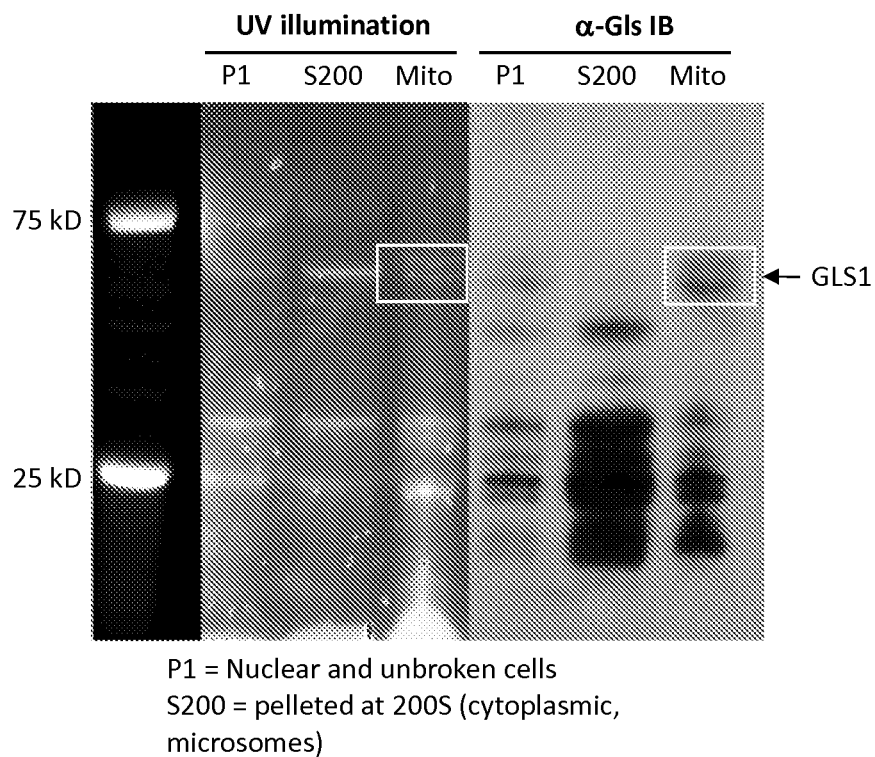
FIG. 20 shows SDS-PAGE gels relating to the isolation of the photo cross linker, SU-22, cross linked to glutaminase proteins following UV exposure.

Experiments were conducted to also analyze these novel GLS1 inhibitor photo-cross linkers in cells. FIG. 19 illustrates confocal microscopy images of fixed Dbl-transformed MEFs following UV stimulation, which initiates the cross linking of SU-22 in cells, and subsequent washing of excess unreacted SU-22 followed by labeling of cellular mitochondria with the reliable MitoTracker probe. These images demonstrate the subcellular localization of the SU-22 small molecule, where co-localization is observed to be most consistent with mitochondrial labeling. Additionally, these methods of cross linking SU-22 in cells was extended to purify conjugated SU-22 proteins. FIG. 20 illustrates the subcellular fraction of Dbl-transformed cells cross linked with SU-22, where the each fraction was analyzed by SDS-PAGE. SU-22 conjugated proteins were visualized by illumination of the gel by UV light, where distinct bands could be visualized. The gel was then transferred to PVDF membrane and analyzed by immunoblotting with the GLS1 antibody, and similar banding patterns were found to be characteristic of SU-22 cross linked GLS1 proteins (white box). These results also further suggest the localization of this small molecule to the mitochondrial fraction.

Figure 21:
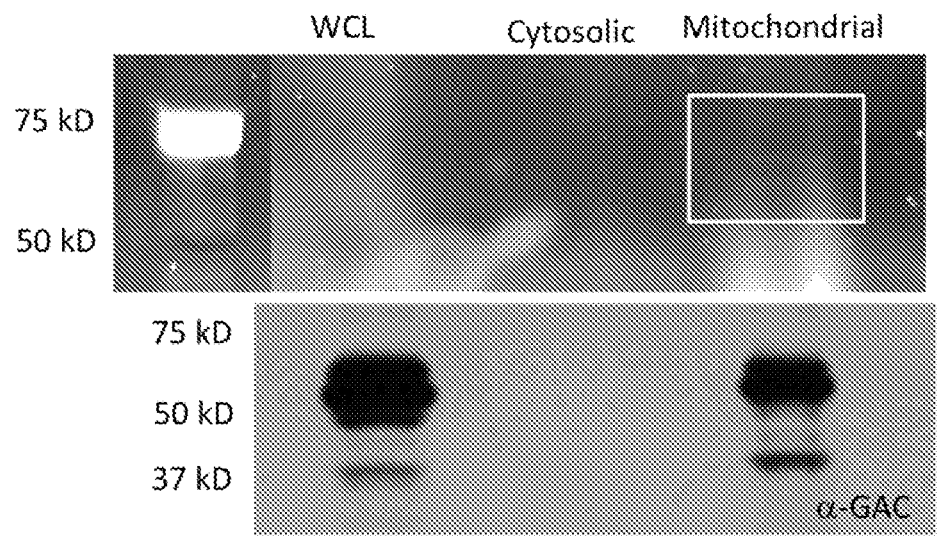
FIG. 21 relates to the isolation of the photo cross linker, SU-34, cross linked to glutaminase proteins following UV exposure and subsequent copper catalyzed click chemistry to attach the highly fluorescent probe, alexa-488 azide.

In order to investigate the use of these novel GLS1 inhibitor cross linkers, these methods were extended for the use of the novel SU-34 cross linker. This cross linker contains both a photo reactive moiety and a click chemistry ready alkyne functional group. FIG. 21 illustrates a cross linking experiment, where Dbl-transformed cells were incubated with the SU-34 compound and cross linked following UV exposure. Following the cross linking, the cells were subfractionated as previously described and samples from each fraction were reacted using click chemistry to the highly fluorescent Alexa488 azide probe. The fractions were then analyzed by SDS-PAGE and SU-34 cross linked proteins, following the addition of the highly fluorescent Alexa488 azide via click chemistry, were visualized by fluorescence under UV excitation (white box). These samples were then transferred to PVDF membrane and immunoblotted using a GLS1 antibody. These results are consistent with those included for the SU-22 photo-cross linker, where the fluorescence of the cross linked small molecule protein conjugate is consistent with the labeling of GLS1 proteins in cells.

In conclusion, binding and inhibition data for the new compounds illustrated in FIG. 9 were obtained using the fluorescently labeled GAC and KGA isoforms. The data presented in Examples 16-19 demonstrate the efficacy of these novel compounds, and present evidence for these inhibitors to occupy the same binding site as the parent compound, 968. Indeed, a novel inhibitor scaffold is described, where the efficacy of such was shown to be as potent, or in some derivatives more potent, than 968 itself. Additionally, a class of 968-derivatives that contain functional groups that allow for the covalent attachment of the small molecule to the protein target are described. These compounds were shown to inhibit GLS1 in the same manner as the parent compound, 968. Furthermore, the covalent cross linking and purification of protein conjugates both in vitro and in vivo are described, along with methods of analysis to assess the function or subcellular localization. Combined, these novel compounds represent a new class of inhibitors of GAC activity.

What is claimed:
1. A compound, or a pharmaceutically acceptable salt, ester, enol ether, enol ester, solvate, hydrate, or prodrug thereof, wherein the compound is a compound of Formula IIA:

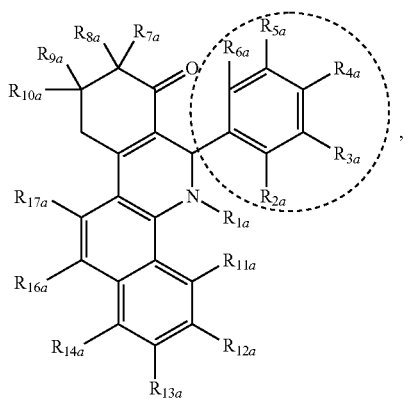

IIA wherein:
the dotted circle identifies an active moiety;
$R_{1a}$ is independently H, —OH, —$OR_{14a}$, $C_1$-$C_6$ alkyl, $C_2$-$C_6$ alkenyl, $C_2$-$C_6$ alkynyl, $R_{14a}C(O)$—, $R_{14a}OC(O)$—, $R_{14a}S(O)$—, or $R_{14a}S(O)_2$—;
$R_{2a}$, $R_{3a}$, $R_{4a}$, $R_{5a}$, and $R_{6a}$ are each independently a photoreactive moiety, H, halogen, —$NO_2$, —OH, —$OR_{14a}$, —$SR_{14a}$, —$NH_2$, —$NHR_{14a}$, —$NR_{14a}R_{15a}$, $R_{14a}C(O)$—, $R_{14a}OC(O)$—, $R_{14a}C(O)O$—, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; or $R_{2a}$ and $R_{3a}$, $R_{3a}$ and $R_{4a}$, $R_{4a}$ and $R_{5a}$, or $R_{5a}$ and $R_{6a}$ are combined to form a heterocyclic ring optionally substituted with a photoreactive moiety; wherein at least two of $R_{2a}$, $R_{3a}$, $R_{4a}$, $R_{5a}$, and $R_{6a}$ are not hydrogen;
$R_{7a}$, $R_{8a}$, $R_{9a}$, and $R_{10a}$ are each independently a photoreactive moiety, H, —OH, —$NH_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the aryl, heteroaryl, and aryl $C_1$-$C_6$ alkyl are optionally substituted from 1 to 3 times with substituents selected from the group consisting of, halogen, —OH, —$NH_2$, $C_1$-$C_6$ alkyl, $C_2$-$C_6$ alkenyl, $C_1$-$C_6$ alkoxy, —SH, and $C_1$-$C_6$ thioalkyl, and wherein the alkyl, alkenyl, alkynyl, cycloalkyl, cycloalkylalkyl, arylalkyl, mono or polycyclic aryl, and mono or polycyclic heteroaryl are optionally substituted with a photoreactive moiety; and
$R_{11a}$, $R_{12a}$, $R_{13a}$, $R_{14a}$, $R_{15a}$, $R_{16a}$, and $R_{17a}$ are each independently a photoreactive moiety, H, halogen, —OH, —$NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, wherein the alkyl, alkenyl, alkynyl, cycloalkyl, cycloalkylalkyl, arylalkyl, and mono or polycyclic aryl are optionally substituted with a photoreactive moiety and each one of $R_{11a}$-$R_{17a}$ is optionally substituted with —$NH_2$, —OH, halogen, —COOH, —$NO_2$, and —CN; and
wherein the compound is optionally modified to include a tag and/or an attachment to a solid surface.
2. The compound according to claim 1, wherein the compound is SU-1:

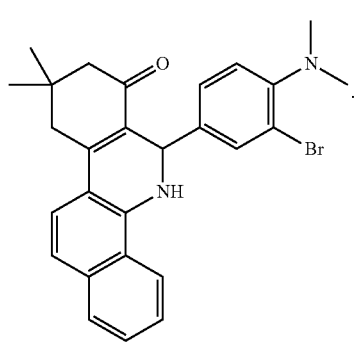

SU-1

3. The compound according to claim 1, wherein the compound comprises a photoreactive moiety selected from the group consisting of aryl azides, diazirines, and benzophenone.

4. The compound according to claim 3, wherein the photoreactive moiety is selected from the group consisting of —N=N⁺=N⁻;

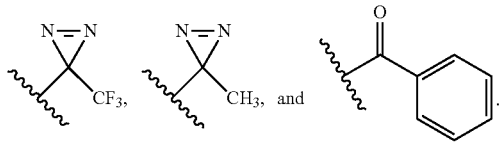

5. The compound according to claim 1, wherein the compound comprises an active moiety of formula:

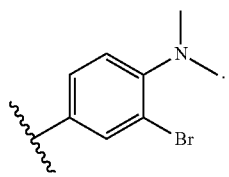 [SMILES: *c1ccc(N(C)C)c(Br)c1]

6. A pharmaceutical composition comprising:
a compound of claim 1, or a pharmaceutically acceptable salt, ester, enol ether, enol ester, solvate, hydrate, or prodrug thereof.

7. The pharmaceutical composition according to claim 6 further comprising:
a pharmaceutically acceptable carrier.

8. A method of treating a subject with a condition mediated by production of glutamate from glutamine by glutaminase GLS1, said method comprising:
selecting a subject with a condition mediated by production of glutamate from glutamine by glutaminase GLS1 and
administering to said selected subject an inhibitor of glutaminase GLS1 activity under conditions effective to treat the condition mediated by production of glutamate from glutamine, wherein the inhibitor is a compound according to claim 1, or a pharmaceutically acceptable salt, ester, enol ether, enol ester, solvate, hydrate, or prodrug thereof.

9. A method of reducing the production of glutamate from glutamine by glutaminase GLS1 in a sample, said method comprising:
inhibiting glutaminase GLS1 activity in the sample by a method comprising:
providing a compound and
contacting glutaminase GLS1 in the sample with the compound to reduce the production of glutamate from glutamine in the sample,
wherein the compound is a compound according to claim 1, or a pharmaceutically acceptable salt, ester, enol ether, enol ester, solvate, hydrate, or prodrug thereof.

10. A method of detecting glutaminase GLS1 protein in a sample, said method comprising:
providing a sample potentially containing glutaminase GLS1 protein;
contacting the sample with a compound comprising a photoreactive moiety;
exposing the compound to a light source under conditions effective to form a conjugate between the compound and glutaminase GLS1 protein, if present in the sample, through covalent modification of the photoreactive moiety; and
detecting whether any compound-glutaminase GLS1 protein conjugates are formed, wherein formation of a compound-glutaminase GLS1 protein conjugate indicates the presence of glutaminase GLS1 protein in the sample;
wherein the compound is a compound according to claim 1, or a pharmaceutically acceptable salt, ester, enol ether, enol ester, solvate, hydrate, or prodrug thereof.

11. A method of producing a glutaminase inhibitor-glutaminase GLS1 protein conjugate in a sample;
providing a sample containing one of (i) glutaminase GLS1 protein and (ii) a compound comprising a photoreactive moiety;
contacting the sample with the other of (i) glutaminase GLS1 protein and (ii) a compound comprising a photoreactive moiety; and
exposing the compound to a light source under conditions effective to form a conjugate between the compound and glutaminase GLS1 protein through covalent modification of the photoreactive moiety;
wherein the compound is a compound according to claim 1, or a pharmaceutically acceptable salt, ester, enol ether, enol ester, solvate, hydrate, or prodrug thereof.

12. The method according to claim 11 further comprising:
(i) detecting the compound, the conjugate, and/or the glutaminase GLS1 protein;
(ii) quantitating the amount of compound, the conjugate, and/or the glutaminase GLS1 protein present in the sample;
(iii) isolating the compound, the conjugate, and/or the glutaminase GLS1 protein from the sample;
(iv) purifying the compound, the conjugate, and/or the glutaminase GLS1 protein; or
(v) any combination thereof.

13. The compound according to claim 1, wherein the compound is modified to include a tag and/or an attachment to a solid surface.

14. A pharmaceutically acceptable salt, ester, enol ether, enol ester, solvate, hydrate, or prodrug of a compound according to claim 1.

* * * * *

UNITED STATES PATENT AND TRADEMARK OFFICE
CERTIFICATE OF CORRECTION

PATENT NO. : 10,526,322 B2
APPLICATION NO. : 15/533198
DATED : January 7, 2020
INVENTOR(S) : Cerione et al.

It is certified that error appears in the above-identified patent and that said Letters Patent is hereby corrected as shown below:

In the Specification

Column 1 at Line 12, delete "grant number 2R01GM40654" and insert in its place --GM040654--

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*